(12) United States Patent
Mukerji et al.

(10) Patent No.: US 7,070,970 B2
(45) Date of Patent: Jul. 4, 2006

(54) ELONGASE GENES AND USES THEREOF

(75) Inventors: Pradip Mukerji, Gahanna, OH (US); Tapas Das, Worthington, OH (US); Yung-Sheng Huang, Upper Arlington, OH (US); Jennifer Parker-Barnes, New Albany, OH (US); Amanda E. Leonard, Columbus, OH (US); Jennifer M. Thurmond, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 612 days.

(21) Appl. No.: 10/408,736

(22) Filed: Apr. 4, 2003

(65) Prior Publication Data

US 2003/0177508 A1 Sep. 18, 2003

Related U.S. Application Data

(62) Division of application No. 09/379,095, filed on Aug. 23, 1999, now abandoned.

(51) Int. Cl.
C12N 9/10 (2006.01)
C12N 1/20 (2006.01)
C12N 15/00 (2006.01)
C07H 21/04 (2006.01)

(52) U.S. Cl. ............... 435/193; 435/252.3; 435/252.33; 435/325; 435/320.1; 435/254.1; 435/254.2; 435/254.31; 435/348; 435/254.11; 435/419; 435/254.21; 435/254.22; 435/254.23; 435/254.3; 435/254.4; 435/254.5; 435/254.6; 536/23.2

(58) Field of Classification Search ................. 435/193, 435/252.3, 252.33, 325, 320.1, 254.1, 254.2, 435/252.31, 348, 254.11, 419, 254.21, 254.22, 435/254.23, 254.3, 254.4, 254.5, 254.6; 536/23.2
See application file for complete search history.

(56) References Cited

U.S. PATENT DOCUMENTS

| 4,666,701 | A | 5/1987 | Horrobin et al. |
|---|---|---|---|
| 4,758,592 | A | 7/1988 | Horrobin et al. |
| 4,826,877 | A | 5/1989 | Stewart et al. |
| 4,943,674 | A | 7/1990 | Houck et al. |
| 5,106,739 | A | 4/1992 | Comai et al. |
| 5,116,871 | A | 5/1992 | Horrobin et al. |
| 5,175,095 | A | 12/1992 | Martineau et al. |
| 5,188,958 | A | 2/1993 | Moloney et al. |
| 5,196,198 | A | 3/1993 | Shaw et al. |
| 5,420,034 | A | 5/1995 | Kridl et al. |
| 5,443,974 | A | 8/1995 | Hitz et al. |
| 5,463,174 | A | 10/1995 | Moloney et al. |
| 5,484,724 | A | 1/1996 | El-Sherbeini et al. |
| 5,545,553 | A | 8/1996 | Gotschlich |
| 5,552,306 | A | 9/1996 | Thomas et al. |
| 5,589,379 | A | 12/1996 | Kridl et al. |
| 5,700,671 | A | 12/1997 | Prieto et al. |
| 5,750,176 | A | 5/1998 | Prieto et al. |
| 6,403,349 | B1 | 6/2002 | Mukerji et al. |

FOREIGN PATENT DOCUMENTS

| EP | 0296751 | A | 12/1988 |
|---|---|---|---|
| EP | 0296751 | | 12/1988 |
| FR | 2648347 | A | 12/1990 |
| FR | 2648347 | | 12/1990 |
| WO | 8807577 | A | 10/1988 |
| WO | 8807577 | | 10/1988 |
| WO | 9311245 | | 6/1993 |
| WO | 9411516 | | 5/1994 |
| WO | 95/24494 | | 9/1995 |
| WO | 9610086 | | 4/1996 |
| WO | 9613591 | | 5/1996 |
| WO | 98/39448 | | 9/1998 |
| WO | 9846765 | A | 10/1998 |
| WO | 0012720 | | 3/2000 |
| WO | 0159128 | A | 8/2000 |
| WO | 0070945 | A | 11/2000 |

OTHER PUBLICATIONS

Tvrdik, P., et al., "Role of a New Mammalian Gene Family in the Biosynthesis of Very Long Chain Fatty Acids and Sphingolipids," The Journal of Cell Biology, vol. 149, No. 3 (May 1, 2000), pp. 707–717.
Database EMBL [online] Oct. 19, 1999, Hashimo, K., et al.: "Mus Musculus Brain cDNA, Clone:MNCb–4912, 5' end." Database Accession No. AU079897 XP002223157.
Das, T., et al., ".Gamma.–Linolenic Acid Metabolism: Identification and Characterization of.Gamma.–Linolenic Acid Elongation Enzyme" International Symposium on .Gamma-Linolenic Acid, $2^{nd}$, San Diego, CA, Apr. 25–28, 2000, XP008011237, In: .Gamma.–Linolenic Acid: Recent Advances in Biotechnology and Clinical Applications (2001), AOCS Press, Champaign, Il. pp44–60 85 Feb. 10, 2005.
Kendrick, A, et al., "Lipids of Selected Molds Grown for Production of N–3 and N–6 Polyunsaturated Fattt Acids," vol. 27, No. 1, 1992, pp. 15–20, XP002047887, ISSN: 0024–4201.

(Continued)

Primary Examiner—Rebecca E. Prouty
Assistant Examiner—Sheridan L. Swope
(74) Attorney, Agent, or Firm—Cheryl L. Becker

(57) ABSTRACT

The subject invention relates to the identification of four genes involved in the elongation of polyunsaturated acids (i.e., "elongases") and to uses thereof. Two of these genes are also involved in the elongation of monounsaturated fatty acids. In particular, elongase is utilized in the conversion of gamma linolenic acid (GLA) to dihomogamma linolenic acid (DGLA) and in the conversion of DGLA or 20:4n-3 to eicosapentaenoic acid (EPA). DGLA may be utilized in the production of polyunsaturated fatty acids, such as arachidonic acid (AA), docosahexaenoic acid (DHA), EPA, adrenic acid, ω6-docosapentaenoic acid or ω3-docosapentaenoic acid which may be added to pharmaceutical compositions, nutritional compositions, animal feeds, as well as other products such as cosmetics.

19 Claims, 55 Drawing Sheets

OTHER PUBLICATIONS

Salem, N. et al., "Arachidonic and Docosahexaenoic Acids are Biosynthesized from their 18–Carbon Precursors in Human Infants," Proceedings of the National Academy of Sciences of USA, National Academy of Science, vol. 93, (Jan., 1996), pp. 49–54, XP002131822, ISSN: 0027–8424.

Bowles, R.D., et al., "Long–Chain N–3 Polyunsaturated Fatty Acid Production by Members of the Marine Protistan Group the Thraustochytrids: Screening of Isolates and Optimisation of Docosahexaenoic Acid Production," Journal of Biotechnology, Elsevier Science Publishers, Amsterdam, NL, vol. 70, No. 1–3, (Apr. 30, 1999) pp. 193–2002, XP004173399 ISSN: 0168–1656.

Lassner et al., Plant Cell 8:281–292 (1996).

Oh et al., The Journal of Biological Chemistry 272 (28): 17376–17384 (1997).

Patent Abstracts of Japan—vol. 1998, No. 08, Jun. 30, 1998 & JP10070992A Mar. 17, 1998.

Database EMBL Accession No. R63251, May 30, 1995 Hillier L., et al.,: "*homo sapiens* clone 138518 (EST)" XP002131823.

Salem N, et al., "Arachidonic and docosahexaenoic acids are biosynthesized from their 18–carbon precursors in human infants" Proceedings of the National Academy of Sciences, USA, vol. 93, Jan. 1996, pp. 49–54, XP002131822.

Browse, et al., "Glycerolipid Synthesis: Biotechnology and Regulation", Annu. Rev. Plant Physiol. Plant Mol. Biol., vol. 42 (1991) pp. 467–506.

Cassagne, et al., "Biosynthesis of Very Long Chain Fatty Acid in Higher Plants," Prog. Lipid Res., vol. 33, No. ½, (1994), pp. 55–69.

Silve, S., et al., GenBank Database, Accession No. X82033 Sep. 11, 1996.

Altschul, et al., *Nuc. Acids Res.*, vol. 25 (1997) pp. 3389–3402.

Ausubel, et al., *Short Protocols in Molecular Biology*, Ch. 13 (1992) pp. 3–5.

Brenner, et al., *Adv. Exp. Med. Biol.*, vol. 83 (1976) pp. 85–101.

Gietz, et al., *Mol. Cell. Biol*, vol. 5 (1995) pp. 255–269.

Hoffman, et al., *Gene*, vol. 57 (1987) p. 267.

Horrobin, et al., *Am. J. Clin. Nutr.*, vol. 57 (Suppl.) pp. 732S–737S (1993).

Hoveland, et al., *Gene* vol. 38 (1989) pp. 57–64.

Knutzon, et al., *J. Biol. Chem.* vol. 273 (1998) pp. 29360–29366.

Pearson and Lipman, *Proc. Natl. Acad. Sci.* USA, vol. 85, (1988) pp. 2444–2448.

Schnieke, et al., *Science*, vol. 278, (1997) pp. 2130–2133.

Gap Weight:        6    Average Match:    2.912
   Length Weight:  4    Average Mismatch: -2.003

Quality:   50         Length:    84
             Ratio:   0.625        Gaps:     4
Percent Similarity: 43.038   Percent Identity: 29.114

Match display thresholds for the alignment(s):
                | = IDENTITY
                : = 2
                . = 1 jojobakcs x ELO2          June 4, 1998 08:23  ..

jojobakcs   24 ATLPNFKSSINLHHVKL.GYHYLISNALFLVFIPLLGLASAHLSSFSAHD 72
               .|||   .|  ::|:|   :|:|.   |  |||   |     ..
ELO2        66 STLPPVLYAITAYYVIIFGGRFLLSKS..KPF.KLNGLFQLHNLVLTSLS 112 jojobakcs   73 LSLLFDLLRRNLLPVVVCSFLFVLLATLHFLTRP 106
               |.||  |:  |.|::|   |:   :   |.|
ELO2       113 LTLLL.LMVEQLVPIIVQHGLYFAICNIGAWTQP 145

FIG.2

S. cerevisiae ELO2 (AA66-145) with M. alpina codon bias

```
 S   T   L   P   P   V   L   Y   A   I   T   A   Y   Y   V   I   I   F   G   G   R   F   L
TCC ACC CTC CCC CCC GTC CTC TAC GCC ATC ACC GCC TAC TAC GTC ATC ATC TTC GGT GGT CGC TTC CTC
 66  67  68  69  70  71  72  73  74  75  76  77  78  79  80  81  82  83  84  85  86  87  88
                                                                  <-- R0339

L   S   K   S   K   P   F   K   L   N   G   L   F   Q   L   H   N   L   V   L   T   S   L
CTC TCC AAG TCC AAG CCC TTC AAG CTC AAC GGT CTC TTC CAG CTC CAC AAC CTC GTC CTC ACC TCC CTC
 89  90  91  92  93  94  95  96  97  98  99 100 101 102 103 104 105 106 107 108 109 110 111

S   L   T   L   L   L   L   M   V   E   Q   L   V   P   I   I   V   Q   H   G   L   Y   F
TCC CTC ACC CTC CTC CTC CTC ATG GTC GAG CAG CTC GTC CCC ATC ATC GTC CAG CAC GGT CTC TAC TTC
112 113 114 115 116 117 118 119 120 121 122 123 124 125 126 127 128 129 130 131 132 133 134

A   I   C   N   I   G   A   W   T   Q   P
GCC ATC TGC AAC ATC GGT GCC TGG ACC CAG CCC
135 136 137 138 139 140 141 142 143 144 145
```

FIG.3

```
pRAE-5    GAATTCAGG * * * * * * *CATGGCCGCCGCAATCTTGGACAA
pRAE-6    GAATTCAGGCATCTCATGGATCCGCCATGGCCGCCGCAATCTTGGACAA
          EcoRI              BamHI    NcoI
```

FIG.5

```
  1  ATGGCCGCCG CAATCTTGGA CAAGGTCAAC TTCGGCATTG ATCAGCCCTT
 51  CGGAATCAAG CTCGACACCT ACTTTGCTCA GGCCTATGAA CTCGTCACCG
101  GAAAGTCCAT CGACTCCTTC GTCTTCCAGG AGGGCGTCAC GCCTCTCTCG
151  ACCCAGAGAG AGGTCGCCAT GTGGACTATC ACTTACTTCG TCGTCATCTT
201  TGGTGGTCGC CAGATCATGA AGAGCCAGGA CGCCTTCAAG CTCAAGCCCC
251  TCTTCATCCT CCACAACTTC CTCCTGACGA TCGCGTCCGG ATCGCTGTTG
301  CTCCTGTTCA TCGAGAACCT GGTCCCCATC CTCGCCAGAA ACGGACTTTT
351  CTACGCCATC TGCGACGACG GTGCCTGGAC CCAGCGCCTC GAGCTCCTCT
401  ACTACCTCAA CTACCTGGTC AAGTACTGGG AGTTGGCCGA CACCGTCTTT
451  TTGGTCCTCA AGAAGAAGCC TCTTGAGTTC CTGCACTACT CCACCACTC
501  GATGACCATG GTTCTCTGCT TGTCCAGCT TGGAGGATAC ACTTCAGTGT
551  CCTGGGTCCC TATTACCCTC AACTTGACTG TCCACGTCTT CATGTACTAC
601  TACTACATGC GCTCCGCTGC CGGTGTTCGC ATCTGGTGGA AGCAGTACTT
651  GACCACTCTC CAGATCGTCC AGTTCGTTCT TGACCTCGGA TTCATCTACT
701  TCTGCGCCTA CACCTACTTC GCCTTCACCT ACTTCCCCTG GCTCCCAAC
751  GTCGGCAAGT GCGCCGGTAC CGAGGGTGCT GCTCTCTTTG GCTGCGGACT
801  CCTCTCCAGC TATCTCTTGC TCTTTATCAA CTTCTACCGC ATTACCTACA
851  ATGCCAAGGC CAAGGCAGCC AAGGAGCGTG AAGCAACTT TACCCCCAAG
901  ACTGTCAAGT CCGGCGGATC GCCCAAGAAG CCCTCCAAGA GCAAGCACAT
951  CTAA
```

FIG. 6

```
  1  MAAAILDKVN FGIDQPFGIK LDTYFAQAYE LVTGKSIDSF VFQEGVTPLS
 51  TQREVAMWTI TYFVVIFGGR QIMKSQDAFK LKPLFILHNF LLTIASGSLL
101  LLFIENLVPI LARNGLFYAI CDDGAWTQRL ELLYYLNYLV KYWELADTVF
151  LVLKKKPLEF LHYFHHSMTM VLCFVQLGGY TSVSWVPITL NLTVHVFMYY
201  YYMRSAAGVR IWWKQYLTTL QIVQFVLDLG FIYFCAYTYF AFTYFPWAPN
251  VGKCAGTEGA ALFGCGLLSS YLLLFINFYR ITYNAKAKAA KERGSNFTPK
301  TVKSGGSPKK PSKSKHI*
```

```
            301                                                         350
    GNS1    LF I S FY I N V Y K R G T K T S R V V K R A H G G V A A K V N E Y Y V N V D L K N V P T P S P
    SUR4    LF I S FY I Q S Y K K G K K T K F T K E S E V S G . S V A S G S T G V K T S N I K V S S R K A
    MAELO   LF I N FY R I T Y N A K A K A A K E R G S N F T P K T V K S G G S P K . K P S K S K H I *

351
    GNS1    K P Q H R R K R
    SUR4
    MAELO
```

FIG.8B

```
SCORES      Init1:  153 Initn:  199 Opt:  495
  57.4% identity in 549 bp overlap 150       160       170       180       190       200
MAELO    TCTCGACCCAGAGAGAGGTCGCCATGTGGACTATCACTTACTTCGTCGTCATCTTTGGTG
         ||||||    ||   |||  ||    || ||   || ||    ||
S78624   CATTAAGCACTTTGCCCCCTGTGCTATACGCCATCACTGCCTATTACGTTATTATTTTTG
            5990      6000      6010      6020      6030      6040

210       220       230       240       250       260
MAELO    GTCGCCAGATCATGAAGAGCCAG--GACGCC-TTCAAGCTCAAGCCCCTCTTCATCCTCC
         || ||| |  |   ||  |  |    ||   ||  | || |   ||    |||    | |
S78624   GTGGCAGGTTTTTGTTAAGTAAGTCGAAACCATTTAAATTAAATGGCCTTTTCCAATTGC
            6050      6060      6070      6080      6090      6100

270       280       290       300       310       320
MAELO    ACAACTTCCTCCTGACGATCGCGTCC--GGATCGCTGTTGCTCCTGTTCATCGAGAACCT
         | || ||   ||  | |||  ||||   | |  |||  ||| || || | || || ||
S78624   ATAATTTGGTTTTAAC-TTCACTTTCATTGA-CGCTTTTATTGCTTATGGTTGAACAATT
            6110      6120      6130      6140      6150      6160

330       340       350       360       370       380
MAELO    GGTCCCCATCCTCGCCAGAAACGGACTTTTCTACGCCATCTGCGACGACGGTGCCTGGAC
         | || ||  ||  | |    ||||  |||| | |  |||||    | |||||  |||||
S78624   AGTGCCAATTATTGTTCAGCACGGGTTATACTTCGCTATCTGTAATATTGGTGCTTGGAC
            6170      6180      6190      6200      6210      6220

390       400       410       420       430       440
MAELO    CCAGCGCCTCGAGCTCCTCTACTACCTCAACTACCTGGTCAAGTACTGGGAGTTGGCCGA
          |   ||||    |  |||| |  ||| ||   || ||||||||  ||   ||   ||
S78624   TCAACCGCTCGTTACATTATATTACATGAATTACATTGTCAAGTTTATTGAATTTATAGA
            6230      6240      6250      6260      6270      6280

450       460       470       480       490       500
MAELO    CACCGTCTTTTTGGTCCTCAAGAAGAAGCCTCTTGAGTTCCTGCACTACTTCCACCACTC
         ||||  ||   |||||| |||  |||  |  |    ||    |||  |  |||| | |
S78624   CACCTTTTTCTTGGTGCTAAAACATAAAAAATTGACATTTTTGCA-TACTT--ATCA--C
            6290      6300      6310      6320      6330      6340

510       520       530       540       550
MAELO    GATGACCATGGTTCTCTGCTTTTGT----CCAGCTTGGAGGATA-CACTTCAGTGTCCTGG
         ||||   |||  || ||| | |||    || ||||  || ||  || |||  |||||  |||
S78624   CATGGCGCTACTGCCTTATTATGTTACACCCAATTGATGGGCACCACATCTATTTCTTGG
            6350      6360      6370      6380      6390      6400

560       570       580       590       600       610
MAELO    GTCCCTATTACCCTCAACTTGACTGTCCACGTCTTCATGTACTACTACTACATGCGCTCC
         ||||||||| |  |||   ||  ||| ||||  || ||| |||  || |  |    ||
S78624   GTCCCTATTTCATTGAACCTTGGTGTTCACGTGGTTATGTATTGGTACTATT---CTTG
            6410      6420      6430      6440      6450

620       630       640       650       660       670
MAELO    GCTGCC---GGTGTTCGCATCTGGTGGAAGCAGTACTTGACCACTCTCCAGATCGTCCAG
         ||||||   ||  |||  | ||  |||||  |    |||  |||  |  |  ||   |||
S78624   GCTGCCAGAGGCATCAGGGTCTGGTGGAAGGAATGGGTTACCAGATTTCAAATTATCCAA
            6460      6470      6480      6490      6500      6510
```

FIG.9A

```
          680       690       700       710       720       730
MAELO   TTCGTTCTTGACCTCGGATTCATCTACTTCTGCGCCTACACCTACTTCGCCTTCACCTAC
        || |||  | ||   |||| ||||| || ||    | ||||
S78624  TTTGTTTTGGATATCGGTTTCATATATTTTGCTGTCTACCAAAAAGCAGTTCACTTGTAT
        6520      6530      6540      6550      6560      6570
```

FIG.9B

| HOST(PLASMID) | 334(pCGN7875) | | 334(pYES2) | | 334(pYX242) | | 334(pRAE-5) | | 334(pRAE-6) | | 334(pYX242) | | 334(pRAE-5) | |
|---|---|---|---|---|---|---|---|---|---|---|---|---|---|---|
| ADDED SUBSTRATE | 25 μM OA | | 25 μM OA | | 25 μM GLA | | 25 μM GLA | | 25 μM GLA | | NO SUBSTRATE | | NO SUBSTRATE | |
| FATTY ACID | LIPID (μg) | | LIPID (μg) | | LIPID (μg) | | LIPID (μg) | | LIPID (μg) | | LIPID (μg) | | LIPID (μg) | |
| C16:0 | 11.948 | | 23.601 | | 35.123 | | 92.011 | | 85.160 | | 16.294 | | 25.34 | |
| C16:1 | 30.665 | | 71.217 | | 32.789 | | 315.464 | | 115.456 | | 56.183 | | 113.913 | |
| C18:0 | 6.185 | | 9.704 | | 10.515 | | 22.628 | | 18.879 | | 5.535 | | 11.092 | |
| C18:1n-9 | 35.340 | | 57.429 | | 33.989 | | 154.386 | | 106.881 | | 28.388 | | 51.538 | |
| C18:3n-6 | | | | | 48.856 | | 58.084 | | 12.434 | | | | | |
| C20:0 | | | | | 0.474 | | 0.710 | | 0.244 | | | | | |
| C20:1n-9 | (0.375%)* 0.352 | | (0.309%)* 0.527 | | (0.092%)* 0.226 | | 1.405 | | 0.867 | | | | 0.516 | |
| C20:3n-6 | ND | | ND | | | | (0.324%)* 2.504 | | (0.269%)* 1.006 | | ND | | ND | |
| C22:0 | | | | | | | 0.460 | | 0.315 | | | | | |
| C22:1n-9 | | | | | | | 0.321 | | | | | | | |
| C24:0 | | | | | | | | | 1.825 | | | | 0.999 | |
| TOTAL LIPID | 93.760 | | 170.490 | | 245.090 | | 771.690 | | 374.420 | | 112.99 | | 256.52 | |

ND = NOT DETECTED
*% TOTAL FATTY ACID

FIG. 10A

| HOST(PLASMID) | 334(pYX242) | | 334(pYX242) | | 334(pRAE-5) | | 334(pRAE-5) | | 334(pRAE-6) | |
|---|---|---|---|---|---|---|---|---|---|---|
| ADDED SUBSTRATE | 25 μM GLA | | 25 μM GLA | | 25 μM GLA | | 25 μM GLA | | 25 μM GLA | |
| FATTY ACID | LIPID (μg) | | LIPID (μg) | | LIPID (μg) | | LIPID (μg) | | LIPID (μg) | |
| C16:0 | 60.683 | | 61.487 | | 100.998 | | 96.193 | | 66.761 | |
| C16:1 | 79.838 | | 79.586 | | 359.754 | | 220.440 | | 87.359 | |
| C18:0 | 9.784 | | 10.106 | | 15.317 | | 15.165 | | 16.744 | |
| C18:1n-9 | 38.536 | | 39.936 | | 108.472 | | 89.637 | | 71.631 | |
| C18:3n-6 | 17.974 | | 17.833 | | 82.866 | | 56.596 | | 17.766 | |
| C20:0 | | | | | 0.510 | | 0.570 | | | |
| C20:1n-9 | | | | | | | | | | |
| C20:3n-6 | (0.136%)* | 0.389 | (0.130%)* | 0.374 | (0.336%)* | 3.035 | (0.401%)* | 2.689 | (0.353%)* | 1.185 |
| C22:0 | | | | | 0.414 | | 0.383 | | | |
| C22:1n-9 | | | | | | | | | | |
| C24:0 | | | | | 1.513 | | 1.626 | | | |
| TOTAL LIPID | 285.560 | | 288.045 | | 902.560 | | 671.113 | | 335.496 | |

*% TOTAL FATTY ACID

FIG. 10B

| HOST(PLASMID) | 334(pRAE-5/pCGR4) | 334(pYX242/pYES2) | HOST(PLASMID) | 334(pRAE-5/pCGR4) | 334(pYX242/pYES2) |
|---|---|---|---|---|---|
| ADDED SUBSTRATE | 25 μM GLA | 25 μM GLA | ADDED SUBSTRATE | 25 μM GLA | 25 μM GLA |
| FATTY ACID | LIPID (μg) | LIPID (μg) |  | LIPID (μg) | LIPID (μg) |
| C16:0 | 41.050 | 37.169 | C16:0 | 96.986 | 32.221 |
| C16:1 | 99.393 | 100.552 | C16:1n-7 | 209.667 | 62.757 |
| C18:0 | 34.432 | 27.852 | C18:0 | 80.418 | 14.027 |
| C18:1 | 110.631 | 92.786 | C18:1n-9 | 207.104 | 28.701 |
| C18:3n-6 | 15.004 | 7.924 | C18:3n-6 | 25.264 | 10.543 |
| C20:0 | 0.643 | 0.574 | C20:0 | 2.038 |  |
| C20:1 | 1.996 | 1.684 | C20:1n-9 | 3.591 |  |
| C20:3n-6 | 0.542 | 0.607 | C20:3n-6 | 1.284 | 0.326 |
| C20:4n-6 | 0.579 |  | C20:4n-6 | 1.394 |  |
| C22:0 | 1.242 | 2.604 | C22:0 | 1.124 |  |
| C24:0 | 4.754 | 4.563 | C24:0 | 3.952 |  |
| TOTAL LIPID | 334 | 300 | TOTAL LIPID | 756 | 197 |

FIG. 11

| HOST(PLASMID) | 334(pYX242) | | 334(pRAE-5) | | 334(pRELO-1) | | 334(pRELO-2) | |
|---|---|---|---|---|---|---|---|---|
| ADDED SUBSTRATE | 25 μM GLA | | 25 μM GLA | | 25 μM GLA | | 25 μM GLA | |
| | 25°C/48HRS | | 25°C/48HRS | | 25°C/48HRS | | 25°C/48HRS | |
| FATTY ACID | LIPID (μg) | | LIPID (μg) | | LIPID (μg) | | LIPID (μg) | |
| C16:0 | 28.7 | | 76.707 | | 84.424 | | 77.445 | |
| C16:1 | 0.729 | | 2.513 | | 1.532 | | 1.056 | |
| C18:0 | 7.432 | | 15.761 | | 27.17 | | 21.32 | |
| C18:1n-9 | 28.9 | | 77.323 | | 109.419 | | 82.844 | |
| C18:3n-6 | 9.729 | | 29.236 | | 19.085 | | 18.804 | |
| C20:0 | | | 0.643 | | 0.522 | | 0.537 | |
| C20:1n-9 | | | 0.77 | | 0.426 | | 0.299 | |
| C20:3n-6 | (0.185%)* 0.374 | | (0.279%)* 1.472 | | (0.153%)* 0.748 | | (0.200%)* 0.832 | |
| C22:0 | | | 0.451 | | | | | |
| C22:1n-9 | | | | | 0.224 | | | |
| C24:0 | | | 0.918 | | | | | |
| TOTAL LIPID | 202 | | 527 | | 490 | | 416 | |

*% TOTAL FATTY ACID

FIG. 12

```
SCORES      Initl:  156 Initn:  215 Opt:  296
Smith-Waterman score: 296;    28.8% identity in 264 aa overlap 10        20        30        40        50        60
U61954   RTFKMMDQILGTNFTYEGAKEVARGLEGFSAKLAVGYIATIFGLKYYMKDRKAFDLSTPL
                        |  :: |:::|||: ||:: || |: ||
MAELO    AQAYELVTGKSIDSFVFQEGVTPLSTQREVAMWTITYFVVIFGGRQIMKSQDAFKLK-PL
               30        40        50        60        70        80

70        80        90       100       110       119       120
U61954   NIWNGILSTFSLLGFLFTF-PTLLSVIRKDGFSHTYSHVSELYTDSTSGYWI-------F
         | :::| |:: ::|: | :|: :: ::|:            :|:   :| |      :
MAELO    FILHNFLLTIASGSLLLLFIENLVPILARNGL---------FYAICDDGAWTQRLELLYY
               90       100       110                 120       130

130       140       150       160       170
U61954   LWVISKIPELLDTVFIVLRKRPLIFMHWYHHALTGYYALVCYHE--DAVHMVWV-VWMNY
         |  : |  || |||:||:|:|| |:|::||::|    ::|: :    : || : :|
MAELO    LNYLVKYWELADTVFLVLKKKPLEFLHYFHHSMT---MVLCFVQLGGYTSVSWVPITLNL
               140       150       160          170       180       190

180       190       200       210       220       230
U61954   IIHAFMYGYYLLKSLKVPIPPSVAQAITTSQMVQFA-----VAIFAQVHVSYKHYVEGVE
         :|:||| ||: ::   ||  | :|| |:|||:    : : | :: :: ::    : :
MAELO    TVHVFMYYYYMRSAAGVRI--WWKQYLTTLQIVQFVLDLGFIYFCAYTYFAFTYFPWAPN
               200       210         220       230       240       250

240       250       260       270       280
U61954   -GLAYSFRGTAI-GFFMLTTYFYLWIQFYKEHYLKNGGKKYNLAKDQAKTQTKKAN
         |   : :|:|: |  :|::|: |:|:||:  |     : | : ||:::::  | |:
MAELO    VGKCAGTEGAALFGCGLLSSYLLLFINFYRITY----NAKAKAAKERGSNFTPKTVKSGG
               260       270       280            290       300

MAELO    SPKKPSKSKHIX
             310
```

FIG.13

```
SCORES          Initl:  178 Initn:  178 Opt:  318
Smith-Waterman score: 318;   33.0% identity in 188 aa overlap 50        60        70        80        90       100
Z68749     SLLTNQDEVFPHIRARRFIQEHFGLFVQMAIAYVILVFSIKRFMRDREPFQLTTALRLWN
                                   |:|  :::|: :::|:::: |:|    : | |
MAELO      ELVTGKSIDSFVFQEGVTPLSTQREVAMWTITYFVVIFGGRQIMKSQDAFKLKPLFILHN
             30        40        50        60        70        80

110       120       130       140       150       160
Z68749     FFLSVFSIYGSWTMFPF--MVQQIRLYGLYGCGCEALSNLPSQAEYWLFLTILSKAVEFV
           |:|:: |  ||  :: :  :|  :  ||:  |:    :: |  :|: | |  |::
MAELO      FLLTIAS--GSLLLLFIENLVPILARNGLFYAICDD-GAWTQRLELLYYLNYLVKYWELA
             90       100       110       120       130       140

170       180       190       200       210       220
Z68749     DTFFLVLRKKPLIFLHWYHHMATFVFFCSNYPTPSSQSRVGVIVNLFVHAFMYPYYFTRS
           || ||||:||||  |||::||  |:|:    :|  |  : :|| ||:|||·||:   :
MAELO      DTVFLVLKKKPLEFLHYFHHSMTMVLCFVQLGGYTSVSWVPITLNLTVHVFMYYYYMRSA
             150       160       170       180       190       200

230       240       250       260       270
Z68749     MNIKVPAKISMAVTVLQLTQF---MCFIYGCTLMYYSLATNQARYPSNTPATLQCLSYTL
           ::::   |  : :|:||::||   : |||  |:  |::::
MAELO      AGVRIWWK--QYLTTLQIVQFVLDLGFIYFCAYTYFAFTYFPWAPNVGKCAGTEGAALFG
             210       220       230       240       250       260

280
Z68749     HLL

MAELO      CGLLSSYLLLFINFYRITYNAKAKAAKERGSNFTPKTVKSGGSPKKPSKSKHIX
             270       280       290       300       310
```

FIG.14

```
SCORES      Init1:    30 Initn:    30 Opt:    40
Smith-Waterman score: 49;    22.1% identity in 86 aa overlap 10        20        30        40
AF003134              MLYSITRRCYTFFVTSLHFYQLYVTECLENVIFNVLVNGQSINSRWKD
                      |:|:  :   |:|  :   :::  :|:   |:     ::::  :
MAELO     MAAAILDKVNFGIDQPFGIKLDTYFAQA---YELVTGKSIDSFVFQEGVT--PLSTQREV
                 10        20         30        40         50

50        60            70        80        90       100
AF003134  AEKTITSFPFHF-------PQTFFQQPHILTLHFLFFVFVSVTLVTVFKKPKCEFPHSLA
          |  ||| |    |       |  |:   :: ||  ::::::| :|: :|
MAELO     AMWTITYFVVIFGGRQIMKSQDAFKLKPLFILHNFLLTIASGSLLLLFIENLVPILARNG
                60        70        80        90       100       110
```

FIG. 15

Mouse
SCORES      Initl:  161 Initn:  191 Opt:  325
Smith-Waterman score: 325;    28.8% identity in 285 aa overlap

```
                        10        20        30        39        40
U97107                MDTSMNFSRGLKMD--LMQPYDFETFQDLRPFLEEYWVSSF-------LIVV
                      |:|:|   : | |::    |:   |:  :        : ::
MAELO       MAAAILDKVNFGIDQPFGIKLDTYFAQAYELVTGKSIDSFVFQEGVTPLSTQREVAMWTI
                 10        20        30        40        50        60

50        60        70        80        90       100
U97107       VYLLLIVVGQTYMRTRKSFSLQRPLILWSFFLAIFSILGTLRMWKFMATVMFTVGLKQTV
             :|:::|    |:   |:::  :|:|:   :||  :|:|:| |   |:| | :::  | :: :|
MAELO        TYFVVIFGGRQIMKSQDAFKLKPLFILHNFLLTIAS--GSL-LLLFIENLV-PILARNGL
                 70        80        90       100       110

110       120       130       140       150
U97107       CFAIYTDDAVVRFWSFLFLLSKVV---ELGDTAFIILRKRPLIFVHWYHHST--VLLFTS
             :||   | |  ::    :|  |: :|     ||:||:|:::|:|:||   |:::|||  || |::
MAELO        FYAICDDGAWTQRLELLYYLNYLVKYWELADTVFLVLKKKPLEFLHYFHHSMTMVLCFVQ
                 120       130       140       150       160       170

160       170       180       190       200       210
U97107       FGYKNKVPSGGWF-MTMNFGVHSVMYTYYTMKAAKLKHPNLLPMVITSLQILQMVLG---
             :|   ::|    :|     :|:|: ||   ||  ||  :||  ::        : :|:|||:|:||
MAELO        LGGYTSV---SWVPITLNLTVHVFMYYYYMRSAAGVR--IWWKQYLTTLQIVQFVLDLGF
                 180       190       200       210       220       230

220       230       240       250       260
U97107       ------TIFGILNYIWRQEKG-CHTTTEHFFWSFMLYGTYFILFAHFFHRAYLRPKGKVA
                   | |::   : |  : | |    | :::  | ::|::|| :|::  :|    |:|:|
MAELO        IYFCAYTYFAFTYFPWAPNVGKCAGTEGAALFGCGLLSSYLLLFINFYRITY-NAKAHAA
             240       250       260       270       280       290

270
U97107       SKSQX
             ::
MAELO        KERGSNFTPKTVKSGGSPKKPSKSKHIX
                 300       310
```

Human
SCORES      Initl:  147 Initn:  147 Opt:  211
Smith-Waterman score: 211;    28.7% identity in 150 aa overlap

```
                  110       120       130       140       150       160
MAELO        NLVPILARNGLFYAICDDGAWTQRLELLYYLNYLVKYWELADTVFLVLKKKPLEFLHYFH
                             |:||:     :||:|::|:|: |  |||:::|
AC004050                      SLLVVKDLTYLLPLCLPGDTIFIILRKQKLIFLHWYH
                                 10        20        30

170       180       190       200       210       220
MAELO        HSMTMVLCFVQLGGYTSVSWVPITLNLTVHVFMYYYMRSAAGVRIWWK--QYLTTLQIV
             |  :::    : :::   : :::  ||:|| ||||  |||   :|:|  |  :::|  ||:
AC004050     HITVLLYSWYSYKDMVAGGGWFMTMNYGVHAVMYSYYALRAAGFRVSRKFAMFITLSQIT
                 40        50        60        70        80        90

230       240       250       260       270       280
MAELO        QFVLDLGFIYFCAYTYFAFTYFPWAPNVGKCAGTEGAALFGCGLLSSYLLLFINFYRITY
             |:::      |: :|::|      |  :|  :          :::  |||:|| :|:   :|
AC004050     QMLMG------CVVNYLVFC---WMQH-DQCHSHFQNIFWSSLMYLSYLVLFCHFFFEAY
                 100       110       120       130       140
```

FIG.16

```
SCORES        Init1:    87  Initn:  218 Opt:   232
Smith-Waterman score: 272;   29.7% identity in 232 aa overlap 40        50        60        70        80        90
MAELO        SFVFQEGVTPLSTQREVAMWTITYFVVIFGGRQIMKSQDAFKLKPLFILHNFLLTIASGS
                       |:|:   |   |   ::  |:|:  ||:  |
I05465       PRYKSQRMVPPGQLHPYVCLFCYLLTHCMAGTKTTEEPAAVLLPSILQLYNLGLTLLS--
                    20        30        40        50        60        70

100       110       120       130       140       150
MAELO        LLLLFIENLVPILARNGLFYAICDDGAWTQRLELLYYL--NYLVKYWELADTVFLVLKKK
             | :| | :: :   :  |:      :|  : :::: |   |:  |  |:  || |::|:|:
I05465       -LYMFYELVTGVWEGKYNFFCQGTRSAGESDMKIIRVLWWYYFSKLIEFMDTFFFILRKN
                   80        90       100       110       120

160       170       180       190       200       210
MAELO        --PLEFLHYFHH-SMTMVLCFVQLGGYTSVSWVPITLNLTVHVFMYYYY-MRSAAGVR--
              :  || :|| :|  :  ||:     : |:  |||  :||:|| || :  |   ::|
I05465       NHQITVLHVYHHATMLNIWWFVMNWVPCGHSYFGATLNSFIHVLMYSYYGLSSIPSMRPY
               130       140       150       160       170       180

220       230       240       250       260       270
MAELO        IWWKQYLTTLQIVQFVLDLGFIYFCAYTYFAFTYFPWAPNVGKCAGTEGAALFGCGLLSS
             :|||:|:|  |:||||| : :   |:      :::|       |:  |  :|  | : |
I05465       LWWKKYITQGQLVQFVLTI-IQTTCG------VFWP-------CSFPLGWLFFQIGYMIS
                  190       200       210                  220       230

280       290       300       310
MAELO        YLLLFINFYRITYNAKAKAAKERGSNFTPKTVKSGGSPKKPSKSKHIX
              : || ||| ||| |:: : :::
I05465       LIALFTNFYIQTYNKKGASRRKEHLKGHQNGSVAAVNGHTNSFPSLENSVKPRKQRKDXQ
                  240       250       260       270       280       290
```

FIG.17

```
  1  MGTDQGKTFT WEELAAHNTK DDLLLAIRGR VYDVTKFLSR HPGGVDTLLL
 51  GAGRDVTPVF EMYHAFGAAD AIMKKYYVGT LVSNELPIFP EPTVFHKTIK
101  TRVEGYFTDR NIDPKNRPEI WGRYALIFGS LIASYYAQLF VPFVVERTWL
151  QVVFAIIMGF ACAQVGLNPL HDASHFSVTH NPTVWKILGA THDFFNGASY
201  LVWMYQHMLG HHPYTNIAGA DPDVSTSEPD VRRIKPNQKW FVNHINQHMF
251  VPFLYGLLAF KVRIQDINIL YFVKTNDAIR VNPISTWHTV MFWGGKAFFV
301  WYRLIVPLQY LPLGKVLLLF TVADMVSSYW LALTFQANHV VEEVQWPLPD
351  ENGIIQKDWA AMQVETTQDY AHDSHLWTSI TGSLNYQAVH HLFPNVSQHH
401  YPDILAIIKN TCSEYKVPYL VKDTFWQAFA SHLEHLRVLG LRPKEE*
```

FIG.18

| HOST(PLASMID) | 334(MAD708-2) | 334(MAD708-10) | 334(MAD708-18) | 334(MAD708-19) | 334(MAD708-30) | 334(pRAE5) |
|---|---|---|---|---|---|---|
| ADDED SUBSTRATE | 25 μM GLA | 25 μM GLA | 25 μM GLA | 25 μM GLA | 25 μM GLA | 25 μM GLA |
| FATTY ACID | | | % TOTAL LIPID | | | |
| C16:0 | 14.1 | 14.68 | 14.38 | 15.45 | 14.13 | 13.59 |
| C16:1 | 42.84 | 43.42 | 42.57 | 38.03 | 43.58 | 43.98 |
| C18:0 | 3.19 | 3.28 | 3.63 | 4.08 | 3.37 | 2.04 |
| C18:1n-9 | 17.66 | 19.39 | 19.6 | 20.8 | 20.06 | 10.88 |
| C18:3n-6 | 6.65 | 5.58 | 10.24 | 9.46 | 3.56 | 11.14 |
| C20:0 | 0.26 | 0.3 | 0.32 | 0.4 | 0.46 | 0.57 |
| C20:3n-6 | (47.5%) 6.03 | (41.2%) 3.92 | (8.0%) 0.91 | (21.5%) 2.59 | (49%) 3.43 | (3.4%) 0.24 |
| TOTAL LIPID (μg) | 238.47 | 307.86 | 188.51 | 167.31 | 207.47 | 466.65 |
| (% CONVERSION)=PRODUCT/(SUBSTRATE+PRODUCT) | | | | | | |

FIG.20

```
  1 ATGGAGTCGA TTGCGCCATT CCTCCCATCA AAGATGCCGC AAGATCTGTT
 51 TATGGACCTT GCCACCGCTA TCGGTGTCCG GGCCGCGCCC TATGTCGATC
101 CTCTCGAGGC CGCGCTGGTG GCCCAGGCCG AGAAGTACAT CCCCACGATT
151 GTCCATCACA CGCGTGGGTT CCTGGTCGCG GTGGAGTCGC CTTTGGCCCG
201 TGAGCTGCCG TTGATGAACC CGTTCCACGT GCTGTTGATC GTGCTCGCTT
251 ATTTGGTCAC GGTCTTTGTG GGCATGCAGA TCATGAAGAA CTTTGAGCGG
301 TTCGAGGTCA AGACGTTTTC GCTCCTGCAC AACTTTTGTC TGGTCTCGAT
351 CAGCGCCTAC ATGTGCGGTG GGATCCTGTA CGAGGCTTAT CAGGCCAACT
401 ATGGACTGTT TGAGAACGCT GCTGATCATA CCTTCAAGGG TCTTCCTATG
451 GCCAAGATGA TCTGGCTCTT CTACTTCTCC AAGATCATGG AGTTTGTCGA
501 CACCATGATC ATGGTCCTCA AGAAGAACAA CCGCCAGATC TCCTTCTTGC
551 ACGTTTACCA CCACAGCTCC ATCTTCACCA TCTGGTGGTT GGTCACCTTT
601 GTTGCACCCA ACGGTGAAGC CTACTTCTCT GCTGCGTTGA ACTCGTTCAT
651 CCATGTGATC ATGTACGGCT ACTACTTCTT GTCGGCCTTG GGCTTCAAGC
701 AGGTGTCGTT CATCAAGTTC TACATCACGC GCTCGCAGAT GACACAGTTC
751 TGCATGATGT CGGTCCAGTC TTCCTGGGAC ATGTACGCCA TGAAGGTCCT
801 TGGCCGCCCC GGATACCCCT TCTTCATCAC GGCTCTGCTT TGGTTCTACA
851 TGTGGACCAT GCTCGGTCTC TTCTACAACT TTTACAGAAA GAACGCCAAG
901 TTGGCCAAGC AGGCCAAGGC CGACGCTGCC AAGGAGAAGG CAAGGAAGTT
951 GCAGTAA
```

FIG.22

1    MESIAPFLPS KMPQDLFMDL ATAIGVRAAP YVDPLEAALV AQAEKYIPTI

51   VHHTRGFLVA VESPLARELP LMNPFHVLLI VLAYLVTVFV GMQIMKNFER

101  FEVKTFSLLE NFCLVSISAY MCGGILYEAY QANYGLFENA ADHTFKGLPM

151  AKMIWLFYFS KIMEFVDTMI MVLKKNNRQI SFLHVYHHSS IFTIWWLVTF

201  VAPNGEAYFS AALNSFIHVI MYGYYFLSAL GFKQVSFIKF YITRSQMTQF

251  CMMSVQSSWD MYAMKVLGRP GYPFFITALL WFYMWTMLGL FYNFYRKNAK

301  LAKQAKADAA KEKARKLQ*

FIG.23

| HOST(PLASMID) | 334(pRPB2) | 334(pYES2) |
|---|---|---|
| ADDED SUBSTRATE | 25 µM GLA | 25 µM GLA |
| | (n=4) | |
| FATTY ACID | % TOTAL LIPID | |
| C16:0 | 15.65 | 15.23 |
| C16:1 | 35.2 | 38.59 |
| C18:0 | 5.68 | 5.55 |
| C18:1n-9 | 25.55 | 25.27 |
| C18:3n-6 | 3.1 | 6.75 |
| C20:0 | 0.36 | 0.14 |
| C20:3n-6 | (62.0%) 5.06 | (2.6%) 0.18 |
| TOTAL LIPID (µg) | 314 | 247 |

(% CONVERSION)=PRODUCT/(SUBSTRATE+PRODUCT)

FIG.24

| HOST(PLASMID) | 334(pRPB2) | 334(pRPB2) | 334(pRPB2) | 334(pRPB2) | 334(pRPB2) | 334(pRPB2) |
|---|---|---|---|---|---|---|
| ADDED SUBSTRATE | 25 mM SA | 25 mM OA | 25 mM LA | 25 mM DGLA | 25 mM AA | 25 mM ADRENIC |
| | C18:0 | C18:1n-9 | C18:2n-6 | C20:3n-6 | C20:4n-6 | C22:4n-6 |
| FATTY ACID | | | % TOTAL LIPID | | | |
| C16:0 | 15.07 | 14.52 | 15.74 | 15.69 | 16.06 | 15.15 |
| C16:1 | 33.7 | 32.37 | 32.23 | 25.65 | 33.65 | 33.39 |
| C18:0 | *9.78 | 5.83 | 5.61 | 8.33 | 4.52 | 5.35 |
| C18:1n-9 | 31.2 | *37.25 | 26.05 | 20.15 | 24.54 | 28.54 |
| C18:2n-6 | | | *10.4 | | | |
| C18:3n-6 | | | 0.29 | | | |
| C20:2n-6 | | | | | | |
| C20:3n-6 | | | | *16.5 | | |
| C20:4n-6 | | | | 0.27 | *11.7 | |
| C22:4n-6 | | | | | | *7.46 |
| TOTAL LIPID (mg) | 132 | 130 | 171 | 55 | 225 | 163 |

FIG.25A

| HOST(PLASMID) | 334(pRPB2) | 334(pRPB2) | 334(pRPB2) |
|---|---|---|---|
| ADDED SUBSTRATE | 25 μM ALA | 25 μM STA | 25 μM EPA |
|  | C18:3n-3 | C18:4n-3 | C20:5n-3 |
| FATTY ACID | % TOTAL LIPID | | |
| C16:0 | 17.32 | 16.01 | 20.67 |
| C16:1 | 27.68 | 34.31 | 50.7 |
| C18:0 | 6.75 | 5.39 | 6.14 |
| C18:1n-9 | 28.4 | 28.54 | |
| C18:3n-3 | *8.39 | | |
| C18:4n-3 | | *1.95 | |
| C20:4n-3 | | (73.2%) 5.33 | |
| C20:5n-3 | | | *10.33 |
| C22:5n-3 | | | 0.25 |
| TOTAL LIPID (μg) | 114 | 199 | 201 |

*INDICATES SUBSTRATE ADDED
(% CONVERSION)=PRODUCT/(SUBSTRATE+PRODUCT)

FIG.25B

| HOST(PLASMID) | 334(pRPB2+PRPE31) | 334(pYES2+pYX242) |
|---|---|---|
| ADDED SUBSTRATE | 25 μM GLA | 25 μM GLA |
| | | |
| FATTY ACID | % TOTAL LIPID | |
| C16:0 | 15.54 | 18.26 |
| C16:1 | 30.16 | 33.51 |
| C18:0 | 8.76 | 5.58 |
| C18:1n-9 | 27 | 27.37 |
| C18:3n-6 | *2.6 | *5.6 |
| C20:0 | 0.4 | 0.32 |
| C20:3n-6 | (57.4%) 3.55 | (2.9%) 0.17 |
| C20:4n-6 | (27.6%) 1.32 | ND |
| | | |
| TOTAL LIPID (μg) | 254 | 258 |

*INDICATES SUBSTRATE ADDED
(% CONVERSION)=RODUCT/(SUBSTRATE+PRODUCT)

FIG.26A

| HOST(PLASMID) | 334(pRPB2+PRPE31) | 334(pYES2+pYX242) |
|---|---|---|
| ADDED SUBSTRATE | 25 μM STA | 25 μM STA |
| | | |
| FATTY ACID | % TOTAL LIPID | |
| C16:0 | 18 | 16.4 |
| C16:1 | 28.37 | 34.78 |
| C18:0 | 7.42 | 5.71 |
| C18:1n-9 | 26.44 | 30.15 |
| C18:4n-3 | *2.93 | *4.57 |
| C20:0 | 0.25 | 0.17 |
| C20:4n-3 | 4.13 | 0.32 |
| C20:5n-3 | (39%) 1.87 | (2.1%) .10 |
| | | |
| TOTAL LIPID (μg) | 257 | 304 |

*INDICATES SUBSTRATE ADDED
(% CONVERSION)=PRODUCT/(SUBSTRATE+PRODUCT)

FIG.26B

```
SCORES    Initl: 114   Initn: 278   Opt: 278
Smith-Waterman score: 308;   30.9% identity in 259 aa overlap 40        50        60        70        80        90      99
GLELO      VAQAEKYIPTIVHHTRGFLVAVESPLARELPLMNPFHVLLIVLAYLVTVFVGMQIMKNFE
                         ||  :  :|  :  :::|:|::|  |  ||||: :
MAELO      GIKLDTYFAQAYELVTGKSIDSFVFQEGVTPLSTQREVAMWTITYFVVIFGGRQIMKSQD
              20        30        40        50        60        70

100       110       120       130       140       150
GLELO      RFEVKTFSLLHNFCLVSISAYMCGGILYE--AYQANYGLFENAADHTFKGLPMAKMIWLF
           |::| : :||||  |:    |: :    ::  :       |  |||     |    : : :|
MAELO      AFKLKPLFILHNFLLTIASGSLLLLFIENLVPILARNGLFYAICDDGAWTQRLELLYYLN
              80        90       100       110       120       130

160       170       180       190       200       210
GLELO      YFSKIMEFVDTMIMVLKKNNRQISFLHVYHHSSIFTIWWLVTFVAPNGEAYFSAALNSFI
           |: |   |::||:::||||   : : |||  :|||  :  :|  : :  ::   ::    :||  :
MAELO      YLVKYWELADTVFLVLKK--KPLEFLHYFHHS-MTMVLCFVQLGGYTSVSWVPITLNLTV
             140       150         160        170       180       190

220       230       240       250               260
GLELO      HVIMYGYYFLSALGFKQVSFIKFYITRSQMTQF---------CMMSVQS----SWDMYAM
           ||:||  ||: ||  |   :  |  |:|  |::||         |  ::   :       |   :
MAELO      HVFMYYYYMRSAAGVRI--WWKQYLTTLQIVQFVLDLGFIYFCAYTYFAFTYFPWAPNVG
             200       210         220       230       240       250

270       280       290       300       310
GLELO      KVLGRPGYPFFITALLWFYMWTMLGLFYNFYRKNAKLAKQAKADAAKEKARKLQ
           |   |   |  :|  :||    |:      ||  ||||    ::   :|||  ||||::
MAELO      KCAGTEGAALFGCGLLSSYLL----LFINFYR----ITYNAKAKAAKERGSNFTPKTVKS
             260       270           280           290       300

MAELO      GGSPKKPSKSKHIX
             310
```

| | | | |
|---|---|---|---|
| GLELO | 211 | A A L N S F I H V I M Y G Y Y F L S A L G F K Q V S F I K F Y I L R S Q M T Q F C M M | 253 |
| MAELO | 188 | L T N L T V H V F M Y Y Y M R S A A G V R - - I W M K Q Y L U T L Q I V Q F V L D | 228 |
| GNS1 | 204 | L S N L G V H V V M Y W Y F L A A R G I R - - V W M K E W T R F Q I I Q F V L D | 244 |
| SUR4 | 211 | L L N L G V H V I M Y W Y F L S S C G I R - - V W M K Q W T R F Q I I Q F L I D | 251 |
| GLELO | 254 | S V Q S S W D M V A M K V L G R P G Y P F F I T A L L W F Y M W T M L G L F Y N F Y R | 296 |
| MAELO | 229 | L G F I Y F C A V Y F A F T Y F P W - A P N V G K C A G T E G A A L F G C G L L S S | 270 |
| GNS1 | 245 | I G F I Y F A V V Q K A V L Y F P - I L P H C G D V G S T T A T F A G C A I I S S | 286 |
| SUR4 | 252 | L V V Y F A T Y L F Y A H K V L D G I L P N K G T G Y Q A A A Y G Y L L T S | 294 |
| GLELO | 297 | K N A K L A K Q A K A D A A E K A R K L Q | 318 |
| MAELO | 271 | V L L F I N F Y R I T V N A K A A K E R G S N F T P K T V K S G G S P K V P S K | 313 |
| GNS1 | 287 | V L V L F S F Y I N V Y K R K G T K I S R V V K R A H G G V A K V N E Y N V D L | 329 |
| SUR4 | 295 | V L L F I S F Y I Q S V K K G G K K I V K K E S E V S G S V A S G S S T G V R T S N | 337 |
| MAELO | 314 | S K H I | 317 |
| GNS1 | 330 | K N V P T P S P K P Q H R R K R | 347 |
| SUR4 | 338 | T K V S S R K A | 345 |

FIG. 28B

SCORES    Init1: 83    Initn: 186    Opt: 271
Smith-Waterman score: 297;    28.5% identity in 242 aa overlap

```
              30        40        50        60        70        80
MAELO    YELVTGKSIDSFVFQEGVTPLSTQREVAMWTITYFVVIFGGRQIMKSQDAFKLKPLFILH
                       ::  |:::::  |  :  |::::  |:  :  :::::
HS1      STYFKALLGPRDTRVKGWFLLDNYIPTFICSVIYLLIVWLGPKYMRNKQPFSCRGILVVY
              10        20        30        40        50        60

90       100       110       120       130       140
MAELO    NFLLTIASGSLLLLFIENLVPILARNGLFYAICDDGAWTQRLELLYYL--NYLVKYWELA
         |: ||: |    | :| |  ::   :    |:      |  : ::::   |  |: |  |:
HS1      NLGLTLLS---LYMFCELVTGVWEGKYNFFCQGTRTAGESDMKIIRVLWWYYFSKLIEFM
              70        80        90       100       110       120

150       160       170       180       190       200
MAELO    DTVFLVLKK--KPLEFLHYFHH-SMTMVLCFVQLGGYTSVSWVPITLNLTVHVFMYYYY-
         ||  |::|:|  : :   ||:|| ||  :   ||:     : |:    |||  :||:|| ||
HS1      DTFFFILRKNNHQITVLHVYHHASMLNIWWFVMNWVPCGHSYFGATLNSFIHVLMYSYYG
             130       140       150       160       170       180

210       220       230       240       250       260
MAELO    MRSAAGVR--IWWKQYLTTLQIVQFVLDLGFIYFCAYTYFAFTYFPWAPNVGKCAGTEGA
         :  |: ::|   :|||:|:|  |::|||| : :      |:        |  |    |:    |
HS1      LSSVPSMRPYLWWKKYITQGQLLQFVLTI-IQTSCGVI--------W-P----CTFPLGW
             190       200       210       220                   230

270       280       290       300       310
MAELO    ALFGCGLLSSYLLLLFINFYRITYNAKAKAAKERGSNFTPKTVKSGGSPKKPSKSKHI
           |  |  :  |  :  ||  |||   ||| |:  :   ::
HS1      LYFQIGYMISLIALFTNFYIQTYNKKGASRRKDHLKDHQNGSMAAVNGHTNSFSPLENNV
             240       250       260       270       280       290

HS1      KPRKLRKDX
             300
```

FIG.29

SCORES    Init1: 88    Initn: 208    Opt: 272
Smith-Waterman score: 279;    28.2% identity in 266 aa overlap

```
               30        40        50        60        70        80
MAELO    QAYELVTGKSIDSFVFQEGVTPLSTQREVAMWTITYFVVIFGGRQIMKSQDAFKLKPLFI
                         : | :|||: :| | || ::  |:|: ::|
HS2      VNLYQEVMKHADPRIQGYPLMGSPLLMTSILLTYVYFVLSLGPR-IMANRKPFQLRGFMI
               10        20        30        40         50        60

90       100       110       120       130       140
MAELO    LHNFLLTIASGSLLLLFIEN--LVPILAR-NGLFYAICDDGAWTQRLELLYYLNYLVKYW
         ::|| |: |  ::  |: :  |     |  ::|:  ::    |:  |:::    |:
HS2      VYNFSLVALSLYIVYEFLMSGWLSTYTWRCDPVDYSNSPEALRMVRVAWLFLFS---KFI
               70        80        90       100       110       120

150       160       170       180       190
MAELO    ELADTVFLVLKKK--PLEFLHYFHHSMT----MVLCFVQLGGYTSVSWVPITLNLTVHVF
         || |||:::|:||   ||| ||||:        ||: |  :   :| :|||:
HS2      ELMDTVIFILRKKDGQVTFLHVFHHSVLPWSWWWGVKIAPGGMGSFHAM---INSSVHVI
              130       140       150       160       170

200       210       220       230       240
MAELO    MYYYYMRSAAGV----RIWWKQYLTTLQIVQFVL---DLGFIYF---CAYTFAFTYFPW
         || || || |     :|||:::|::|::||||    ::  ||   | | ::  :: |
HS2      MYLYYGLSAFGPVAQPYLWWKKHMTAIQLIQFVLVSLHISQYYFMSSCNYQYPVIIHLIW
              180       190       200       210       220       230

250       260       270       280       290       300
MAELO    APNVGKCAGTEGAAALFGCGLLSSYLLLFINFYRITYNAKAKAAKERGSNFTPKTVKSGGS
         ::|    : :::|| ||: :|:   :    :|  :|  :|
HS2      --------------MYG----TIFFMLFSNFWYHSYTKGKRLPRALQQNGAPGIAKVKAN
                              240       250       260       270

310
MAELO    PKKPSKSKHI

```
SCORES    Init1: 88    Initn: 207   Opt: 223
Smith-Waterman score: 236;    30.4% identity in 191 aa overlap 100       110       120       130       140       150
MAELO    LLLLFIENLVPILARNGLFYAICDDGAWTQRLELLYYLNYLVKYWELADTVFLVLKKKP-
                         |:  : :| :| |   || |||:::|:||
MM2      IVYEFLMSGWLSTYTWRCDPIDFSNSPEALRMVRVAWLFMLSKVIELMDTVIFILRKKDG
              20        30        40        50        60        70

160       170       180       190       200     209
MAELO    -LEFLHYFHHSMTMVLCF----VQLGGYTSVSWVPITLNLTVHVFMYYYYMRSAAGV---
          : ||| ||||:     :     ||: |    :| :||| || ||    || |
MM2      QVTFLHVFHHSVLPWSWWWGIKIAPGGMGSFHAM---INSSVHVVMYLYYGLSALGPVAQ
              80        90       100       110       120       130

210       220       230       240       250       260
MAELO    -RIWWKQYLTTLQIVQFVL---DLGFIYF---CAYTYFAFTYFPWAPNVGKCAGTEGAAL
          :|||:::|::|::||||    ::   ||    | |  :: ::   |                  :
MM2      PYLWWKKHMTAIQLIQFVLSLHISQYYFMPSCNYQYPVIIHLIW-------------M
              140       150       160       170

270       280       290       300       310
MAELO    FGCGLLSSYLLLFINFYRITYNAKAKAAKERGSNFTPKTVKSGGSPKKPSKSKHI
         :|   : :::|| ||:  :|:  :  :   :| :| |:|
MM2      YG----TIFFILFSNFWYHSYTKGKRLPRAVQQNGAPATTKVKAN
              180       190       200       210
```

FIG.31

```
SCORES    Init1: 51    Initn: 115   Opt: 168
Smith-Waterman score: 168;    30.4% identity in 115 aa overlap 30        40        50        60        70        80
MAELO      YELVTGKSIDSFVFQEGVTPLSTQREVAMWTITYFVVIFGGRQIMKSQDAFKLKPLFILH
                ||||::  |:  |  :  ||::  |::|:  ::   |:
AI225632   NAFLDNMFGPRDSRVRGWFLLDSYLPTFILTITYLLSIWLGNKYMKNRPALSLRGILTLY
                20        30        40        50        60        70

90       100       110       120       130       140
MAELO      NFLLTIASGSLLLLFIENLVPILARNGLFYAICDD----GAWTQRLELLYYLNYLVKYWE
           |:  :|:  |:  :|:  :|       :  :|  :     |::       |:   |: | |
AI225632   NLAITLLSAYMLVELI-----LSSWEGGYNLQCQNLDSAGEGDVRVAKVLVWYYFSKLVE
                80        90       100       110       120

150       160       170       180       190       200
MAELO      LADTVFLVLKKK--PLEFLHYFHHSMTMVLCFVQLGGYTSVSWVPITLNLTVHVFMYYYY
           :  ||:|:||:||    :  |||  :||:
AI225632   FLDTIFFVLRKKANQITFLHVYHHASMFNI
                130       140       150
```

FIG.32

SCORES  Frame: (3)  Initl: 332    Initn: 332      Opt: 384
  40.3% identity in 144 aa overlap

```
             80        90       100       110       120       130
GLELO    LIVLAYLVTVFVGMQIMKNFERFEVKTFSLLHNFCLVSISAYMCGGILYEAYQANYGL-F
                                    |:|: :: :|||| : ::  :::::|:|
AI815960                            LYNLGITLLSAYMLAELILSTWEGGYNLQC
                                            10        20        30

140       150       160       170       180       190
GLELO    ENAADHTFKGLPMAKMIWLFYFSKIMEFVDTMIMVLKKNNRQISFLHVYHHSSIFTIWWL
         :: ::     : :||::| :|||| :||:||:::||:|::  ||:||||||:|:|:|||
AI815960 QDLTSAGEADIRVAKVLWWYYFSKSVEFLDTIFFVLRKKTSQITFLHVYHHASMFNIWWC
             40        50        60        70        80        90

200       210       220       230       240       250
GLELO    VTFVAPNGEAYFSAALNSFIHVIMYGYYFLSAL-GFKQVSFIKFYITRSQMTQFCMMSVQ
         |    |  |:::|: :|||||||::||:|| ||::  ::::   : |  |:|:::|::||
AI815960 VLNWIPCGQSFFGPTLNSFIHILMYSYYGLSVFPSMHKYLWWKKYLTQAQLVQF
                    100       110       120       130       140

260       270       280       290       300       310
GLELO    SSWDMYAMKVLGRPGYPFFITALLWFYMWTMLGLFYNFYRKNAKLAKQAKADAAKEKARK
```

FIG.33

SCORES    Init1: 316    Initn: 384    Opt: 477
Smith-Waterman score: 477;    34.2% identity in 240 aa overlap

```
               50        60        70        80        90       100
GLELO    AQAEKYIPTIVHHTRGFLVAVESPLARELPLMNPFHVLLIVLAYLVTVFVGMQIMKNFER
                ||  :::    :  ||:  |::|   :  |:|  :
HS1          MEHFDASLSTYFKALLGPRDTRVKGWFLLDNYIPTFICSVIYLLIVWLGPKYMRNKQP
                 10        20        30        40        50

110       120       130       140       150      159
GLELO    FEVKTFSLLHNFCLVSISAYMCGGILYEAYQANYGLF-ENAADHTFKGLPMAKMIWLFYF
         |  : : :::|: |: :| ||   ::  :::::|::|  :::       : : :::| :||
HS1      FSCRGILVVYNLGLTLLSLYMFCELVTGVWEGKYNFFCQGTRTAGESDMKIIRVLWWYYF
           60        70        80        90       100       110

160       170       180       190       200       210      219
GLELO    SKIMEFVDTMIMVLKKNNRQISFLHVYHHSSIFTIWWLVTFVAPNGEAYFSAALNSFIHV
         ||::||:||::::|:|||:||: ||||||:|:::|||:|    :|  |::||:|:||||||
HS1      SKLIEFMDTFFFILRKNNHQITVLHVYHHASMLNIWWFVMNWVPCGHSYFGATLNSFIHV
           120       130       140       150       160       170

220       230       240       250       260       270
GLELO    IMYGYYFLSAL-GFKQVSFIKFYITRSQMTQFCMMSVQSSWDMYAMKVLGRPGYPFFITA
         :||:||  ||::  :::    :  | |||::|: ||  :  :|:|    |:       :|:
HS1      LMYSYYGLSSVPSMRPYLWWKKYITQGQLLQFVLTIIQTS-----CGVIWPCTFPLGWLY
           180       190       200       210         220       230

280       290       300       310
GLELO    LLWFYMWTMLGLFYNFYRK--NAKLAKQAKADAAKEKARKLQ
           :     ||  ::::||  |||  :   | |  |::  |
HS1      FQIGYMISLIALFTNFYIQTYNKKGASRRKDHLKDHQNGSMAAVNGHTNSFSPLENNVKP
           240       250       260       270       280       290
```

FIG.34

```
SCORES    Init1: 80    Initn: 114    Opt: 178
Smith-Waterman score: 178;    28.8% identity in 146 aa overlap 140       150       160       170       180       190
GLELO     FENAADHTFKGLPMAKMIWLFYFSKIMEFVDTMIMVLKKNNRQISFLHVYHHSSIFTIWW
                                          ||::::|:|   :::  |||  |||  :::     |
AC004050                                  DTIFIILRK--QKLIFLHWYHHITVLLYSW
                                                    10        20

200       210       220       230       240       250
GLELO     LVTFVAPNGEAYFSAALNSFIHVIMYGYYFLSALGFKQVSFIKFYITRSQMTQFCMMSVQ
            | ::|   ::|  :|::||:||  |  |  ||:    : ::|| ||:||:  |   |
AC004050  YSYKDMVAGGGWF-MTMNYGVHAVMYSYYALRAAGFRVSRKFAMFITLSQITQMLMGCVV
           30        40        50        60        70        80

260       270       280       290       300       310
GLELO     SSWDMYAMKVLGRPGYPFFITALLW--FYMWTMLGLFYNFYRKN--AKLAKQAKADAAKE
           :   :  |:    :   |    ::|  :::  :: ||  :|: :     :|:  | :||:
AC004050  NYLVFCWMQ--HDQCHSHF-QNIFWSSLMYLSYLVLFCHFFFEAYIGKMRKTTKAEX
           90        100       110       120       130       140

GLELO     KARKLQ
```

FIG.35

```
SCORES   Init1: 288   Initn: 288   Opt: 399
Smith-Waterman score: 399;   34.6% identity in 211 aa overlap 80        90       100       110       120       130
GLELO   LLIVLAYLVTVFVGMQIMKNFERFEVKTFSLLHNFCLVSISAYMCGGILYEAYQANYGLF
                        :::|| || :| |:    :|: :: ::|
MM2                     IVYNFSLVILSLYIVYEFLMSGWLSTYTWR
                                  10        20        30

140       150       160       170       180       190
GLELO   ENAAD--HTFKGLPMAKMIWLFYFSKIMEFVDTMIMVLKKNNRQISFLHVYHHSSIFTIW
        :  |  :: ::|  |:::  |||::||::|::||:|::|:|:: |::||||:||| :  |
MM2     CDPIDFSNSPEALRMVRVAWLFMLSKVIELMDTVIFILRKKDGQVTFLHVFHHSVLPWSW
           40        50        60        70        80        90

200       210       220       230       240       250
GLELO   WLVTFVAPNGEAYFSAALNSFIHVIMYGYYFLSALGFKQVSFI--KFYITRSQMTQFCMM
        |   :||:|  :  |  :||  :||:||  ||  ||||| ::   |  ::| |: || ::
MM2     WWGIKIAPGGMGSFHAMINSSVHVVMYLYYGLSALGPVAQPYLWWKKHMTAIQLIQFVLV
            100       110       120       130       140       150

260       270       280       290       300       309
GLELO   SVQSSWDMYAMKVLGRPGYPFFITALLWFYMWTMLGLFYNF----YRKNAKLAKQAKADA
        |:: |  ::|  |    :  || :| |:|:|   :: || ||    | |: :| :  :: ::
MM2     SLHIS-QYYFMPSCNYQ-YPVIIH-LIWMYGTIFFFILFSNFWYHSYTKGKRLPRAVQQNG
            160       170       180       190       200

310
GLELO   AKEKARKLQ
              |
MM2     APATTKVKAN
            210
```

FIG.36

```
SCORES   Initl: 160   Initn: 227   Opt: 269
Smith-Waterman score: 269;   35.3% identity in 119 aa overlap 50        60        70        80        90       100         GLELO
         PTIVHHTRGFLVAVESPLARELPLMNPFHVLLIVLAYLVTVFVGMQIMKNFERFEVKTFS
                                      :::::::||::::::|  :  |||    :  ::  :
AI225632    NEVNAFLDNMFGPRDSRVRGWFLLDSYLPTFILTITYLLSIWLGNKYMKNRPALSLRGIL
             10        20        30        40        50        60

110       120       130       140       150       160
GLELO    LLHNFCLVSISAYMCGGILYEAYQANYGLFENAADHTFKG-LPMAK-MIWLFYFSKIMEF
         |:|: :: :||||   ::   :::::|:|   :   | ::| : :|| ::| :||||::||
AI225632    TLYNLAITLLSAYMLVELILSSWEGGYNLQCQNLDSAGEGDVRVAKVLVW-YYFSKLVEF
             70        80        90       100       110       120

170       180       190       200       210       220
GLELO    VDTMIMVLKKNNRQISFLHVYHHSSIFTIWWLVTFVAPNGEAYFSAALNSFIHVIMYGYY
         :||:::||:|: ||:|||||||:|:|:|
AI225632    LDTIFFVLRKKANQITFLHVYHHASMFNI
            130       140       150
```

FIG.37

```
SCORES    Init1: 64    Initn: 129   Opt: 233
Smith-Waterman score: 239;   23.7% identity in 279 aa overlap 20        30        40        50        60        70
GLELO      FMDLATAIGVRAAPYVDPLEAALVAQAEKYIPTIVHHTRGFLVAVESPLAREL-----PL
              : |  :: :||:  :  :|    |      |:
U97107                                   MDTSMNFSRGLKMDLMQPYDFETFQDLRPF
                                             10        20        30

80        90       100       110       120       129
GLELO      MNPFHV--LLIVLAYLVTVFVGMQIMKNFERFEVKTFSLLHNFCLVSISAYMCGGILYEA
           :: : |  :|||::||:  : ||:  |::  :  |  ::    :| :| |: :|  : | ::
U97107     LEEYWVSSFLIVVVYLLLIVVGQTYMRTRKSFSLQRPLILWSFFLAIFS--ILGTLRMWK
               40        50        60        70        80

130       140       150       160       170       180
GLELO      YQAN----YGLFENAADHTFKGLPMAKMIW--LFYFSKIMEFVDTMIMVLKKNNRQISFL
           ::|:     || :::    :    :::: |  || :||::|: || :::|:|  | : |:
U97107     FMATVMFTVGLKQTVCFAIYTDDAVVRF-WSFLFLLSKVVELGDTAFIILRK--RPLIFV
             90       100       110       120       130       140

190       200       210       220       230       240
GLELO      HVYHHSSI--FTIWWLVTFVAPNGEAYFSAALNSFIHVIMYGYYFLSALGFKQVSFIKFY
           | |||::  || :  : | :|  ::: :|  :| :|| ::|  :|: ::: :
U97107     HWYHHSTVLLFTSFGYKNKV-PSGGWFMT--MNFGVHSVMYTYYTMKAAKLKHPNLLPMV
             150       160       170       180       190       200

250       260       270       280       290
GLELO      ITRSQMTQFCMMSVQSSWDMYAMKVLG--RPGYPFFITALLWFYMWTMLGLFYN--FYRK
           ||   |: |: :  :: :   ::   :  |        || : |:  ::: |:: :  |
U97107     ITSLQILQMVLGTIFGILNYIWRQEKGCHTTTEHFFWSFMLYGTYFILFAHFFHRAYLRP
             210       220       230       240       250       260

300       310
GLELO      NAKLAKQAKADAAKEKARKLQ
           ::|:|::::
U97107     KGKVASKSQ
             270
```

FIG.38

```
SCORES    Initl: 100   Initn: 205   Opt: 271
Smith-Waterman score: 271;    30.7% identity in 218 aa overlap 60        70        80        90       100       110
GLELO         TRGFLVAVESPLARELPLMNPFHVLLIVLAYLVTVFVGMQIMKNFERFEVKTFSLLHNFC
                        |:|:||    :|:| : |::       : ||
U68749        ATHGPKNFPDAEGRKFFADHFDVTIQASILYMVVVFGTKWFMRNRQPFQLTIPLNIWNFI
(F56H11.4)         30        40        50        60        70        80

120       130       140       150       160
GLELO         LVSISAYMCGGILYEAYQ--ANYGL---FENAADHTFKGLPMAKMIWLFYFSKIMEFVDT
              |:::|       : |:    || |:   : :: | ||   : :|||: ||::|:|||
U68749        LAAFSIAGAVKMTPEFFGTIANKGIVASYCKVFDFT-KG-ENGYWVWLFMASKLFELVDT
(F56H11.4)         90       100       110       120       130       140

170       180       190       200       210       220
GLELO         MIMVLKKNNRQISFLHVYHHSSIFTIWWLVTFVAPNGEAYFSAALNSFIHVIMYGYYFLS
              :::||:|   | : ||| |||    :   |   ::|| |  ::  || :|:::||:||||
U68749        IFLVLRK--RPLMFLHWYHHILTMIYAWYSHPLTP-GFNRYGIYLNFVVHAFMYSYYFLR
(F56H11.4)        150       160       170       180       190

230       240       250       260       270       280
GLELO         ALGFKQVSFIKFYITRSQMTQFCMMSVQSSWDMYAMKVLGRP-GYPFFITALLWFYMWTM
              :: ::  :||    || |::||  : : :   ||:  :  :  | |:  |:
U68749        SMKIRVPGFIAQAITSLQIVQFIISCAVLAHLGYLMHFTNANCDFEPSVFKLAVFMDTTY
(F56H11.4)    200       210       220       230       240       250

290       300       310
GLELO         LGLFYNFYRKNAKLAKQAKADAAKEKARKLQ
              |:|| ||:
U68749        LALFVNFFLQSYVLRGGKDKYKAVPKKKNN
(F56H11.4)        260       270       280
```

FIG.39

SCORES    Init1: 189    Initn: 264    Opt: 358
Smith-Waterman score: 358;    28.7% identity in 296 aa overlap

```
                  10        20        30        40        50        59
MAELO      MAAAILDKVNFGIDQPFGIKLDTYFAQAYELVTGKSIDSFVFQEGVTPLSTQREVAMW-T
            :::  : :|:||    : :   ::  ::   :|    ||    :: :  :|::  :
U68749        MAQHPLVQRLLDVKFDT---KRFVAIATHGPKNFPDAEGRKFFADHFDVTIQAS
(F56H11.4)         10        20        30        40        50

60        70        80        90       100       110
MAELO      ITYFVVIFGGRQIMKSQDAFKLK-PLFILHNFLLTIASGSLLLLFIENLVPILARNGLFY
           | |:||:||  : :|::::  |:|   || |   ||:|:  |  :   :    :| :|:
U68749     ILYMVVVFGTKWFMRNRQPFQLTIPLNIW-NFILAAFSIAGAVKMTPEFFGTIANKGIVA
(F56H11.4)         60        70        80        90       100       110

120       130       140       150       160       170
MAELO      AICDDGAWTQRLELLYYLNYLV-KYWELADTVFLVLKKKPLEFLHYFHHSMTMVLCFVQL
            :  |     :|:  :    :   :::    |  :||:||:|||||:|:||    |||:  ||: : :
U68749     SYCKVFDFTKGENGYWVWLFMASKLFELVDTIFLVLRKRPLMFLHWYHHILTMIYAWYSH
(F56H11.4)         120       130       140       150       160       170

180       190       200       210       220       230
MAELO      GGYTSVSWVPITLNLTVHVFMY-YYYMRSAAGVRI--WWKQYLTTLQIVQFVLDLGFIYF
            : :   |  ||::||:|||  ||::||   :|:   :  |  :|:|||||||::: : :
U68749     PLTPGFNRYGIYLNFVVHAFMYSYYFLRSMK-IRVPGFIAQAITSLQIVQFIISCAVLAH
(F56H11.4)         180       190       200       210       220

240       250       260       270       280
MAELO      CAYT-YFAFTYFPWAPNVGKCAGTEGAALFGCGLLSSYLLLFINFYRITY-----NAKAK
            :|   :|:  :    :|:| | |     :|   : ::|| ||:||:  :|      : ||
U68749     LGYLMHFTNANCDFEPSVFKLA------VF---MDTTYLALFVNFFLQSYVLRGGKDKYK
(F56H11.4) 230       240       250              260       270       280

290       300       310
MAELO      AAKERGSNFTPKTVKSGGSPKKPSKSKHI
           |: :: :|
U68749     AVPKKKNN
(F56H11.4)
```

FIG. 40

```
SCORES   Init1: 77    Initn: 155   Opt: 264
Smith-Waterman score: 264;   27.2% identity in 206 aa overlap 40        50        60        70        80        90
GLELO     AALVAQAEKYIPTIVHHTRGFLVAVESPLARELPLMNPFHVLLIVLAYLVTVFVGMQIMK
                |:  | |    |:         |::::| |:::|:
DM1       PTKMINMDISVTPNYSYIFDFENDFIHQRTRKWMLENWTWVFYYCGIYMLVIFGGQHFMQ
             10        20        30        40        50        60

100       110       120       130       140       150
GLELO     NFERFEVKTFSLLHNFCLVSISAYMCGGILYEAYQA--NYGLFENAADHTF--KGLPMAK
          |  ||:::    ::  |  |: :| :   :   |  ::  :||||:::   ::  :   :
DM1       NRPRFQLRGPLIIWNTLLAMFSIMGAARTAPELIHVLRHYGLFHSVCVPSYIEQDRVCGF
             70        80        90        100       110       120

160       170       180       190       200       210
GLELO     MIWLFYFSKIMEFVDTMIMVLKKNNRQISFLHVYHHSSIFTIWWLVTFVAPNGEAYFSAA
          ||| :||: |: ||:::||:|   : : ||| |||  :::   |: :::  :: | : :
DM1       WTWLFVLSKLPELGDTIFIVLRK--QPLIFLHWYHHITVLIYSWF-SYTEYTSSARWFIV
             130       140       150       160       170       180

220       230       240       250       260       270
GLELO     LNSFIHVIMYGYYFLSALGFKQVSFIKFYITRSQMTQFCMMSVQSSWDMYAMKVLGRPGY
          :|  :| :||:|| |:|  |:    ||::  ||   |::|:  :  :   |    :|: |
DM1       MNYCVHSVMYSYYALKAARFNPPRFISMIITSLQLAQMIIGCAINVWANGFLKTHGTXSC
             190       200       210       220       230       240

280       290       300       310
GLELO     PFFITALLWFYMWTMLGLFYNFYRKNAKLAKQAKADAAKEKARKLQ

DM1       HISQRNINLSIAMYSSYFVLFARFFYKAYLAPGGHKSRRMA
             250       260       270       280
```

FIG.41

```
SCORES    Init1: 181    Initn: 279   Opt: 328
Smith-Waterman score: 328;    30.0% identity in 237 aa overlap 40        50        60        70        80        90
MAELO    VTGKSIDSFVFQEGVTPLSTQREVAMWTITYFVVIFGGRQIMKSQDAFKLKPLFILHNFL
              |::||||:::|:::  |:|:  :|: | |
DM1      IFDFENDFIHQRTRKWMLENWTWVFYYCGIYMLVIFGGQHFMQNRPRFQLRGPLIIWNTL
           30        40        50        60        70        80

100       110       120       130       140      149
MAELO    LTIASGSLLLLFIENLVPILARNGLFYAICDDGAWTQ-RLELLY-YLNYLVKYWELADTV
         |:: |         :|: :|  : |||:::|  :    | |:  :: :|  | |  ||:||:
DM1      LAMFSIMGAARTAPELIHVLRHYGLFHSVCVPSYIEQDRVCGFWTWLFVLSKLPELGDTI
           90       100       110       120       130       140

150       160       170       180       190       200
MAELO    FLVLKKKPLEFLHYFHHSMTMVLCFVQLGGYTS-VSWVPITLNLTVHVFMYYYYMRSAAG
         |:||:|:|| |||::||  :::  : :   |||  :  |  |::| ||  ||  ||  :||
DM1      FIVLRKQPLIFLHWYHHITVLIYSWFSYTEYTSSARWF-IVMNYCVHSVMYSYYALKAAR
           150       160       170       180       190       200

210       220       230       240       250       260
MAELO    VRI--WWKQYLTTLQIVQFVLDLGFIYFCAYTYFAFTYFPWAPNVGKCAGTEGAALFGCG
           :  ::  :|:||::|:::     ||  : :|    ::    :::|  ::      :: :
DM1      FNPPRFISMIITSLQLAQMIIG-----CAINVWANGFLK-THGTXSCHISQRNINLSIA
           210       220       230       240       250

270       280       290       300       310
MAELO    LLSSYLLLFINFYRITYNAKAKAAKERGSNFTPKTVKSGGSPKKPSKSKHI
         : |||::||    |:   :|   |   :  ::|
DM1      MYSSYFVLFARFFYKAYLAPGGHKSRRMA
           260       270       280
```

FIG.42

```
  1  ATGGAACATT TTGATGCATC ACTTAGTACC TATTTCAAGG CATTGCTAGG
 51  CCCTCGAGAT ACTAGAGTAA AAGGATGGTT TCTTCTGGAC AATTATATAC
101  CCACATTTAT CTGCTCTGTC ATATATTTAC TAATTGTATG GCTGGGACCA
151  AAATACATGA GGAATAAACA GCCATTCTCT TGCCGGGGGA TTTTAGTGGT
201  GTATAACCTT GGACTCACAC TGCTGTCTCT GTATATGTTC TGTGAGTTAG
251  TAACAGGAGT ATGGGAAGGC AAATACAACT TCTTCTGTCA GGGCACACGC
301  ACCGCAGGAG AATCAGATAT GAAGATTATC CGTGTCCTCT GGTGGTACTA
351  CTTCTCCAAA CTCATAGAAT TTATGGACAC TTTCTTCTTC ATCCTGCGCA
401  AGAACAACCA CCAGATCACG GTCCTGCACG TCTACCACCA TGCCTCGATG
451  CTGAACATCT GGTGGTTTGT GATGAACTGG GTCCCCTGCG GCCACTCTTA
501  TTTTGGTGCC ACACTTAATA GCTTCATCCA CGTCCTCATG TACTCTTACT
551  ATGGTTTGTC GTCAGTCCCT TCCATGCGTC CATACCTCTG GTGGAAGAAG
601  TACATCACTC AGGGGCAGCT GCTTCAGTTT GTGCTGACAA TCATCCAGAC
651  CAGCTGCGGG GTCATCTGGC CGTGCACATT CCCTCTTGGT TGGTTGTATT
701  TCCAGATTGG ATACATTATT TCCCTGATTG CTCTCTTCAC AAACTTCTAC
751  ATTCAGACCT ACAACAAGAA AGGGGCCTCC CGAAGGAAAG ACCACCTGAA
801  GGACCACCAG AATGGGTCCG TGGCTGCTGT GAATGGACAC ACCAACAGCT
851  TTCACCCCT GGAAAACAAT GTGAAGCCAA GGAAGCTGCG GAAGGATTGA
901  AGTCAAAGAA TTGA
```

FIG.43

```
  1  MEHFDASLST YFKALLGPRD TRVKGWFLLD NYIPTFICSV IYLLIVWLGP
 51  KYMRNKQPFS CRGILVVYNL GLTLLSLYMF CELVTGVWEG KYNFFCQGTR
101  TAGESDMKII RVLWWYYFSK LIEFMDTFFF ILRKNNHQIT VLHVYHHASM
151  LNIWWFVMNW VPCGHSYFGA TLNSFIHVLM YSYYGLSSVP SMRPYLWWKK
201  YITQGQLLQF VLTIIQTSCG VIWPCTFPLG WLYFQIGYII SLIALFTNFY
251  IQTYNKKGAS RRKDHLKDHQ NGSVAAVNGH TNSFSPLENN VKPRKLRKD*
```

FIG.44

| HOST(PLASMID) | 334(pYX242) | | 334(pRAE-58-A1) | | 334(pYX242) | | 334(pRAE-58-A1) | |
|---|---|---|---|---|---|---|---|---|
| ADDED SUBSTRATE | 25 μM GLA | | 25 μM GLA | | 25 μM AA | | 25 μM AA | |
| FATTY ACID | % TOTAL FATTY ACID | | % TOTAL FATTY ACID | | % TOTAL FATTY ACID | | % TOTAL FATTY ACID | |
| C18:3n-6 | 4.40 | | 2.71 | | 0.03 | | 0.04 | |
| C20:3n-6 | 0.09 | | (50.34%)* 2.75 | | 0.02 | | 0.02 | |
| C20:4n-6 | | | | | 7.48 | | 3.97 | |
| C224n-6 | | | | | ND | | (23.37%)* 1.21 | |
| C16:1n-7 | 41.11 | | 34.72 | | 41.49 | | 35.07 | |
| C18:1n-7 | 1.85 | | 11.33 | | 2.01 | | 11.57 | |
| C20:1n-7 | 0.04 | | 1.48 | | 0.04 | | 1.62 | |
| C18:1n-9 | 15.60 | | 15.66 | | 15.16 | | 14.57 | |
| C20:1n-9 | 0.06 | | 0.22 | | 0.06 | | 0.23 | |
| C18:1n-5 | 0.11 | | 0.62 | | 0.12 | | 0.58 | |
| TOTAL LIPID | 370 | | 969 | | 359 | | 514 | |

*% CONVERSION=PRODUCT/(SUBSTRATE+PRODUCT)

FIG.45

```
  1  ATGGCTCAGC ATCCGCTCGT TCAACGGCTT CTCGATGTCA AATTCGACAC
 51  GAAACGATTT GTGGCTATTG CTACTCATGG GCCAAAGAAT TTCCCTGACG
101  CAGAAGGTCG CAAGTTCTTT GCTGATCACT TTGATGTTAC TATTCAGGCT
151  TCAATCCTGT ACATGGTCGT TGTGTTCGGA ACAAAATGGT TCATGCGTAA
201  TCGTCAACCA TTCCAATTGA CTATTCCACT CAACATCTGG AATTTCATCC
251  TCGCCGCATT TTCCATCGCA GGAGCTGTCA AAATGACCCC AGAGTTCTTT
301  GGAACCATTG CCAACAAAGG AATTGTCGCA TCCTACTGCA AAGTGTTTGA
351  TTTCACGAAA GGAGAGAATG GATACTGGGT GTGGCTCTTC ATGGCTTCCA
401  AACTTTTCGA ACTTGTTGAC ACCATCTTCT TGGTTCTCCG TAAACGTCCA
451  CTCATGTTCC TTCACTGGTA TCACCATATT CTCACCATGA TCTACGCCTG
501  GTACTCTCAT CCATTGACCC CAGGATTCAA CAGATACGGA ATTTATCTTA
551  ACTTTGTCGT CCACGCCTTC ATGTACTCTT ACTACTTCCT TCGCTCGATG
601  AAGATTCGCG TGCCAGGATT CATCGCCCAA GCTATCACAT CTCTTCAAAT
651  CGTTCAATTC ATCATCTCTT GCGCCGTTCT TGCTCATCTT GGTTATCTCA
701  TGCACTTCAC CAATGCCAAC TGTGATTTCG AGCCATCAGT ATTCAAGCTC
751  GCAGTTTTCA TGGACACAAC ATACTTGGCT CTTTTCGTCA ACTTCTTCCT
801  CCAATCATAT GTTCTCCGCG AGGAAAAGA CAAGTACAAG GCAGTGCCAA
851  AGAAGAAGAA CAACTAA
```

FIG.46

```
  1 MAQHPLVQRL LDVKFDTKRF VAIATHGPKN FPDAEGRKFF ADHFDVTIQA
 51 SILYMVVVFG TKWFMRNRQP FQLTIPLNIW NFILAAFSIA GAVKMTPEFF
101 GTIANKGIVA SYCKVFDFTK GENGYWVWLF MASKLFELVD TIFLVLRKRP
151 LMFLHWYHHI LTMIYAWYSH PLTPGFNRYG IYLNFVVHAF MYSYYFLRSM
201 KIRVPGFIAQ AITSLQIVQF IISCAVLAHL GYLMHFTNAN CDFEPSVFKL
251 AVFMDTTYLA LFVNFFLQSY VLRGGKDKYK AVPKKKNN
```

FIG.47

| HOST(PLASMID) | 334(pYX242) | | 334(pRET-21) | | 334(pRET-22) | |
|---|---|---|---|---|---|---|
| ADDED SUBSTRATES | 50 μM GLA + 50 μM AA | | 50 μM GLA + 50 μM AA | | 50 μM GLA + 50 μM AA | |
| FATTY ACID | % TOTAL FATTY ACID | | % TOTAL FATTY ACID | | % TOTAL FATTY ACID | |
| C16:0 | 9.22 | | 12.46 | | 9.9 | |
| C16:1 | 0.09 | | 0.18 | | 0.13 | |
| C18:0 | 1.46 | | 2.41 | | 1.49 | |
| C18:1n-9 | 4.03 | | 4.92 | | 3.91 | |
| C18:3n-6 | 10.02 | | 11.89 | | 8.69 | |
| C20:3n-6 | 0.13 | (1.28%)* | 1.48 | (11.1%)* | 2.09 | (19.4%)* |
| C20:4n-6 | 46.98 | | 28.87 | | 35.25 | |
| C20:4n-6 | 0 | | 0 | | 0 | |
| TOTAL LIPID (mg) | 212 | | 174 | | 187 | |
| *% CONVERSION=PRODUCT/(SUBSTRATE+PRODUCT) | | | | | | |

FIG. 48

```
  1  ATGAACATGT CAGTGTTGAC TTTACAAGAA TATGAATTCG AAAAGCAGTT
 51  CAACGAGAAT GAAGCCATCC AATGGATGCA GGAAAACTGG AAGAAATCTT
101  TCCTGTTTTC TGCTCTGTAT GCTGCCTTTA TATTCGGTGG TCGGCACCTA
151  ATGAATAAAC GAGCAAAGTT TGAACTGAGG AAGCCATTAG TGCTCTGGTC
201  TCTGACCCTT GCAGTCTTCA GTATATTCGG TGCTCTTCGA ACTGGTGCTT
251  ATATGGTGTA CATTTTGATG ACCAAAGGCC TGAAGCAGTC AGTTTGTGAC
301  CAGGGTTTTT ACAATGGACC TGTCAGCAAA TTCTGGGCTT ATGCATTTGT
351  GCTAAGCAAA GCACCCGAAC TAGGAGATAC AATATTCATT ATTCTGAGGA
401  AGCAGAAGCT GATCTTCCTG CACTGGTATC ACCACATCAC TGTGCTCCTG
451  TACTCTTGGT ACTCCTACAA AGACATGGTT GCCGGGGGAG GTTGGTTCAT
501  GACTATGAAC TATGGCGTGC ACGCCGTGAT GTACTCTTAC TATGCCTTGC
551  GGGCGGCAGG TTTCCGAGTC TCCCGGAAGT TGCCATGTT CATCACCTTG
601  TCCCAGATCA CTCAGATGCT GATGGGCTGT GTGGTTAACT ACCTGGTCTT
651  CTGCTGGATG CAGCATGACC AGTGTCACTC TCACTTTCAG AACATCTTCT
701  GGTCCTCACT CATGTACCTC AGCTACCTTG TGCTCTTCTG CCATTTCTTC
751  TTTGAGGCCT ACATCGGCAA AATGAGGAAA ACAACGAAAG CTGAATAG
```

FIG.49

```
  1  MNMSVLTLQE YEFEKQFNEN EAIQWMQENW KKSFLFSALY AAFIFGGRHL
 51  MNKRAKFELR KPLVLWSLTL AVFSIFGALR TGAYMVYILM TKGLKQSVCD
101  QGFYNGPVSK FWAYAFVLSK APELGDTIFI ILRKQKLIFL HWYHHITVLL
151  YSWYSYKDMV AGGGWFMTMN YGVHAVMYSY YALRAAGFRV SRKFAMFITL
201  SQITQMLMGC VVNYLVFCWM QHDQCHSHFQ NIFWSSLMYL SYLVLFCHFF
251  FEAYIGKMRK TTKAE*
```

FIG.50

ELONGASE GENES AND USES THEREOF

The present application is a divisional of U.S. patent application Ser. No. 09/379,095, filed Aug. 23, 1999, abandoned Jun. 16, 2003, herein incorporated in its entirety by reference.

BACKGROUND OF THE INVENTION

1. Technical Field

The subject invention relates to the identification of several genes involved in the elongation of long-chain polyunsaturated fatty acids (i.e., "elongases") and to uses thereof. In particular, the elongase enzyme is utilized in the conversion of one fatty acid to another. For example, elongase catalyzes the conversion of gamma linolenic acid (GLA) to dihomo-γ-linolenic acid (DGLA, 20:3n-6) and the conversion of stearidonic acid (STA, 18:4n-3) to (n-3)-eicosatetraenoic acid (20:4n-3). Elongase also catalyzes the conversion of arachidonic acid (AA, 20:4n-6) to adrenic acid (ADA, 22:4n-6), the conversion of eicosapentaenoic acid (EPA, 20:5n-3) to ω3-docosapentaenoic acid (22:5n-3), and the conversation of α-linolenic acid (ALA, 18:3n-3) to 20:3n-3. DGLA, for example, may be utilized in the production of other polyunsaturated fatty acids (PUFAs), such as arachidonic acid (AA) which may be added to pharmaceutical compositions, nutritional compositions, animal feeds, as well as other products such as cosmetics.

2. Background Information

The elongases which have been identified in the past differ in terms of the substrates upon which they act. Furthermore, they are present in both animals and plants. Those found in mammals have the ability to act on saturated, monounsaturated and polyunsaturated fatty acids. In contrast, those found in plants are specific for saturated or monounsaturated fatty acids. Thus, in order to generate polyunsaturated fatty acids in plants, there is a need for a PUFA-specific elongase.

In both plants and animals, the elongation process is believed to be the result of a four-step mechanism (Lassner et al., *The Plant Cell* 8:281–292 (1996)). CoA is the acyl carrier. Step one involves condensation of malonyl-CoA with a long-chain acyl-CoA to yield carbon dioxide and a β-ketoacyl-CoA in which the acyl moiety has been elongated by two carbon atoms. Subsequent reactions include reduction to β-hydroxyacyl-CoA, dehydration to an enoyl-CoA, and a second reduction to yield the elongated acyl-CoA. The initial condensation reaction is not only the substrate-specific step but also the rate-limiting step.

As noted previously, elongases, more specifically, those which utilize PUFAs as substrates, are critical in the production of long-chain polyunsaturated fatty acids which have many important functions. For example, PUFAs are important components of the plasma membrane of a cell where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, efficiently.

A number of enzymes are involved in PUFA biosynthesis including elongases (elo) (see FIG. 1). For example, linoleic acid (LA, 18:2-Δ9,12 or 18:2n-6) is produced from oleic acid (OA, 18:1-Δ9 or 18:1n-9) by a Δ12 desaturase. GLA (18:3-Δ6, 9,12) is produced from linoleic acid by a Δ6-desaturase. AA (20:4-Δ5,8,11,14) is produced from dihomo-γ-linolenic acid (DGLA, 20:3-Δ8,11,14) by a Δ5-desaturase. As noted above, DGLA is produced from GLA by an elongase.

It must be noted that animals cannot desaturate beyond the Δ9 position and therefore cannot convert oleic acid into linoleic acid. Likewise, α-linolenic acid (ALA, 18:3-Δ9,12, 15 or 18:3n-3) cannot be synthesized by mammals, since they lack Δ15 desaturase activity. However, α-linolenic acid can be converted to stearidonic acid (STA, 18:4-Δ6,9,12,15) by a Δ6-desaturase (see PCT publication WO 96/13591; see also U.S. Pat. No. 5,552,306), followed by elongation to (n-3)-eicosatetraenoic acid (20:4-Δ8,11,14,17 or 20:4n-3) in mammals and algae. This polyunsaturated fatty acid (i.e., 20:4-Δ8,11,14,17) can then be converted to eicosapentaenoic acid (EPA, 20:5-Δ5,8,11,14,17) by a Δ5-desaturase. Other eukaryotes, including fungi and plants, have enzymes which desaturate at carbons 12 (see PCT publication WO 94/11516 and U.S. Pat. No. 5,443,974) and 15 (see PCT publication WO 93/11245). The major polyunsaturated fatty acids of animals therefore are either derived from diet and/or from desaturation and elongation of linoleic acid or α-linolenic acid. In view of the inability of mammals to produce these essential long chain fatty acids, it is of significant interest to isolate genes involved in PUFA biosynthesis from species that naturally produce these fatty acids and to express these genes in a microbial, plant or animal system which can be altered to provide production of commercial quantities of one or more PUFAs. Consequently, there is a definite need for the elongase enzyme, the gene encoding the enzyme, as well as recombinant methods of producing this enzyme. Additionally, a need exists for oils containing levels of PUFA beyond those naturally present as well as those enriched in novel PUFAs. Such oils can only be made by isolation and expression of the elongase gene.

One of the most important long chain PUFAs, noted above, is arachidonic acid (AA). AA is found in filamentous fungi and can also be purified from mammalian tissues including the liver and the adrenal glands. As noted above, AA production from DGLA is catalyzed by a Δ5-desaturase, and DGLA production from γ-linolenic acid (GLA) is catalyzed by an elongase. However, until the present invention, no elongase had been identified which was active on substrate fatty acids in the pathways for the production of long chain PUFAs and, in particular, AA, eicosapentaenoic acid (EPA), adrenic acid, docosahexaenoic acid (DHA, 22:6n-3), ω3-docosapentaenoic acid (22:5n-3) or ω6-docosapentaenoic acid (22:5n-6).

Two genes appeared to be of interest in the present search for the elongase gene. In particular, the jojoba β-ketoacyl-coenzyme A synthase (KCS), or jojoba KCS (GenBank Accession # U37088), catalyzes the initial reaction of the fatty acyl-CoA elongation pathway (i.e., the condensation of malonyl-CoA with long-chain acyl-CoA (Lassner et al., *The Plant Cell* 8:281–292 (1996)). Jojoba KCS substrate preference is 18:0, 20:0, 20:1, 18:1, 22:1, 22:0 and 16:0. *Saccharomcyes cerevisiae* elongase (ELO2) also catalyzes the conversion of long chain saturated and monounsaturated fatty acids, producing high levels of 22:0, 24:0, and also 18:0, 18:1, 20:0, 20:1, 22:0, 22:1, and 24:1 (Oh et al., *The Journal of Biological Chemistry* 272 (28):17376–17384 (1997); see also U.S. Pat. No. 5,484,724 for a nucleotide sequence which includes the sequence of ELO2; see PCT publication WO 88/07577 for a discussion of the sequence of a glycosylation inhibiting factor which is described in Example V). The search for a long chain PUFA-specific elongase in *Mortierella alpina* began based upon a review of the homologies shared between these two genes and by expression screening for PUFA-elongase activity.

SUMMARY OF THE INVENTION

The present invention relates to an isolated nucleotide sequence corresponding to or complementary to at least about 50% of the nucleotide sequence shown in SEQ ID NO:1 (FIG. 6). This isolated sequence may be represented by SEQ ID NO:1. The sequence encodes a functionally active elongase which utilizes a polyunsaturated fatty acid or a monounsaturated fatty acid as a substrate. In particular, the sequence may be derived from a fungus of the genus *Mortierella* and may specifically be isolated from *Mortierella alpina*.

The present invention also includes a purified protein encoded by the above nucleotide sequence as well as a purified polypeptide which elongates polyunsaturated fatty acids or monounsaturated fatty acids and has at least about 50% amino acid similarity to the amino acid sequence of the purified protein encoded by the above nucleotide sequence.

Additionally, the present invention encompasses a method of producing an elongase enzyme comprising the steps of: a) isolating the nucleotide sequence represented by SEQ ID NO:1 (FIG. 6); b) constructing a vector comprising: i) the isolated nucleotide sequence operably linked to ii) a promoter; and c) introducing the vector into a host cell under time and conditions sufficient for expression of the elongase enzyme. The host cell may be a eukaryotic cell or a prokaryotic cell.

The prokaryotic cell may be, for example an *E. coli* cell, a cyanobacterial cell, or a *B. subtilis* cell. The eukaryotic cell may be, for example, a mammalian cell, an insect cell, a plant cell or a fungal cell. The fungal cell may be, for example, *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. or *Pichia* spp. In particular, the fungal cell may be a yeast cell such as *Saccharomyces* spp., in particular, *Saccharomyces cerevisiae*, *Candida* spp., *Hansenula* spp. or *Pichia* spp.

The invention also includes a vector comprising: a) a nucleotide sequence as represented by SEQ ID NO: 1 (FIG. 6) operably linked to b) a promoter, as well as a host cell comprising this vector. The host may be a prokaryotic cell or a eukaryotic cell. Suitable examples of prokaryotic cells include *E. coli*, Cyanobacteria, and *B. subtilis* cells. Suitable examples of eukaryotic cells include a mammalian cell, an insect cell, a plant cell and a fungal cell. The fungal cell may be, for example, *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. In particular, the fungal cell may be, for example, a yeast cell such as, for example, *Saccharomyces* spp., in particular, *Saccharomyces cerevisiae*, *Candida* spp., *Hansenula* spp. and *Pichia* spp.

The present invention includes a plant cell, plant or plant tissue comprising the above-described vector, wherein expression of the nucleotide sequence of the vector results in production of at least one fatty acid selected from the group consisting of a monounsaturated fatty acid and a polyunsaturated fatty acid by the plant cell, plant or plant tissue. The polyunsaturated fatty acid may be, for example, dihomo-γ-linolenic acid (DGLA), 20:4n-3, and adrenic acid (ADA). The invention also includes one or more plant oils or fatty acids expressed by the plant cell, plant or plant tissue. Additionally, the present invention encompasses a transgenic plant comprising the above-described vector, wherein expression of the nucleotide sequence of the vector results in production of a polyunsaturated fatty acid in seeds of the transgenic plant.

Furthermore, the present invention includes a transgenic, non-human mammal whose genome comprises a DNA sequence encoding an elongase operably linked to a promoter. The DNA sequence may be represented by SEQ ID NO:1 (FIG. 6). The present invention also includes a fluid (e.g., milk) produced by the transgenic, non-human wherein (e.g., milk) the fluid comprises a detectable level of at least one elongase or products thereof such as, for example, DGLA, ω6-docosapentaenoic acid, ADA and/or 20:4n-3 (see FIG. 1).

Additionally, the present invention includes a method for producing a polyunsaturated fatty acid comprising the steps of: a) isolating said nucleotide sequence represented by SEQ ID NO:1 (FIG. 6); b) constructing a vector comprising the isolated nucleotide sequence; c) introducing the vector into a host cell under time and conditions sufficient for expression of elongase enzyme encoded by the isolated nucleotide sequence; and d) exposing the expressed elongase enzyme to a "substrate" polyunsaturated fatty acid in order to convert the substrate to a "product" polyunsaturated fatty acid. The substrate polyunsaturated fatty acid may be selected from the group consisting of, for example, linolenic acid (GLA), stearidonic acid (STA) and arachidonic acid (AA), and the product polyunsaturated fatty acid may be selected from the group consisting of, for example, DGLA, 20:4n-3, and ADA, respectively. The method may further comprise the step of exposing the product polyunsaturated fatty acid to at least one desaturase in order to convert the product polyunsaturated fatty acid to "another" polyunsaturated fatty acid. The product polyunsaturated fatty acid may be selected from the group consisting of, for example, DGLA, 20:4n-3, and ADA. The another polyunsaturated fatty acid may be selected from the group consisting of, for example, AA, eicosapentaenoic acid (EPA), ω6-docosapentaenoic acid, respectively, and the at least one desaturase is Δ5-desaturase, with respect to production of AA or EPA, and Δ4-desaturase, with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a "final" polyunsaturated fatty acid. The final polyunsaturated fatty acid may be, for example, docosahexaenoic acid (DHA), AA, ω6-docosapentaenoic acid, or ω3-docosapentaenoic acid.

Also, the present invention includes a nutritional composition comprising at least one polyunsaturated fatty acid selected from the group consisting of the product polyunsaturated fatty acid produced according to the above-described method, the another polyunsaturated fatty acid produced according to the above-described method, and the final polyunsaturated fatty acid produced according to the above-described method. The product polyunsaturated fatty acid may be selected from the group consisting of, for example, DGLA, 20:4n-3 and ADA. The another polyunsaturated fatty acid may be, for example, AA, EPA, or ω6-docosapentaenoic acid. The final polyunsaturated fatty acid may be, for example, DHA, adrenic acid, ω6-docosapentaenoic acid or ω3-docosapentaenoic acid. The nutritional composition may be, for example, an infant formula, a dietary supplement or a dietary substitute and may be administered to a human or an animal and may be administered enterally or parenterally. The nutritional composition may further comprise at least one macronutrient selected from the group consisting of coconut oil, soy oil, canola oil, monoglycerides, diglycerides, triglycerides, glucose, edible lactose, electrodialysed whey, electrodialysed skim milk, milk whey, soy protein, protein hydrolysates, sunflower oil, safflower oil, corn oil, and flax oil. It may also comprise at least one vitamin selected from the group consisting of Vitamins A, C, D, E, and B complex and at least one mineral selected from the group consisting of calcium magnesium, zinc, manganese, sodium, potassium, phosphorus, copper, chloride, iodine, selenium and iron.

Additionally, the present invention encompasses a pharmaceutical composition comprising 1) at least one polyunsaturated fatty acid selected from the group consisting of the product polyunsaturated fatty acid produced according to the above-described method, the another polyunsaturated fatty acid produced according to the above-described method of claim 32, and the final polyunsaturated fatty acid produced according to the above-described method and 2) a pharmaceutically acceptable carrier. The composition may be administered to a human or an animal. It may also further comprise at least one element selected from the group consisting of a vitamin, a mineral, a salt, a carbohydrate, an amino acid, a free fatty acid, a preservative, an excipient, an anti-histamine, a growth factor, an antibiotic, a diluent, a phospholipid, an antioxidant, and a phenolic compound. It may be administered enterally, parenterally, topically, rectally, intramuscularly, subcutaneously, intradermally, or by any other appropriate means.

The present invention also includes an animal feed comprising at least one polyunsaturated fatty acid selected from the group consisting of the product polyunsaturated fatty acid produced according to the above-described method, the another polyunsaturated fatty acid produced according to the above-described method, and the final polyunsaturated fatty acid produced according to the above-described method. The product polyunsaturated fatty acid may be, for example, DGLA, 20:4n-3, and ADA. The another polyunsaturated fatty acid may be, for example, AA, EPA, or ω6-docosapentaenoic acid. The final polyunsaturated fatty acid may be, for example, DHA, adrenic acid, ω6-docosapentaenoic acid or ω3-docosapentaenoic acid.

Moreover, the present invention also includes a cosmetic comprising a polyunsaturated fatty acid selected from the group consisting of the product polyunsaturated fatty acid produced according to the above-described method, the another polyunsaturated fatty acid produced according to the above-described method, and the final polyunsaturated fatty acid produced according to the above-described method.

Additionally, the present invention includes a method of preventing or treating a condition caused by insufficient intake or production of polyunsaturated fatty acids comprising administering to the patient the above nutritional composition in an amount sufficient to effect prevention or treatment.

The present invention also includes an isolated nucleotide sequence corresponding to or complementary to at least about 35% of the nucleotide sequence shown in SEQ ID NO:2 (FIG. 22). This sequence may be represented by SEQ ID NO:2. The sequence encodes a functionally active elongase which utilizes a polyunsaturated fatty acid as a substrate. This sequence may also be derived, for example, from a fungus of the genus *Mortierella*. In particular, it may be derived from *M. alpina*.

Additionally, the present invention includes a purified protein encoded by the above nucleotide sequence as well as a purified polypeptide which elongates polyunsaturated fatty acids and has at least about 30% amino acid similarity to the amino acid sequence of the purified protein.

The present invention also includes a method of producing an elongase enzyme as described above. The sequence inserted in the vector is represented by SEQ ID NO:2 (FIG. 22). The host cell may be prokaryotic or eukaryotic. Suitable examples are described above.

The present invention also includes a vector comprising: a) a nucleotide sequence as represented by SEQ ID NO:2 (FIG. 22) operably linked to b) a promoter, as well as a host cell comprising this vector. Again, the host cell may be eukaryotic or prokaryotic. Suitable examples are described above.

The invention also includes a plant cell, plant or plant tissue comprising the above vector, wherein expression of the nucleotide sequence of the vector results in production of a polyunsaturated fatty acid by the plant cell, plant or plant tissue. The polyunsaturated fatty acid may be, for example, DGLA, 20:4n-3, or ADA. Additionally, the invention includes one or more plant oils or fatty acids expressed by the plant cell, plant or plant tissue.

Furthermore, the present invention also includes a transgenic plant comprising the above vector, wherein expression of the nucleotide sequence (SEQ ID NO:2) of the vector results in production of a polyunsaturated fatty acid in seeds of the transgenic plant.

The invention also includes a transgenic, non-human mammal whose genome comprises a DNA sequence (SEQ ID NO:2) encoding an elongase operably linked to a promoter. The invention also includes a fluid produced by this transgenic, non-human mammal wherein the fluid comprises a detectable level of at least one elongase or products thereof.

The present invention also includes a method for producing a polyunsaturated fatty acid comprising the steps of: a) isolating the nucleotide sequence represented by SEQ ID NO:2 (FIG. 22); b) constructing a vector comprising the isolated nucleotide sequence; c) introducing the vector into a host cell under time and conditions sufficient for expression of an elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA, or AA, the product polyunsaturated fatty acid may be, for example, DGLA, 20:4n-3, or ω6-docosapentaenoic acid, respectively.

The method may further comprise the step of exposing the expressed elongase enzyme to at least one desaturase in order to convert the product polyunsaturated fatty acid to another polyunsaturated fatty acid. The product polyunsaturated fatty acid may be, for example, DGLA, 20:4n-3, or ADA, the another polyunsaturated fatty acid may be, for example, AA, EPA, or ω6-docosapentaenoic acid, respectively, and the at least one desaturase is Δ5-desaturase with respect to production of AA or EPA, and Δ4-desaturase with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, docosahexaenoic acid, AA, ω6-docosapentaenoic acid, or ω3-docosapentaenoic acid.

The invention also includes a nutritional composition comprising at least one polyunsaturated fatty acid selected from the product polyunsaturated fatty acid produced according to the method described with respect to SEQ ID NO:2, the another polyunsaturated fatty acid produced according to the method described with respect to SEQ ID NO:2, and the final polyunsaturated fatty acid produced according to the method described with respect to SEQ ID NO:2. The product polyunsaturated fatty acid may be selected from the group consisting of, for example, DGLA, 20:4n-3 and ADA. The another polyunsaturated fatty acid may be selected from the group consisting of, for example, AA, EPA, and ω6-docosapentaenoic acid. The final polyunsaturated fatty acid may be selected from the group consisting of, for example, DHA, AA, ω6-docosapentaenoic acid, and ω3-docosapentaenoic acid.

The other attributes of the composition are the same as those described above with respect to administration, characterization, components, etc.

The present invention also includes a pharmaceutical composition comprising 1) at least one polyunsaturated fatty acid selected from the group consisting of the product polyunsaturated fatty acid produced according to the method of noted above with respect to SEQ ID NO:2, the another polyunsaturated fatty acid produced according to the method described above with respect to SEQ ID NO:2, and the final polyunsaturated fatty acid produced according to the method described above with respect to SEQ ID NO:2, and 2) a pharmaceutically acceptable carrier. The characteristics of the above-described pharmaceutical composition (e.g., administration, components, etc.) also apply to this composition.

The present invention also includes an animal feed comprising at least one polyunsaturated fatty acid selected from the group consisting of: the product polyunsaturated fatty acid produced according to the method described with respect to SEQ ID NO:2, the another polyunsaturated fatty acid produced according to the method described above with respect to SEQ ID NO:2, and the final polyunsaturated fatty acid produced according to the method described with respect to SEQ ID NO:2. The product polyunsaturated fatty acid may be, for example, DGLA, 20:4n-3 or ADA. The another polyunsaturated fatty acid may be, for example, AA, EPA or ω6-docosapentaenoic acid. The final polyunsaturated fatty acid may be, for example, DHA, adrenic acid, ω6-docosapentaenoic acid or ω3-docosapentaenoic acid.

The invention also includes a cosmetic comprising a polyunsaturated fatty acid selected from the group consisting of: the product polyunsaturated fatty acid produced according to the method described above with respect to SEQ ID NO:2, the another polyunsaturated fatty acid produced according to the method described above with respect to SEQ ID NO:2, and the final polyunsaturated fatty acid produced according to the method described above with respect to SEQ ID NO:2.

Additionally, the present invention includes a method of preventing or treating a condition caused by insufficient intake or production of polyunsaturated fatty acids comprising administering to the patient the nutritional composition described directly above in an amount sufficient to effect the prevention or treatment.

Furthermore, the present invention includes an isolated nucleotide sequence corresponding to or complementary to at least about 35% of the nucleotide sequence shown in SEQ ID NO:3 (FIG. 43). This sequence may be that represented by SEQ ID NO:3. This sequence encodes a functionally active elongase which utilizes a polyunsaturated fatty acid or a monounsaturated fatty acid as a substrate. The sequence is derived from a mammal such as, for example, a human.

The invention also includes a purified protein encoded by this nucleotide sequence. Also, the invention includes a purified polypeptide which elongates polyunsaturated fatty acids or monounsaturated fatty acids and has at least about 30% amino acid similarity to the amino acid sequence of this purified protein.

Additionally, the invention includes method of producing an elongase enzyme comprising the steps of: a) isolating the nucleotide sequence represented by SEQ ID NO:3 (FIG. 43); b) constructing a vector comprising: i) the isolated nucleotide sequence operably linked to ii) a promoter; and c) introducing said vector into a host cell under time and conditions sufficient for expression of the elongase enzyme. The host cell may be the same as that described above with respect to the corresponding methods utilizing SEQ ID NO:1 or 2.

The invention also includes a vector comprising: a) a nucleotide sequence as represented by SEQ ID NO:3 (FIG. 43) operably linked to b) a promoter, as well as a host cell comprising this vector. The host cell may be the same as that described above.

The invention also includes a plant cell, plant or plant tissue comprising the above-described vector comprising SEQ ID NO:3, wherein expression of the nucleotide sequence of the vector results in production of at least one fatty acid selected from the group consisting of a monounsaturated fatty acid and a polyunsaturated fatty acid by said plant cell, plant or plant tissue. The polyunsaturated fatty acid may be, for example, DGLA, 20:4n-3 or ADA. The invention also includes one or more plant oils or acids expressed by the plant cell, plant or plant tissue.

The invention also includes a transgenic plant comprising the vector comprising SEQ ID NO:3, wherein expression of the nucleotide sequence of the vector results in production of a polyunsaturated fatty acid in seeds of the transgenic plant.

Additionally, the present invention includes a transgenic, non-human mammal whose genome comprises a human DNA sequence encoding an elongase operably linked to a promoter. The DNA sequence is represented by SEQ ID NO:3 (FIG. 43). The invention also includes a fluid produced by said transgenic, non-human mammal wherein said fluid comprises a detectable level of at least one elongase or products thereof.

The invention also encompasses a method for producing a polyunsaturated fatty acid comprising the steps of: a) isolating the nucleotide sequence represented by SEQ ID NO:3 (FIG. 43); b) constructing a vector comprising said nucleotide sequence; c) introducing the vector into a host cell under time and conditions sufficient for expression of elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA or AA, and the product polyunsaturated fatty acid may be, for example, DGLA, 20:4n-3, or ADA, respectively. The method may further comprise the step of exposing the product polyunsaturated fatty acid to at least one desaturase in order to convert the product polyunsaturated fatty acid to another polyunsaturated fatty acid. The product polyunsaturated fatty acid may be, for example, DGLA, 20:4n-3 and ADA, the another polyunsaturated fatty acid may be, for example, AA, EPA, and ω6-docosapentaenoic acid, respectively, and the at least one desaturase is Δ5-desaturase with respect to production of AA or EPA and Δ4-desaturase with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, DHA, ADA, ω6-docosapentaenoic acid, and ω3-docosapentaenoic acid.

The nutritional composition comprising at least one polyunsaturated fatty acid which may be, for example, product polyunsaturated fatty acid produced according to the method recited above in connection with SEQ ID NO:3, another polyunsaturated fatty acid produced according to the method recited above in connection with SEQ ID NO:3, and the final polyunsaturated fatty acid produced according to the method recited above in connection with SEQ ID NO:3. The product polyunsaturated fatty acid may be, for example, DGLA, 20:4n-3, or ADA. The another polyunsaturated fatty acid may be selected from the group consisting of AA, EPA, or ω6-docosapentaenoic acid. The final polyunsaturated fatty acid may be, for example, DHA, ADA, ω6-docosapentaenoic acid, or ω3-docosapentaenoic acid.
The other properties or characteristic of the nutritional composition (e.g., administration, components, etc.) as the same as those recited above with respect to the other nutritional compositions.

Moreover, the present invention also includes a pharmaceutical composition comprising 1) at least one polyunsaturated fatty acid selected from the group consisting of: the product polyunsaturated fatty acid produced according to the method described above in connection with SEQ ID NO:3, the another polyunsaturated fatty acid produced according to the method described above in connection with SEQ ID NO:3, and the final polyunsaturated fatty acid produced according to the method described above in connection with SEQ ID NO:3 and 2) a pharmaceutically acceptable carrier. The other properties of the composition (e.g., administration, additional components, etc.) are the same as those recited above with respect to the other pharmaceutical compositions.

The present invention also includes an animal feed comprising at least one polyunsaturated fatty acid selected from the group consisting of: the product polyunsaturated fatty acid produced according to the method recited above with respect to SEQ ID NO:3, the another polyunsaturated fatty acid produced according to the method recited above with respect to SEQ ID NO:3, and the final polyunsaturated fatty acid produced according to the method recited above with respect to SEQ ID NO:3. The product polyunsaturated fatty acid may be, for example, DGLA, 20:4n-3, or ADA. The polyunsaturated fatty acid may be, for example, AA, EPA, or ω6-docosapentaenoic acid.
The final polyunsaturated fatty acid may be, for example, DHA, ADA, ω6-docosapentaenoic acid or ω3-docosapentaenoic acid.

Also, the present invention includes a cosmetic comprising a polyunsaturated fatty acid selected from the group consisting of: the product polyunsaturated fatty acid produced according to the method recited above with respect to SEQ ID NO:3, said another polyunsaturated fatty acid produced according to the method recited above in connection with SEQ ID NO:3, and the final polyunsaturated fatty acid produced according to the method recited above in connection with SEQ ID NO:3.

A method of preventing or treating a condition caused by insufficient intake of polyunsaturated fatty acids comprising administering to the patient the nutritional composition recited above in connection with SEQ ID NO:3 in an amount sufficient to effect the prevention or treatment.

Additionally, the present invention includes an isolated nucleotide sequence corresponding to or complementary to at least about 35% of the nucleotide sequence shown in SEQ ID NO:4 (FIG. 46). The sequence may be represented by SEQ ID NO:4.

It encodes a functionally active elongase which utilizes a polyunsaturated fatty acid as a substrate. The sequence may be derived or isolated from a nematode of the genus *Caenorhabditis* and, in particular, may be isolated from *C. elegans*.

The present invention includes a purified protein encoded by the nucleotide sequence above. The invention also includes a purified polypeptide which elongates polyunsaturated fatty acids and has at least about 30% amino acid similarity to the amino acid sequence of the purified protein.

Additionally, the present invention includes a method of producing an elongase enzyme comprising the steps of: a) isolating the nucleotide sequence represented by SEQ ID NO:4 (FIG. 46); b) constructing a vector comprising: i) the isolated nucleotide sequence operably linked to ii) a promoter; and c) introducing the vector into a host cell under time and conditions sufficient for expression of the elongase enzyme. The properties of the host cell are the same as those described above in connection with SEQ ID NO:1, SEQ ID NO:2 and SEQ ID NO:3.

The present include also encompasses a vector comprising: a) a nucleotide sequence as represented by SEQ ID NO:4 (FIG. 46) operably linked to b) a promoter, as well as a host cell comprising this vector. The host cell has the same properties as those recited above in connection with the host cell recited above for SEQ ID NO:1, SEQ ID NO:2, and SEQ ID NO:3.

Moreover, the present invention includes a plant cell, plant or plant tissue comprising the above vector comprising SEQ ID NO:4, wherein expression of said nucleotide sequence of the vector results in production of a polyunsaturated fatty acid by the plant cell, plant or plant tissue. The polyunsaturated fatty acid may be, for example, DGLA, 20:4n-3, or ADA. The invention also includes one or more plant oils or fatty acids expressed by this plant cell, plant or plant tissue.

The invention also includes transgenic plant comprising the above vector including the nucleotide sequence corresponding to SEQ ID NO:4, wherein expression of the nucleotide sequence of the vector results in production of a polyunsaturated fatty acid in seeds of the transgenic plant.

Additionally, the present invention includes a transgenic, non-human mammal whose genome comprises a *C. elegans* DNA sequence encoding an elongase operably linked to a promoter.
The DNA sequence may be represented by SEQ ID NO:4 (FIG. 46).
The invention also includes a fluid produced by the transgenic, non-human mammal of claim 187 wherein the fluid comprises a detectable level of at least one elongase or products thereof.

The invention also includes a method for producing a polyunsaturated fatty acid comprising the steps of: a) isolating the nucleotide sequence represented by SEQ ID NO:4 (FIG. 46); b) constructing a vector comprising the isolated nucleotide sequence; c) introducing the vector into a host cell under time and conditions sufficient for expression of an elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA, or AA, and the product polyunsaturated fatty acid may be, for example, DGLA, 20:4n-3, or ADA, respectively. The method may further comprise the step of exposing the expressed elongase enzyme to at least one desaturase in order to convert said product polyunsaturated fatty acid to another polyunsaturated fatty acid. The product polyunsaturated fatty acid may be, for example, DGLA, 20:4n-3 or ADA, the another polyunsaturated fatty acid may be, for example, AA, EPA or ω6-docosapentaenoic acid, respectively, and the at least one desaturase is Δ5-desaturase with respect to production of AA or EPA, and Δ4-desaturase with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, DHA, ADA, ω6-docosapentaenoic acid, or ω3-docosapentaenoic acid.

The invention also includes a nutritional composition comprising at least one polyunsaturated fatty acid selected from the group consisting of said the polyunsaturated fatty acid produced according to the method described above in connection with SEQ ID NO:4, the another polyunsaturated fatty acid produced according to the method described above in connection with SEQ ID NO:4, and the final polyunsaturated fatty acid produced according to the method recited above in connection with SEQ ID NO:4. The product polyunsaturated fatty acid may be, for example, DGLA, 20:4n-3, or ADA. The another polyunsaturated fatty acid may be, for example, AA, EPA, or ω6-docosapentaenoic acid. The final polyunsaturated fatty acid may be, for example, DHA, ADA, ω6-docosapentaenoic acid, or ω3-docosapentaenoic acid. The other characteristics of the composition are the same as those recited for the nutritional compositions present above.

Additionally, the present invention includes a pharmaceutical composition comprising 1) at least one polyunsaturated fatty acid selected from the group consisting of: the product polyunsaturated fatty acid produced according to the method recited above in connection with SEQ ID NO:4, the another polyunsaturated fatty acid produced according to the method recited above in connection with SEQ ID NO:4, and the final polyunsaturated fatty acid produced according to the method recited above in connection with SEQ ID NO:4 and 2) a pharmaceutically acceptable carrier. The composition has the same properties (e.g., administration, added elements, etc.) as those described above with respect to the other pharmaceutical compositions.

The present invention also includes an animal feed comprising at least one polyunsaturated fatty acid selected from the group consisting of the product polyunsaturated fatty acid produced according to the method described above in connection with SEQ ID NO:4, the another polyunsaturated fatty acid produced according to the method recited above in connection with SEQ ID NO:4, and the final polyunsaturated fatty acid produced according to the method described above in connection with SEQ ID NO:4. The product polyunsaturated fatty acid may be, for example, DGLA, 20:4n-3 or ADA. The another polyunsaturated fatty acid may be, for example, AA, EPA or ω6-docosapentaenoic acid. The polyunsaturated fatty acid may be, for example, DHA, ADA, ω6-docosapentaenoic acid or ω3-docosapentaenoic acid.

Additionally, the present invention includes a cosmetic comprising a polyunsaturated fatty acid selected from the group consisting of the product polyunsaturated fatty acid produced according to the method recited above in connection with SEQ ID NO:4, the another polyunsaturated fatty acid produced according to the method recited above in connection with SEQ ID NO:4 and the final polyunsaturated fatty acid produced according to the method described above in connection with SEQ ID NO:4.

Furthermore, the present invention encompasses a method of preventing or treating a condition caused by insufficient intake or production of polyunsaturated fatty acids comprising administering to the patient the nutritional composition recited with respect to SEQ ID NO:4 in an amount sufficient to effect the treatment or prevention.

All U.S. patents and publications referred to herein are hereby incorporated in their entirety by reference.

BRIEF DESCRIPTION OF THE DRAWINGS

FIG. 2 represents the percent similarity and percent identity between the amino acid sequences of jojoba KCS (SEQ ID NO:5) and ELO2 (SEQ ID NO:6).

FIG. 3 represents the *S. cerevisiae* ELO2 sequence (SEQ ID NO:7) homologous to the jojoba KCS sequence (primer sequence underlined) of FIG. 2.

FIG. 5 represents a comparison of the nucleotide sequences of clones pRAE-5 (SEQ ID NO:8) and pRAE-6 (SEQ ID NO:9).

FIG. 6 illustrates the complete nucleotide sequence of *Mortierella alpina* elongase (MAELO)(SEQ ID NO:1).

FIG. 7 represents the amino acid sequence of the *Mortierella alpina* elongase translated from MAELO (SEQ ID NO:10) (see FIG. 6).

FIG. 8 represents an amino acid sequence alignment among 3 elongases: *S. cerevisiae* ELO2 (GNS1)(SEQ ID NO:11), *S. cerevisiae* ELO3 (SUR4) and the translated MAELO sequence (SEQ ID NO:10) as shown in FIG. 7.

FIG. 9 represents a comparison between the nucleotide sequence MAELO (SEQ ID NO:13) and the nucleotide sequence of ELO2 from *S. cerevisiae* (SEQ ID NO:14).

FIGS. 10A and 10B represent the PUFA elongase activity of MAELO expressed in baker's yeast.

FIG. 11 illustrates the PUFA elongase activity of MAELO when co-expressed with the Δ5-desaturase cDNA from *M. alpina* to produce AA.

FIG. 12 compares the PUFA elongase activity of MAELO to the overexpression of ELO2 from *S. cerevisiae* in baker's yeast.

FIGS. 13, 14 and 15 represent three separate comparisons of amino acid sequences derived from *C. elegans* nucleotide sequences in the GenEMBL database with the translated MAELO (FIG. 13: SEQ ID NO:15 and SEQ ID NO:16, respectively; FIG. 14: SEQ ID NO:17 and SEQ ID NO:18, respectively; FIG. 15: SEQ ID NO:19 and SEQ ID NO:20, respectively).

FIG. 16 shows the comparison between amino acid translations of two different mammalian sequences in the GenEMBL database and the translated MAELO (U97107: SEQ ID NO:21; MAELO: SEQ ID NO:22; MAELO: SEQ ID NO:23; AC004050: SEQ ID NO:24).

FIG. 17 shows the comparison of a translated DNA sequence (SEQ ID NO:25) (see published PCT application WO 88/07577) with the amino acid sequence derived from MAELO (SEQ ID NO:26), which was detected during a database search.

FIG. 18 shows the complete nucleotide sequence of the Δ5-desaturase from *M. alpina* (SEQ ID NO:27).

FIG. 20 represents the PUFA elongase activity of the five MAD708 clones in yeast with GLA as substrate. All clones have apparent elongase activity.

FIG. 22 shows the complete nucleotide sequence of the *M. alpina* cDNA(SEQ ID NO:2), contained in the plasmid pRPB2, which is designated GLELO for its GLA elongase activity.

FIG. 23 represents the amino acid sequence of the *M. alpina* elongase (SEQ ID NO:28)translated from GLELO (see FIG. 22).

FIG. 24 illustrates the n-6 PUFA elongase activity in an induced culture of 334 (pRPB2) when supplemented with GLA.

FIG. 25 represents the n-3 and n-6 PUFA elongase activity in an induced culture of 334(pRPB2) when supplemented with 25 ③m of other fatty acid substrates.

FIG. 26A illustrates the elongase activity of GLELO with GLA as a substrate when co-expressed with the *M. alpina* Δ5-desaturase cDNA to produce AA. FIG. 26B illustrates the elongase activity of GLELO with STA as a substrate when co-expressed with the *M. alpina* Δ5-desaturase cDNA to produce EPA.

FIG. 27 illustrates the comparison between the translated GLELO sequence (SEQ ID NO:29)(see FIG. 23) and the translated MAELO sequence (SEQ ID NO:30)(see FIG. 7).

FIG. 28 represents a comparison of the amino acid sequence of 4 elongases: the translated amino acid sequence of GLELO (see FIG. 23), MAELO (see FIG. 7), *S. cerevisiae* ELO2 (GNS1), and *S. cerevisiae* ELO3 (SUR4). The histidine box is underlined.

FIG. 29 represents an alignment between translated MAELO sequence (SEQ ID NO:31) and translated putative human homologue HS1 sequence (SEQ ID NO:32).

FIG. 30 represents an alignment between the translated MAELO sequence (SEQ ID NO:33) and the translated putative human homologue HS2 sequence (SEQ ID NO:34).

FIG. 31 shows an alignment between the translated MAELO sequence (SEQ ID NO:35) and the translated putative mouse homologue MM2 sequence (SEQ ID NO:36).

FIG. 32 represents an alignment between the translated MAELO (SEQ ID NO:37)and the translated putative mouse homologue AI225632 sequence (SEQ ID NO:38).

FIG. 33 illustrates an alignment between the translated GLELO sequence (SEQ ID NO:39) and the translated human homologue AI815960 sequence (SEQ ID NO:40)

FIG. 34 shows an alignment between the translated GLELO sequence (SEQ ID NO:41) and the translated putative human homologue HS1 sequence (SEQ ID NO:42).

FIG. 35 represents an alignment between the translated GLELO sequence (SEQ ID NO:43) and the translated putative human homologue sequence from AC004050 (SEQ ID NO:44).

FIG. 36 illustrates an alignment between the translated GLELO sequence (SEQ ID NO:45) and the translated putative mouse homologue MM2 sequence (SEQ ID NO:46).

FIG. 37 represents an alignment of the translated GLELO sequence (SEQ ID NO:47) and a translated putative mouse homologue AI225632 sequence (SEQ ID NO:48).

FIG. 38 illustrates an alignment of the translated GLELO sequence (SEQ ID NO:49) and a translated putative mouse homologue U97107 (SEQ ID NO:50).

FIG. 39 represents an alignment of the translated GLELO sequence (SEQ ID NO:51) and a translated putative *C. elegans* U68749 (F56H11.4) homologue sequence (SEQ ID NO:52).

FIG. 40 shows an alignment between the translated MAELO sequence (SEQ ID NO:53) and a translated putative *C. elegans* U68749 (F56H11.4) homologue sequence (SEQ ID NO:54).

FIG. 41 represents an alignment between the translated GLELO sequence (SEQ ID NO:55) and a translated putative *Drosophila melanogaster* homologue sequence, DM1 (SEQ ID NO:56).

FIG. 42 illustrates an alignment between the translated MAELO sequence (SEQ ID NO:57) and a translated putative *Drosophila melanogaster* homologue sequence (SEQ ID NO:58), DM1.

FIG. 43 illustrates the complete nucleotide sequence of a human elongase HSELO1 (SEQ ID NO:59).

FIG. 44 represents the deduced amino acid sequence of the human elongase HSELO1.

FIG. 45 illustrates the elongase activity (PUFA and others) of an induced culture of 334 (pRAE-58-A1) when supplemented with GLA or AA.

FIG. 46 shows the complete nucleotide sequence of the *C. elegans* elongase CEELO (SEQ ID NO:4).

FIG. 47 represents the deduced amino acid of *C. elegans* elongase CEELO (SEQ ID NO:60).

FIG. 48 illustrates the PUFA elongase activity of an induced culture of 334 (pRET-21) and 334 (pRET-22) when supplemented with GLA and AA.

FIG. 49 represents the complete nucleotide sequence of the putative human elongase gene HS3 (SEQ ID NO:61).

FIG. 50 illustrates the deduced amino acid sequence of the putative human elongase enzyme HS3 (SEQ ID NO:62).

DETAILED DESCRIPTION OF THE INVENTION

Figure 1:
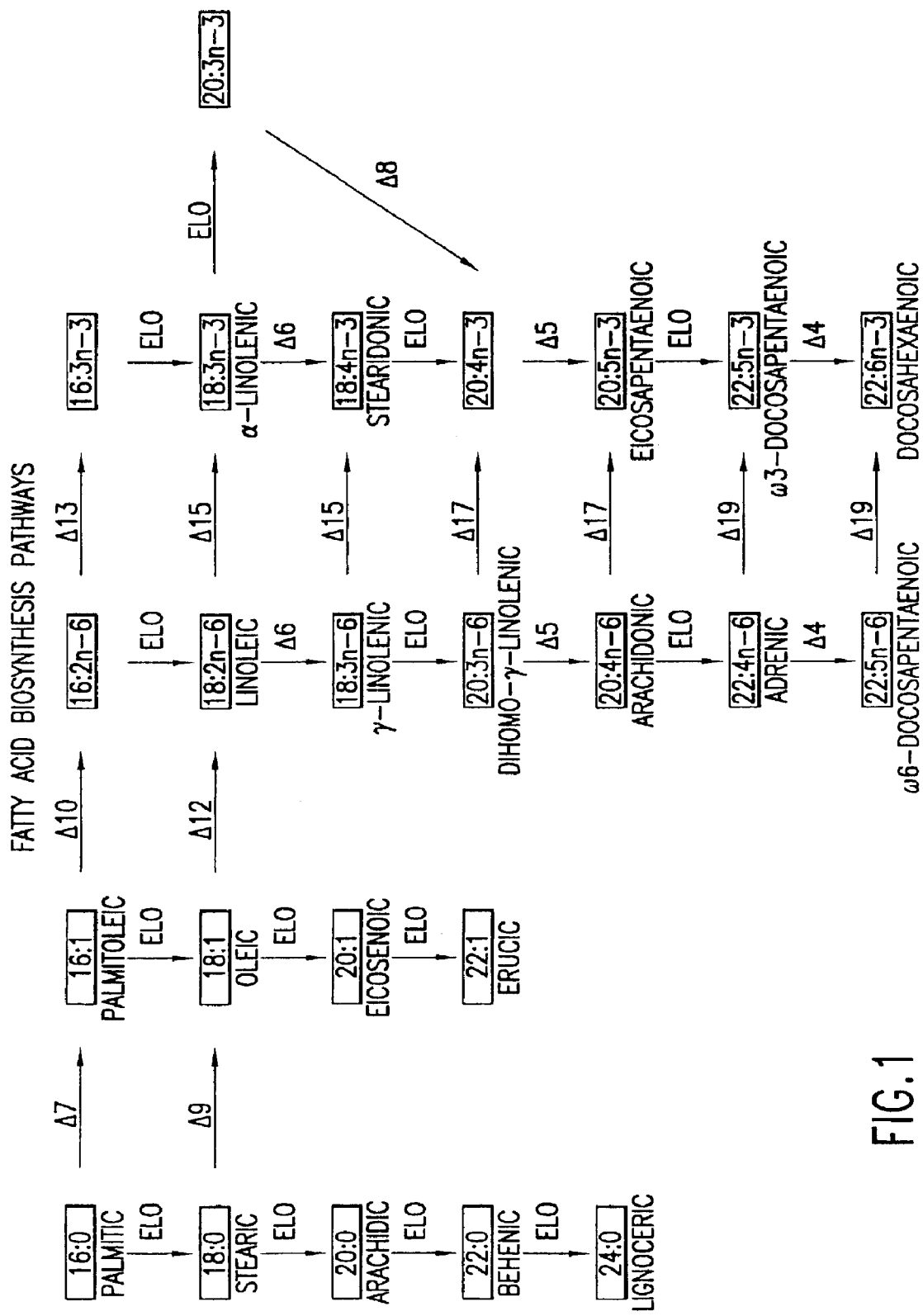
FIG. 1 represents various fatty acid biosynthesis pathways. The role of the elongase enzyme (elo) should be noted.

The subject invention relates to nucleotide and corresponding amino acid sequences of two elongase cDNAs derived from *Mortierella alpina*, as well as to nucleotide and corresponding amino acid sequences of an elongase cDNA derived from a human and one derived from *C. elegans*. Furthermore, the subject invention also includes uses of the cDNAs and of the proteins encoded by the genes. For example, the genes and corresponding enzymes may be used in the production of polyunsaturated fatty acids and/or monounsaturated fatty acids such as DGLA, AA, ADA, EPA and/or DHA which may be added to pharmaceutical compositions, nutritional compositions and to other valuable products.

The Elongase Genes and Enzymes Encoded Thereby

As noted above, an elongase enzyme encoded by an elongase cDNA is essential in the production of various polyunsaturated fatty acids, in particular, 20–24 carbon PUFAs. With respect to the present invention, the nucleotide sequence of the isolated *M. alpina* elongase cDNA (MAELO) is shown in FIG. 6, and the amino acid sequence of the corresponding purified protein or enzyme encoded by this nucleotide sequence is shown in FIG. 7. Additionally, the nucleotide sequence of the isolated GLA elongase cDNA (GLELO) is shown in FIG. 22, and the amino acid sequence of the corresponding purified protein or enzyme encoded by this nucleotide sequence is shown in FIG. 23. The nucleotide sequence of the isolated human sequence 1 (HSELO1) elongase is shown in FIG. 43, and the amino acid sequence of the corresponding purified protein or enzyme encoded by this sequence is shown in FIG. 44. Furthermore, the nucleotide sequence of the isolated *C. elegans* elongase cDNA (CEELO1) is shown in FIG. 46, and the amino acid sequence of the corresponding purified protein or enzyme encoded thereby is shown in FIG. 47.

As an example, the isolated elongases encoded by the cDNAs of the present invention elongate GLA to DGLA or elongate STA to 20:4n-3 or elongate AA to ADA. The production of arachidonic acid from DGLA, or EPA from 20:4n-3, is then catalyzed by a Δ5-desaturase. Thus, neither AA (or EPA), nor DGLA (or 20:4n-3) nor ADA (or ω3-docosapentaenoic acid), can be synthesized without at least one elongase cDNA and enzyme encoded thereby.

It should be noted that the present invention also encompasses nucleotide sequences (and the corresponding encoded proteins) having sequences corresponding to (i.e., having identity to) or complementary to at least about 50%, preferably at least about 60%, and more preferably at least about 70% of the nucleotides in SEQ ID NO:1 (i.e., the nucleotide sequence of the MAELO cDNA described herein (see FIG. 6)). Furthermore, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:2 (i.e., the nucleotide sequence of the GLELO cDNA described herein (see FIG. 22). Additionally, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:3 (i.e., the nucleotide sequence of the human sequence 1 (HSELO1) cDNA described herein (see FIG. 43). In addition, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:4 (i.e., the nucleotide sequence of the *C. elegans* cDNA, CEELO1, described herein (see FIG. 46). Such sequences may be derived from non-*Mortierella* sources (e.g., a eukaryote (e.g., *Thraustochytrium* spp. (e.g., *Thraustochytrium aureum* and *Thraustochytrium roseum*), *Schizochytrium* spp. (e.g., *Schizochytrium aggregatum*), *Conidiobolus* spp. (e.g., *Conidiobolus nanodes*), *Entomorphthora* spp. (e.g., *Entomorphthora exitalis*), *Saprolegnia* spp. (e.g., *Saprolegnia parasitica* and *Saprolegnia diclina*), *Leptomitus* spp. (e.g., *Leptomitus lacteus*), *Entomophthora* spp., *Pythium* spp., *Porphyridium* spp. (e.g., *Porphyridium cruentum*), *Conidiobolus* spp., *Phytophathora* spp., *Penicillium* spp., *Coidosporium* spp., *Mucor* spp. (e.g., *Mucor circinelloides* and *Mucor javanicus*), *Fusarium* spp., *Aspergillus* spp. and *Rhodotorula* spp.), a yeast (e.g., *Dipodascopsis uninucleata*), a non-mammalian organism such as a fly (e.g., *Drosophila melanogaster*) or *Caenorhabditis* spp. (e.g., *Caenorhabditis elegans*), or a mammal (e.g., a human or a mouse). Such sequences may be derived from species within the genus *Mortierella*, other than the species *alpina*, for example, *Mortierella elongata*, *Mortierella exigua*, *Mortierella isabellina*, *Mortierella hygrophila*, and *Mortierella ramanniana*, va. *angulispora*. Furthermore, the present invention also encompasses fragments and derivatives of the nucleotide sequences of the present invention (i.e., SEQ ID NO:1 (MAELO), SEQ ID NO:2 (GLELO), SEQ ID NO:3 (HSELO1) and SEQ ID NO:4 (CEELO1)), as well as of the sequences derived from non-*Mortierella* sources and having the above-described complementarity or correspondence/identity. Functional equivalents of the above-sequences (i.e., sequences having elongase activity) are also encompassed by the present invention.

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

"Identity" between two nucleotide sequences is defined as the degree of sameness, correspondence or equivalence between the same strands (either sense or antisense) of two DNA segments. The greater the percent identity, the higher the correspondence, sameness or equivalence between the strands.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino acid sequences is defined as the presence of a series of exactly alike or invariant amino acid residues in both sequences.)

The definitions of "complementarity", "identity", and "similarity" are well known to those of ordinary skill in the art.

The invention also includes a purified polypeptide which elongates polyunsaturated and monounsaturated fatty acids and has at least about 50% amino acid similarity to the amino acid sequences of the above-noted proteins (see, e.g., FIG. 7 (MAELO)) and which are, in turn, encoded by the above-described nucleotide sequences. Additionally, the present invention includes a purified polypeptide which elongates polyunsaturated fatty acids and has at least about 30% amino acid similarity to the amino acid sequences of the above-noted proteins (see, e.g., FIG. 23 (GLELO)) and which are, in turn, encoded by the above-described nucleotide sequences. Furthermore, the invention also includes a purified polypeptide which elongates polyunsaturated and monounsaturated fatty acids and has at least about 30% amino acid similarity to the amino acid sequences of the above-noted proteins (see, e.g., FIG. 44 (HSELO1)) and which are, in turn, encoded by the above-described nucleotide sequences. Also, the present invention includes a purified polypeptide which elongates polyunsaturated fatty acids and has at least about 30% amino acid similarity to the amino acid sequences of the above-noted proteins (see, e.g., FIG. 47 (CEELO1)) and which are, in turn, encoded by the above-described nucleotide sequences.

The present invention also encompasses an isolated nucleotide sequence which encodes PUFA elongase activity and that is hybridizable, under moderately stringent conditions, to a nucleic acid having a nucleotide sequence corresponding or complementary to the nucleotide sequence represented by SEQ ID NO:1 shown in FIG. 6 (MAELO) and/or SEQ ID NO:2 shown in FIG. 22 (GLELO) and/or SEQ ID NO:3 (HSELO1) shown in FIG. 43 and/or SEQ ID NO:4 (CEELO1) shown in FIG. 46. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementarity. Such variables are well known in the art. More specifically, the greater the degree of similarity or homology between two nucleotide sequences, the greater the value of Tm, melting temperature, for hybrids of nucleic acids having those sequences. For, hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Production of the Elongase Enzyme

Once the gene encoding the elongase has been isolated, it may then be introduced into either a prokaryotic or eukaryotic host cell through the use of a vector, plasmid or construct.

The vector, for example, a bacteriophage, cosmid or plasmid, may comprise the nucleotide sequence encoding the elongase as well as any promoter which is functional in the host cell and is able to elicit expression of the elongase encoded by the nucleotide sequence. The promoter is in operable association with or operably linked to the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TP1, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, 2$^{nd}$ ed., Vol. 1–3, ed. Sambrook et al., Cold Spring Harbor Laboratory Press (1989)). The host cell is then cultured under suitable conditions permitting expression of the PUFA which is then recovered and purified.

It should also be noted that one may design a unique triglyceride or oil if one utilizes one construct or vector comprising the nucleotide sequences of two or more cDNAs (e.g., MAELO, GLELO, HSELO1 and/or CEELO1). This vector may then be introduced into one host cell. Alternatively, each of the sequences may be introduced into a separate vector. These vectors may then be introduced into two host cells, respectively, or into one host cell.

Examples of suitable prokaryotic host cells include, for example, bacteria such as *Escherichia coli, Bacillus subtilis* as well as cyanobacteria such as *Spirulina* spp. (i.e., blue-green algae). Examples of suitable eukaryotic host cells include, for example, mammalian cells, plant cells, yeast cells such as *Saccharomyces* spp., *Lipomyces* spp., *Candida* spp. such as *Yarrowia* (*Candida*) spp., *Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., the elongase) encoded by one or both of the above-described nucleotide sequences. More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130–2133 (1997)). Gestation and birth are then permitted to occur (see, e.g., U.S. Pat. No. 5,750,176 and U.S. Pat. No. 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene or genes encoding the elongase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of an elongase polypeptide, functional transcriptional and translational initiation and termination regions are operably linked to the DNA encoding the elongase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379. Alternatively, the expressed protein can be an enzyme which produces a product which may be incorporated, either directly or upon further modifications, into a fluid fraction from the host plant. Expression of an elongase gene or genes, or antisense elongase transcripts, can alter the levels of specific PUFAs, or derivatives thereof, found in plant parts and/or plant tissues. The elongase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)), plant tissue, corn, potatoe, sunflower, safflower or flax may also be utilized as a host or host cell, respectively, for expression of the elongase enzyme(s) which may, in turn, be utilized in the production of polyunsaturated fatty acids. More specifically, desired PUFAs can be expressed in seed. Methods of isolating seed oils are known in the art. Thus, in addition to providing a source for PUFAs, seed oil components may be manipulated through the expression of the elongase genes, as well as perhaps desaturase genes, in order to provide seed oils that can be added to nutritional compositions, pharmaceutical compositions, animal feeds and cosmetics. Once again, a vector which comprises a DNA sequence encoding the elongase operably linked to a promoter, will be introduced into the plant tissue or plant for a time and under conditions sufficient for expression of the elongase gene. The vector may also comprise one or more genes which encode other enzymes, for example, Δ4-desaturase, Δ5-desaturase, Δ6-desaturase, Δ8-desaturase, Δ9-desaturase, Δ10-desaturase, Δ12-desaturase, Δ13-desaturase, Δ15-desaturase, Δ17-desaturase and/or Δ19-desaturase. The plant tissue or plant may produce the relevant substrate (e.g., DGLA, GLA, STA, AA, ADA, EPA, 20:4n-3, etc.) upon which the enzymes act or a vector encoding enzymes which produce such substrates may be introduced into the plant tissue, plant cell, plant, or host cell of interest. In addition, substrate may be sprayed on plant tissues expressing the appropriate enzymes. Using these various techniques, one may produce PUFAs (e.g., n-6 unsaturated fatty acids such as DGLA, AA or ADA, or n-3 fatty acids such as EPA or DHA) by use of a plant cell, plant tissue, plant, or host cell of interest. It should also be noted that the invention also encompasses a transgenic plant comprising the above-described vector, wherein expression of the nucleotide sequence of the vector results in production of a polyunsaturated fatty acid in, for example, the seeds of the transgenic plant.

The substrates which may be produced by the host cell either naturally or transgenically, as well as the enzymes which may be encoded by DNA sequences present in the vector, which is subsequently introduced into the host cell, are shown in FIG. 1.

In view of the above, the present invention also encompasses a method of producing one of the elongase enzymes described above comprising the steps of: 1) isolating the desired nucleotide sequence of the elongase cDNA; 2) constructing a vector comprising said nucleotide sequence; and 3) introducing said vector into a host cell under time and conditions sufficient for the production of the elongase enzyme.

The present invention also encompasses a method of producing polyunsaturated fatty acids comprising exposing an acid to the elongase(s) produced as above such that the elongase converts the acid to a polyunsaturated fatty acid. For example, when GLA is exposed to elongase, it is converted to DGLA. DGLA may then be exposed to Δ5-desaturase which converts the DGLA to AA. The AA may then be converted to EPA by use of Δ17-desaturase which may be, in turn, converted to DHA by use of elongase and a Δ4-desaturase. Alternatively, elongase may be utilized to convert 18:4n-3 to 20:4n-3 which may be exposed to Δ5-desaturase and converted to EPA. Elongase may also be used to convert 18:3n-3 to 20:3n-3, which may be, in turn, converted to 20:4n-3 by a Δ8-desaturase. Thus, elongase may be used in the production of polyunsaturated fatty acids which may be used, in turn, for particular beneficial purposes. (See FIG. 1 for an illustration of the many critical roles elongase plays in several biosynthetic pathways.)

Uses of the Elongase Gene and Enzyme Encoded Thereby

As noted above, the isolated elongase cDNAs and the corresponding elongase enzymes (or purified polypeptides) encoded thereby have many uses. For example, each cDNA and corresponding enzyme may be used indirectly or directly in the production of polyunsaturated fatty acids, for example, DGLA, AA, ADA, 20:4n-3 or EPA. ("Directly" is meant to encompass the situation where the enzyme directly converts the acid to another acid, the latter of which is utilized in a composition (e.g., the conversion of GLA to DGLA)). "Indirectly" is meant to encompass the situation where a fatty acid is converted to another fatty acid (i.e., a pathway intermediate) by elongase (e.g., GLA to DGLA) and then the latter fatty acid is converted to another fatty acid by use of a non-elongase enzyme (e.g., DGLA to AA by Δ5-desaturase)). These polyunsaturated fatty acids (i.e., those produced either directly or indirectly by activity of the elongase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil or acid produced by use of at least one elongase enzyme, produced using the respective elongase gene, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed starch. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutrional formulas are well known in the art and are commercially available (e.g., Similac®, Ensure®, Jevity® and Alimentum® from Ross Products Division, Abbott Laboratories, Columbus, Ohio). An oil or fatty acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight % of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as AA, from about 0.22% to about 0.67% as DGLA, and from about 0.27% to about 1.04% as GLA. Thus, fatty acids such as DGLA, AA, EPA and/or docosahexaenoic acid (DHA), produced in accordance with the present invention, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil blend will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PUFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversion rate of DGLA to AA can be used to produce an AA to DGLA ratio of about 1:19, whereas a conversion rate of about 75% to 80% can be used to produce an AA to DGLA ratio of about 6:1. Therefore, whether in a cell culture system or in a host animal, regulating the timing, extent and specificity of elongase expression, as well as the expression of other desaturases, can be used to modulate PUFA levels and ratios. The PUFAs/acids produced in accordance with the present invention (e.g., AA and DGLA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the fatty acids and/or resulting oils produced using at least one of the elongase cDNAs (i.e., MAELO, GLELO, HSELO1, or CEELO), in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.) 732S-737S). Altered fatty acid metabolism and composition have been demonstrated in diabetic animals.

Furthermore, the compositions of the present invention, comprising PUFAs produced either directly or indirectly through the use of the elongase enzyme(s), may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p. 85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

The present invention may be illustrated by the use of the following non-limiting examples:

EXAMPLE I

Determination of Codon Usage in *Mortierella alpina*

The 5' end of 1000 random cDNA clones were sequenced from *Mortierella alpina* cDNA library. The sequences were translated in six reading frames using GCG (Genetics Computer Group (Madison, Wis.)) with the FastA algorithm (Pearson and Lipman, *Proc. Natl. Acad. Sci. USA* 85:2444–2448 (1988)) to search for similarity between a query sequence and a group of sequences of the same type (nucleic acid or protein), specifically with the Swissprot database (GeneBio, Geneva, Switzerland). Many of the clones were identified as a putative housekeeping gene based on protein sequence homology to known genes. Twenty-one *M. alpina* cDNA sequences which matched with known, housekeeping genes in the database were selected (see Table 1 below). *M. alpina* codon bias table (see Table 2) was generated based on these 21 sequences as well as the full length *M. alpina* Δ5- (see FIG. 18), Δ6-, and Δ12-desaturase sequences. Since the FastA alignment between the putative protein coded by the *M. alpina* cDNA sequence and the known protein sequence was weak in some areas, only the codons from areas of strong homology were used.

TABLE 1

| Clone # | Match | # of bp | # o |
|---|---|---|---|
| 193 | Elongation factor 1-alpha | 426 | 1 |
| 143 | 60S ribosomal protein L17 | 417 | 1 |
| 235 | Actin I | 360 | 1 |
| 299 | 40S ribosomal protein YS11 | 387 | 1 |
| 390 | Ras-related protein rab-1a | 342 | 1 |

TABLE 1-continued

| Clone # | Match | # of bp | # o |
|---|---|---|---|
| 65 | 40S ribosomal protein RP10 | 366 | 1 |
| 289 | Ubiquitin-conjugating enzyme E2-16 KD | 294 | 9 |
| 151 | Ubiquinol-cytochrome C reductase | 375 | 1 |
| 80 | Initiation factor 5A-2 | 183 | 6 |
| 33 | 60S ribosomal protein L15 | 252 | 8 |
| 132 | 60S ribosomal protein L3-2 | 300 | 1 |
| 198 | Histone H3 | 285 | 9 |
| 286 | 6-phosphogluconate dehydrogenase, decarboxylating | 363 | 1 |
| 283 | 40S ribosomal protein S22 | 261 | 8 |
| 127 | Elongation factor 2 | 231 | 7 |
| 197 | Actin, gamma | 252 | 8 |
| 496 | 40S ribosomal protein S16 | 270 | 9 |
| 336 | Histone H4 | 219 | 7 |
| 262 | Ubiquitin | 228 | 7 |
| 188 | Guanine nucleotide-binding protein beta subunit-like protein | 213 | 7 |
| 81 | Ubiquitin | 228 | 7 |
| 21 | TOTAL | 6252 | 20 |

TABLE 2

| Amino acid | Codon Bias | % used |
|---|---|---|
| Ala | GCC | 63% |
| Arg | CGC | 50% |
| Asn | AAC | 97% |
| Asp | GAC | 65% |
| Cys | TGC | 87% |
| Gln | CAG | 78% |
| Glu | GAG | 85% |
| Gly | GGT | 47% |
| His | CAC | 91% |
| Ile | ATC | 72% |
| Leu | CTC | 49% |
| Lys | AAG | 96% |
| Met | ATG | 100% |
| Phe | TTC | 78% |
| Pro | CCC | 68% |
| Ser | TCC | 46% |
| Thr | ACC | 78% |
| Trp | TGG | 100% |
| Tyr | TAC | 95% |
| Val | GTC | 72% |
| Stop | TAA | 50% |

EXAMPLE II

Cloning of a Full-length Elongase-like cDNA from *M. alpina*

The β-ketoacyl-coenzyme A synthase (KCS) from jojoba and the *Saccharomyces cerevisiae* elongase (ELO2) were aligned to determine an area of amino acid homology (see FIG. 2). The codon bias was applied to the area of sequence corresponding to the homologous amino acids between the two elongases, and primers were designed based on this biased sequence (see FIG. 3). The cDNA was excised from the M11 *M. alpina* cDNA library (Knutzon et al., *J. Biol. Chem.* 273:29360–29366 (1998)), which contains approximately 6×10⁵ clones with an average insert size of 1.1 Kb. The excised cDNA was amplified with internal primer RO339 (5'-TTG GAG AGG AGG AAG CGA CCA CCG AAG ATG ATG-3')(SEQ ID NO:63) and a vector forward primer RO317 (5'-CAC ACA GGA AAC AGC TAT GAC CAT GAT TAC G-3')(SEQ ID NO:64). Polymerase Chain Reaction (PCR) was carried out in a 100 µl volume containing: 300 ng of excised *M. alpina* cDNA library, 50 pmole each primer, 10 µl of 10× buffer, 1 µl 10 mM PCR Nucleotide Mix (Boehringer Mannheim Corp., Indianapolis, Ind.) and 1.0 U of Taq Polymerase. Thermocycler conditions in Perkin Elmer 9600 (Norwalk, Conn.) were as follows: 94° C. for 2 mins., then 30 cycles of 94° C. for 1 min., 58° C. for 2 mins., and 72° C. for 3 mins. PCR was followed by an additional extension at 72° C. for 7 minutes.

The PCR amplified product was run on a gel, an amplified fragment of approximately 360 bp was gel purified, and the isolated fragment was directly sequenced using ABI 373A DNA Sequencer (Perkin Elmer, Foster City, Calif.). The sequence analysis package of GCG was used to compare the obtained sequence with known sequences. The sequence was translated in all six reading frames in the GCG Analysis Program using the FastA algorithm (Pearson and Lipman, supra). The Swissprot database (GeneBio, Geneva, Switzerland) of proteins was searched. This translated cDNA fragment was identified as a part of a putative elongase based on the homology of the putative protein sequence to the *S. cerevisiae* ELO2 (GNS1), having 41.3% identity in 63 amino acids.

Figure 4A:
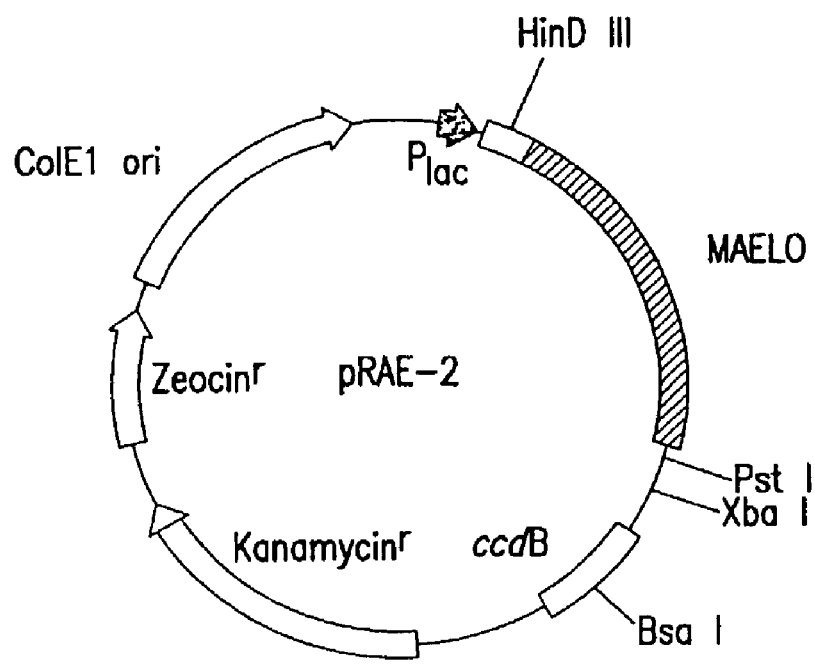
FIG. 4A shows the physical map of pRAE-2 containing the MAELO cDNA.
Figure 4B:
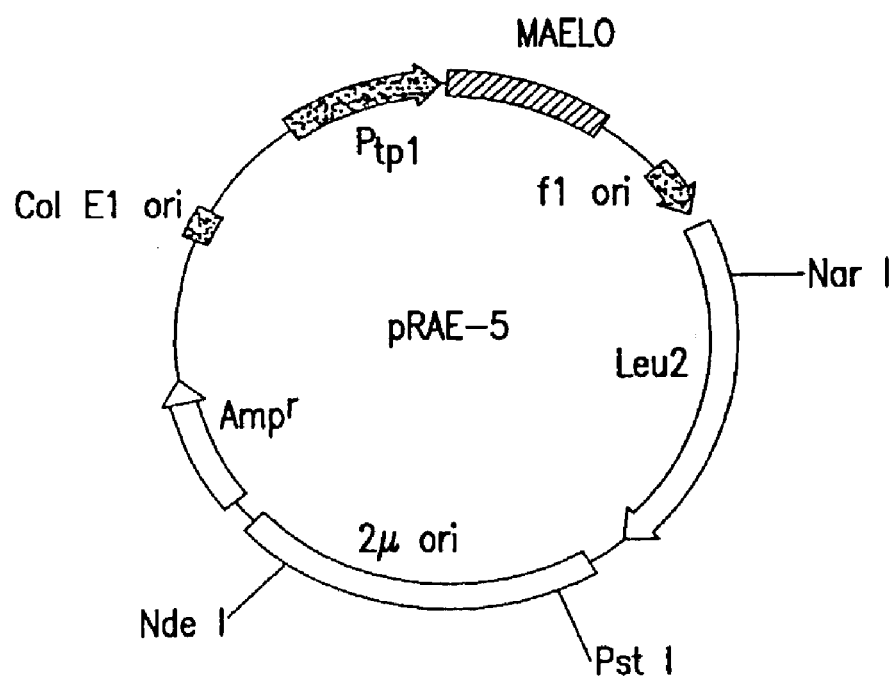
FIG. 4B represents the physical map of the constitutive expression vector, pRAE-5, used for elongase enzyme production in yeast.

New primers were designed based on the putative elongase sequence and the vector, pZL1 (Life Technologies, Inc., Gaithersburg, Md.) sequence used to construct, *M. alpina* cDNA library. The *M. alpina* excised cDNA library was PCR amplified again using primers RO350 (5'-CAT CTC AT G GAT CCG CCA TGG CCG CCG CAA TCT TG-3')(SEQ ID NO:65), which has an added BamHI restriction site (underlined), and the vector reverse primer RO352 (5'-ACG CGT ACG TAA AGC TTG-3')(SEQ ID NO:66) to isolate the full length *M. alpina* elongase cDNA, using previously described conditions. The termini of the approximately 1.5 Kb PCR amplified fragment was filled-in with T4 DNA polymerase (Boehringer Mannheim Corp., Indianapolis, Ind.) to create blunt ends and cloned into the pCR-blunt vector (Invitrogen Corp., Carlsbad, Calif.). This resulted in two clones, pRAE-1 and pRAE-2 (see FIG. 4A). (Plasmid DNA pRAE-2 was deposited with the American Type Culture Collection, 10801 University Boulevard, Manassas, Va. 20110–2209, on Aug. 28, 1998, under the terms of the Budapest Treaty, and was accorded deposit number ATCC 203166.) The elongase cDNAs from these vectors were cut out as an EcoRI fragment and cloned into the EcoRI digested pYX242 (Novagen, Madison, Wis.) vector. The clones pRAE-5 and pRAE-6 (see FIG. 4B) have the elongase cDNAs from pRAE-1 and pRAE-2, respectively. (Plasmid DNA pRAE-5 was deposited with the American Type Culture Collection, 10801 University Boulevard, Manassas, Va. 20110–2209, on Aug. 28, 1998, under the terms of the Budapest Treaty, and was accorded deposit number ATCC 203167.) The sequencing of pRAE-5 and pRAE-6 revealed that 5' untranslated region of the elongase gene in pRAE-5 is 16 bp shorter than that in pRAE-6 (see FIG. 5). The complete *M. alpina* elongase cDNA sequence, designated MAELO was obtained from pRAE-2 (see FIG. 6). FIG. 7 is the amino acid sequence obtained from the translation of MAELO. The Swissprot database (GeneBio, Geneva, Switzerland) was searched again, as previously described, with the translated MAELO: MAELO has 44.3% identity in 317 amino acids with *S. cerevisiae* GNS1(ELO2) and 44.7% identity in 318 amino acids with *S. cerevisiae* SUR4(ELO3). The FastA alignment among the three elongases is shown in FIG. 8. At the nucleotide level (see FIG. 9), MAELO has 57.4% identity in 549 bp overlap with *S. cerevisiae* GNS1 (ELO2) (GenBank Accession #S78624). However, the identity between the complete MAELO gene of 954 bp and *S. cerevisiae* GNS1(ELO2) is 33.0%.

EXAMPLE III

Expression of *M. alpina* Elongase cDNA in Baker's Yeast

The constructs pRAE-5, and pRAE-6 were transformed into *S. cerevisiae* 334 (Hoveland et al., *Gene* 83:57–64 (1989)) and screened for elongase activity. The plasmid pCGN7875 (Calgene LLC, Davis, Calif.) containing jojoba KCS gene in pYES2 vector (Invitrogen Corp., Carlsbad, Calif.) was used as a positive control. The substrate used to detect elongase activity in *M. alpina* elongase (MAELO) was GLA and that in jojoba KCS was oleic acid (OA). The negative control strain was *S. cerevisiae* 334 containing pYX242 vector. The cultures were grown for 40–48 hours at 25° C., in selective media (Ausubel et al., *Short Protocols in Molecular Biology*, Ch. 13, p. 3–5 (1992)), in the presence of a particular substrate. The expression of the jojoba KCS gene cloned in pYES2 was under the control of GAL1 promoter, while the promoter in pYX242 is TP1, which is constitutive. Hence, the 334 (pCGN7875) and 334 (pYES2) cultures were induced with galactose. The GC-FAME analysis of the lipid fraction of each cell pellet was performed as previously described (Knutzon et al., supra).

The elongase activity results from different experiments are provided in FIGS. 10A and 10B. The jojoba KCS elongates long chain monounsaturated fatty acids 18:1n-9 to 20:1n-9. The amino acid homology between the *M. alpina* elongase (MAELO) and the *S. cerevisiae* ELO2 and ELO3 suggested that the proteins encoded by these genes may have similar substrate specificity. The activity of the *M. alpina* elongase, elongation (MAELO) of long chain monounsaturated and saturated fatty acids, is seen in the conversion of 18:1n-9 to 20:1n-9 and also in the synthesis of 24:0. The control strain, 334 (pYX242) has very little or no detectable amount of 20:1 and 24:0 (see FIG. 10A). *M. alpina* elongase (MAELO) also acts on at least one PUFA, converting 18:3n-6(GLA) to 20:3n-6(DGLA). The percentage of the 20:3n-6 in total lipid is higher in the strain 334 (pRAE-5) and 334 (pRAE-6) with the *M. alpina* elongase (MAELO) cDNA when compared to that in the control 334 (pYX242). The percentages of 20:3n-6 produced were 0.092% for 334 (pYX242) vs. 0.324% for 334 (pRAE-5) and 0.269% for 334 (pRAE-6) (shown in parenthesis in FIGS. 10A and 10B). This difference in the fatty acid profile is also seen in the total amount of 20:3n-6 produced. Only 0.226 μg of 20:3n-6 was produced by 334 (pYX242) while 334 (pRAE-5) and 334 (pRAE-6) produced 2.504 μg of 20:3n-6 and 1.006 μg of 20:3n-6, respectively. Also, when no substrate is added, the level of 20:3n-6 is not detectable.

Once 20:3n-6 is generated by the *M. alpina* elongase (MAELO), the Δ5-desaturase can convert it to AA in the desired expression system. To test this hypothesis, the constructs pRAE-5 and pCGR-4 (a Δ5-desaturase containing plasmid) were co-transformed into *S. cerevisiae* 334 and screened for AA production. The substrate used was 25 ③M GLA (18:3n-6). If the *M. alpina* elongase (MAELO) is active in yeast, then the substrate will be converted to DGLA(20:3n-6), which the Δ5-desaturase will convert to AA(20:4n-6). The results in FIG. 11 confirm the production of AA and therefore, the activity of the *M. alpina* elongase (MAELO).

The expression of Δ5-, Δ6-, and Δ12-desaturases, in yeast, along with the elongase, should result in the production of AA (see FIG. 1) without the need for an exogenous supply of fatty acids.

EXAMPLE IV

A Comparison of the Expression of *M. alpina* Elongase cDNA MAELO and *S. cerevisiae* Elongase ELO2 in Baker's Yeast The ELO2 gene encoding for the yeast elongase was cloned from an *S. cerevisiae* genomic library (Origene, Rockville, Md.) using the primers R0514 (5'-GGC TAT GGATCC ATG AAT TCA CTC GTT ACT CAA TAT G-3')(SEQ ID NO:67) and RO515 (5'-CCT GCC AAG CTT TTA CCT TTT TCT TCT GTG TTG AG-3')(SEQ ID NO:68) incorporating the restriction sites (underlined) BamHI and HindIII (respectively). The ELO2 gene was cloned into the vector pYX242 at the BamHI and HindIII sites, designated pRELO, transformed into the S. cerevisiae host 334 (Hoveland et al., supra) and screened for PUFA elongase activity. The vector plasmid was used as a negative control and 334 (pRAE-5) was grown to compare the PUFA elongase activity. The cultures were grown as previously described with no galactose in the media and 25 µM GLA added as a substrate. FIG. 12 shows that amount of 20:3n-6 or DGLA produced (elongated from 18:3n-6 or GLA) by 334 (pRAE-5) was approximately 4 times the negative control containing the unaltered vector pYX242, while the two individual clones 334 (pRELO-1) and 334 (pRELO-2) were only twice the negative control. Additionally, when DGLA produced is expressed as a percent of the total lipids (shown in parenthesis, FIG. 12), the clones 334 (pRELO-1) and 334 (pRELO-2) produced 0.153% and 0.2% DGLA respectively, while 334 (pYX242) produced 0.185% DGLA. Hence all these strains produced comparable percentages of DGLA. The strain 334 (pRAE-5), however, produced 0.279% DGLA, an increase of 50.8% over 334 (pYX242) (negative control). These data show that the S. cerevisiae elongase gene ELO2, even when overexpressed in yeast, does not elongate GLA to DGLA effectively. The M. alpina PUFA elongase activity is specific for this conversion as evidenced by the higher amount of DGLA produced compared to the control, 334 (pYX242).

EXAMPLE V

Identification of Elongases from Other Sources Using MAELO

The TFastA algorithm (Pearson and Lipman, supra) is used to search for similarity between a query peptide sequence and the database DNA sequence translated in each of the six reading frames. Translated MAELO was used as the query for a TFastA search in GCG with the GenEMBL database (6/98) from GCG to identify other potential elongase sequences based on their amino acid similarity comparisons to translated MAELO. For example, in FIGS. 13 and 14, two alignments are shown between translations of two different C. elegans sequences from chromosome III and MAELO. C. elegans DNA sequence (GenBank accession #Z68749) was annotated denoting similarity with GNS1 (ELO2), while the additional C. elegans DNA sequence (GenBank accession # U61954) was noted as similar to both GNS1 and SUR4 (ELO3). These are spliced DNA fragments in which the introns have been removed from the genomic sequence, and the exons assembled and translated. The amount of amino acid identity between the putative PUFA elongases from C. elegans and translated MAELO are around 30%. This would point towards a common function in the fatty acid metabolism, e.g., a PUFA elongase. FIG. 15 is another example of a translated C. elegans sequence (GenBank accession #AF003134) from chromosome III. The DNA sequence was identified that had DNA homology to the S. cerevisiae ELO2. Further inspection of this DNA sequence and its amino acid translation determined that there was homology to translated MAELO. C. elegans, therefore, may contain a PUFA elongase.

FIG. 16 shows the alignments of translated DNA sequences from mouse and human, respectively, with translated MAELO. The mouse sequence CIG30, GenBank accession # U97107, was isolated from brown adipose tissue and reported as being "similar to yeast SUR4 protein". As shown in FIG. 16, amino acids numbered 130 to 152 in the U97107 translation contain a high degree of similarity to the translated MAELO. The human sequence, GenBank accession # AC004050, from chromosome 4 was from an HTGS (High Throughput Genome Sequence). There were no annotations contained with this sequence. However, translated AC004050 had 28.7% identity in 150 amino acids with translated MAELO. This gene fragment could be a fragment of a human PUFA elongase based on its amino acid similarity to translated MAELO.

FIG. 17 shows the amino acid alignment of translated MAELO and a mammalian sequence (GenBank accession # I05465, PCT# WO 88/07577) which claims that the protein derived from expression of this sequence is a glycoslylation inhibition factor. Amino acid identities between the two proteins, signify that there could be related function, such as PUFA elongase activity.

These examples of other translated DNA sequences and their homology to the translated MAELO illustrate that any of the above examples could potentially be a PUFA elongase. These examples are not inclusive of all the possible elongases. However, use of MAELO or its amino acid translation as a query for database searches can identify other genes which have PUFA elongase activities.

EXAMPLE VI

M. alpina cDNA Library Screening Using a Plaque Hybridization Method

In an effort to isolate additional PUFA elongase genes from M. alpina, a conventional plaque hybridization method was used to screen an M. alpina cDNA library made in a lambda vector. The DNA probe was generated based on MAELO nucleotide sequence and was used to screen the M7+8 M. alpina cDNA library made in a λZiplox vector (Knutzon et al., J. Biol. Chem. 273:29360–29366 (1998)).

To make the DNA probe for screening the library, the MAELO cDNA was digested with NspI and PvuI restriction endonucleases. Three small DNA fragments, with an average size of approximately 300 bp, were produced and used as probes. The rationale for using a mixture of fragmented MAELO cDNA was based on the assumption that there might be a common region or domain in the amino acid sequence which is conserved among various PUFA elongases present in M. alpina. Using MAELO DNA probes, the cDNA library was screened by a plaque hybridization technique according to standard protocol (Sambrook et al., Molecular Cloning, 2$^{nd}$ Ed., Cold Spring Harbor, 1989).

Briefly, 50,000 primary clones were plated and transferred to nylon membranes. The membranes were denatured and hybridized with alpha $^{32}$P-dCTP-labelled MAELO DNA probes overnight in the hybridization buffer which contained 20% formamide, 0.2% PVP, BSA, Ficoll, 0.1% SDS and 0.5 M NaCl. The filters were washed with 0.5×SSC at 37° C. and exposed to X-ray film for autoradiography. This procedure was repeated three times. Four clones (designated as F1, F2, F3, and F4) which hybridized repeatedly were picked and suspended in SM buffer (Sambrook et al., supra) containing 7% DMSO.

The largest open reading frame of each candidate was subcloned into yeast expression vector pYX242 (Novagen, Inc., Madison, Wis.). The cDNA clones F1 and F3 were subcloned into pYX242 at the EcoRI site while F2 and F4 were subcloned at NcoI/HindIII sites. The recombinant pYX242 containing each candidate was transformed into SC334 (Hoveland et al., supra) for expression in yeast. To determine the elongase activity, as well as substrate specificity, SC334 containing each cDNA clone was grown in minimal media lacking leucine in the presence of 25 µM of GLA substrate as described in Example III. The fatty acid analysis was performed as described in Knutzon et al. (*J. Biol. Chem.* 273:29360–29366 (1998)). The results indicated that none of these four cDNA clones showed any significant activity in converting GLA to DGLA. Thus, the hybridization approach appeared to be unsuccessful in identifying additional PUFA elongases.

EXAMPLE VII

Construction of Direct cDNA Expression Library of *M. alpina* in Yeast

To identify PUFA elongase genes other than MAELO, a different approach was taken to screen the *M. alpina* cDNA library. In particular, since Baker's yeast is incapable of producing long chain PUFAs due to the absence of respective desaturases and elongases, an attempt was made to construct an expression cDNA library of *M. alpina* in *Saccharomyces cerevisiae*. The vector pYES2 (Novagen, Inc., Madison, Wis.), containing the GAL1 promoter, was chosen for the expression of cDNA library in *S. cerevisiae*.

The conventional way by which a cDNA library is made (i.e. transformation of cDNA/vector ligated DNA mixture into host cells) is difficult in yeast because the transformation efficiency by direct electroporation of ligated DNA mix is very low compared to the efficiency of purified supercoiled plasmid DNA. However, the major advantage of this method is to avoid amplification of primary clones which happens when the library is made in *E. coli* as an intermediate. Due to the limitation in the number of colonies to be screened, it was decided to first optimize the efficiency of transformation in different *S. cerevisiae* strains using cDNA/vector ligated mix. The best results were obtained with a yield of 4–5×10$^5$ transformants per µg of ligated DNA in *S. cerevisiae* strain SC334 (Hoveland et al., supra).

To make a direct *M. alpina* cDNA expression library in yeast total RNA was isolated from the fungus. *M. alpina* fungus (ATCC # 32221) was plated onto cornmeal agar (Difco Laboratories, Detroit, Mich.) and grown at room temperature for 3–4 days. Once fungus growth was visible, it was inoculated into 50 ml of potato dextrose broth and shaken at room temperature very slowly to formulate spores. Once spores were visible, the 50 ml culture was inoculated into a 1 liter culture of potato dextrose, and spores were grown for 72 hours. After filtering through sterile gauze, the cells were immediately frozen into liquid nitrogen for future RNA extraction. Total RNA was prepared from 36 g of cell pellet using the hot phenol/LiCl extraction method (Sambrook et al., supra). The cell pellets were homogenized in a 10 mM EDTA, 1% SDS and 200 mM sodium acetate, pH 4.8 solution. Phenol and chloroform were added to the homogenates, and the aqueous layer was extracted. The aqueous layer was back extracted one more time with phenol and chloroform. Then an equal volume of 4 M lithium chloride was added. The samples were ethanol precipitated on ice for 3 hours, and pellets were obtained by centrifugation. The RNA pellets were washed with 70% ethanol and resuspended in DEPC treated water. Total RNA was quantitated by spectrophotometry and visualized by agarose gel electrophoresis to confirm the presence of 28S and 18S ribosomal bands. Approximately, 15 mg of total RNA were obtained from 36 gram of cell pellet.

The library was constructed according to the standard protocol (Sambrook et. al., *Molecular Cloning*, 2$^{nd}$ Ed. Cold Spring Harbor, 1989). Messenger RNA was prepared from the total RNA using oligo dT cellulose affinity purification. Messenger RNA was reverse transcribed with oligo dT primer containing a XhoI restriction site using AMV reverse transcriptase. Following first strand cDNA synthesis, the second strand of cDNA was synthesized by adding *E. coli* DNA polymerase, *E. coli* DNA ligase and RNAse H.

The EcoRI adaptor was ligated into the blunt-ended cDNA by T4 DNA ligase. The cDNA sample was kinased using T4 polynucleotide kinase and digested with XhoI, diluted with column buffer and passed through a Sephacryl S-400 column. The DNA samples were eluted by high salt buffer. Samples containing DNA from 400–5,000 bps were pooled and used for ligation into a pYES2 vector (Invitrogen Corp., Carlsbad, Calif.). The cDNA was ligated into the EcoRI/XhoI digested pYES2 vector using T4 DNA ligase. A large scale ligation reaction was carried out since a large amount of the ligated DNA (2–3 µg) is required in direct transformation of yeast.

To transform yeast cells directly with the cDNA/pYES2 ligated mixture, competent SC334 cells were prepared using the LiAc TRAFO method (Gietz et. al., *Mol. Cell. Biol,* 5: 255–269, 1995). Briefly, fresh culture of SC334 from the plate was inoculated into 50 ml YPD medium. The culture was grown at 30° C. with shaking until the OD at 600 had reached 1.0. Thirty ml of this starter was inoculated into 300 ml of YPD liquid medium and incubated with shaking until the cell number of the culture reached ~3–5×10$^6$ cell/ml (approximately 3–4 h). The cells were harvested and washed with sterile water. The entire cell pellet was resuspended in 1.5 ml of freshly prepared 1×TE/LiAc (0.1M LiAc). These cells were used immediately for the transformations.

Seven hundred and fifty microliters of competent SC334 cells were aliquoted into 15 ml falcon tubes. Approximately 2 µg of cDNA/pYES2 ligated DNA were added to the cells along with carrier DNA and mixed gently. Three milliliters of sterile 40% PEG/LiAc was added to the cells and mixed gently but thoroughly. The cells were incubated at 30° C. for 30 min with shaking and subsequently given heat shock at 42° C. for 15 min. The cells were cooled, pelleted, and resuspended in 5 ml of 1×TE. A 100 ul aliquot of the above cells was plated onto fifty 150 mm selective agar plates lacking uracil (Ausubel et al., supra) and incubated at 30° C. for 3 days. A total of 8×10$^5$ primary clones were obtained. Five colonies were pooled in 1 ml minimal media lacking uracil (Ausubel et al., supra) and glycerol added to prepare stocks. A total of 5,000 pools were made for screening.

EXAMPLE VIII

MAD (*M. alpina* Direct) Screening in Yeast

The quality of the library was analyzed by determining the average size of the cDNAs in the library. Since the screening of the library was based on the expression of the cDNA, it was important to determine the average size of the cDNA present in the library. The expression library containing the longest cDNAs would be the best appropriate choice to isolate full-length cDNAs of interest. To this end, randomly selected pools were plated onto selective agar plates, as described in Example VII, to obtain individual colonies. Forty different yeast colonies were randomly picked, and each colony was inoculated into 5 ml of selective liquid medium lacking uracil (as described in Example VII) and grown, while shaking, for 24 hours at 30° C. Plasmid DNA was extracted from these colonies by the bead beating method (Hoffman et al., *Gene* 57:267 (1987)) adapted as follows:

Pellets from 5 ml of culture were lysed in 0.5 ml of a 100 mM NaCl, 10 mM Tris, pH 8.0, 1 mM EDTA and 0.1% SDS solution. Sterile 0.5 mm glass beads of equal volume were added and manually vortexed for 3 minutes. Two hundred microliters of the same buffer were added, and the mixture was vortexed for an additional minute. The samples were centrifuged on high for 2 minutes, and cytoplasmic extract was then transferred to a fresh tube. An equal volume of phenol/CHCl$_3$ was added to the sample, vortexed and centrifuged again for 2 minutes. The aqueous layer was re-extracted twice and precipitated with 0.3 M sodium acetate and approximately 2.5 volumes of ethanol for 30 minutes at −20° C. The precipitates were washed with 70% ethanol and resuspended in water. To eliminate RNA and any protein contamination, the plasmid DNAs isolated from 40 different samples were further purified using the QIAprep Spin Miniprep Kit according to the manufacturer's protocol (Qiagen Inc., Valencia, Calif.). The plasmid DNA samples were then restricted with EcoRI and XhoI restriction endonucleases to release the cDNA fragment, and the digest was analyzed on 1% agarose gel. The results indicated that the majority of the cDNAs of the direct library varied in length from 0.8 Kb to 1.5 Kb.

To screen the library, the glycerol stocks were thawed and approximately 0.5 ml was added to 5 ml of liquid selective media lacking uracil (Ausubel et al., supra) and grown at 30° C. for 24 hours. The culture was then transferred into 50 ml of liquid selective medium lacking uracil with 2% galactose and 25 µM GLA (substrate for the elongase enzyme) for 24 hours at 25° C. with shaking. The GC-FAME analysis of the lipid content in the cell pellet of each induced culture was performed as previously described (Knutzon et al., supra). The MAELO (pRAE-5 in pYX242 grown in selective media lacking leucine) was used as a positive control in each batch run. MAELO had consistently been able to convert 1.5% of GLA to DGLA (see Example III).

EXAMPLE IX

Identification of a cDNA Encoding a Potential PUFA Elongase

Figure 19:
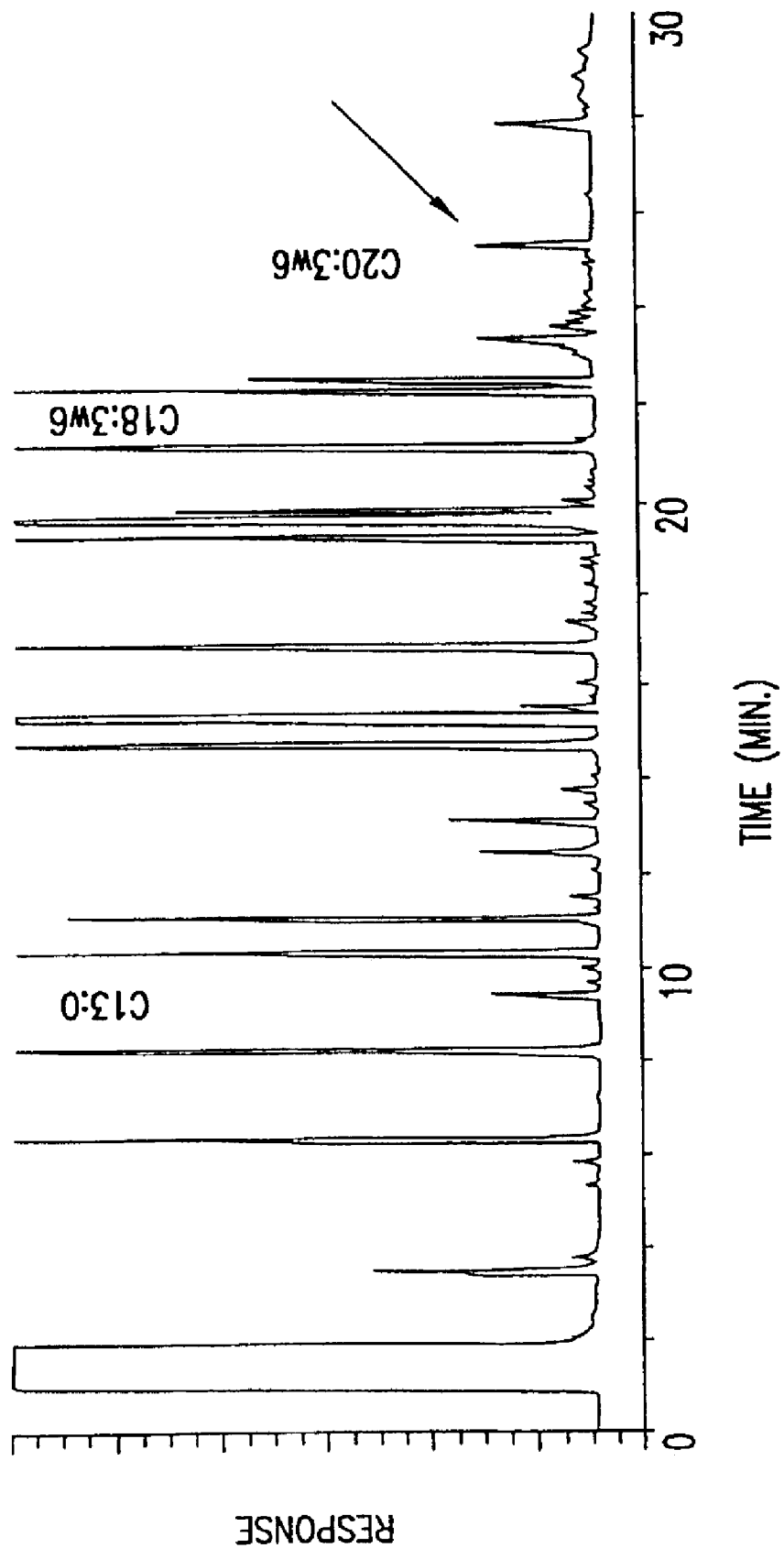
FIG. 19 represents the initial GC-FAME analysis of MAD708 pool. The detection of a DGLA (C20:3n-6) peak should be noted.

After screening and analyzing approximately 750 individual pools by GC-FAME analysis, as described in Example VIII, one pool of five colonies (i.e., MAD708) appeared to have significant enzymatic activity in converting GLA to DGLA. This activity was found to be approximately 5 fold higher than the *M. alpina* elongase activity (MAELO) in terms of DGLA/GLA ratio (FIG. 19). This pool was tested again under identical assay conditions to confirm the initial findings. The repeat experiment showed 9.5% conversion of GLA to DGLA and was again around 5 fold higher than *M. alpina* elongase activity (MAELO). These results strongly indicated that the MAD708 pool contained an elongase candidate which was specific for GLA as substrate. Since MAD708 was a pool of five different clones, it was necessary to isolate the individual cDNA clone which encoded for elongase activity from this pool. To do this, the original MAD708 glycerol stock was plated onto a selective media agar plate lacking uracil (Ausubel et al., supra). Thirty individual colonies were picked and grown in liquid selective medium, lacking uracil with 2% galactose, as previously described in Example VIII, in the presence of GLA. The cell pellet obtained from each culture was then subjected to fatty GC-FAME analysis (Knutzon et al., supra) along with a positive control of 334 (pRAE-5) (MAELO in pYX242). The fatty acid analysis from the 30 individual clones from the MAD708 expression pool in yeast revealed that 5 of the 30 clones showed elongase activity in converting GLA to DGLA. The fatty acid profiles of the active clones MAD708-2, MAD708-10, MAD708-18, MAD708-19 and MAD708-30 are shown in FIG. 20. As shown in this Figure, MAD708-2, 10, and 30 produced the most DGLA, approximately 25 fold more than MAELO (pRAE-5). These 3 converted in the range of 41% to 49% of GLA to DGLA. Other clones, MAD708-18 and MAD708-19, converted 8% and 21% of GLA to DGLA, respectively. All MAD708 clones converted a higher percentage of GLA to DGLA with respect to MAELO encoded elongase (3.4%).

EXAMPLE X

Characterization of cDNAs Encoding Elongase

Plasmid DNA was extracted from SC334 yeast clones (MAD708 pool) that showed significant GLA specific elongase activity by the bead beating method, as described in Example VIII. To determine the size of the cDNA insert, PCR was performed using each plasmid DNA obtained from positive elongase clones as a template. The forward primer RO0541 (5'-GAC TAC TAG CAG CTG TAA TAC-3') and the reverse primer RO0540 (5'-GTG AAT GTA AGC GTG ACA TAA-3') are in the multicloning site of the pYES2 vector and were used to amplify the cDNA insert within the EcoRI and XhoI sites. PCR reaction was performed in a 50 µl volume containing 4 µl of plasmid DNA, 50 pmole of each primer, 5 µl of 10× buffer, 1 µl 10 µM PCR Nucleotide Mix (Boehringer Mannheim Corp., Indianapolis, Ind.) and 0.5 µl of High Five Taq polymerase (Boehringer Mannheim, Indianapolis, Ind.). The amplification was carried out as follows: 2 mins. denaturation at 94° C., then 94° C. for 1 min, 55° C. for 2 mins., and 72° C. for 3 mins. for 30 cycles, and 7 mins. extension at 72° C. at the end of the amplification. Analysis of PCR amplified products on a 1% agarose gel showed the sizes of the elongase cDNAs to be around 1.0 –1.2 Kb. The plasmid DNAs, containing the potential elongase cDNAs, were designated as pRPB2, pRPB10, pRPB18, pRPB19, and pRPB30. Since the cDNA library was made in the pYES2 vector at the EcoRI and XhoI sites, the size of the cDNA present in each plasmid was further confirmed by digesting the above plasmids with EcoRI and XhoI.

The plasmid DNAs isolated from yeast were re-amplified in *E. coli* for long-term storage of the cDNA clones as well as for DNA sequencing. *E. coli* TOP10 (Invitrogen Corp., Carlsbad, Calif.) cells were transformed with the pRPB recombinant plasmids according to the manufacturer's protocol. The transformants obtained from each plasmid DNA were inoculated into LB containing ampicillin (50 µg/ml) and grown overnight at 37° C. with shaking. Plasmid DNAs were isolated from these cultures by using QIAprep Spin Miniprep (Qiagen Inc., Valencia, Calif.) according to the manufacturer's protocol. The purified plasmid DNAs were then used for sequencing from both 5' and 3' ends. The DNA sequencing was performed by using a 373A Stretch ABI automated DNA sequencer (Perkin Elmer, Foster City, Calif.) according to the manufacturer's protocol. Primers used for sequencing were the forward primer RO541 (5'-GAC TAC TAG CAG CTG TAA TAC-3')(SEQ ID NO:69) and the reverse primer RO540 (5'-GTG AAT GTA AGC GTG ACA TAA-3')(SEQ ID NO:70) contained in the multicloning sites of the pYES2 vector. The obtained nucleotide sequences were transferred to Sequencher software program (Gene Codes Corporation, Ann Arbor, Mich.) for analysis.

Figure 21:
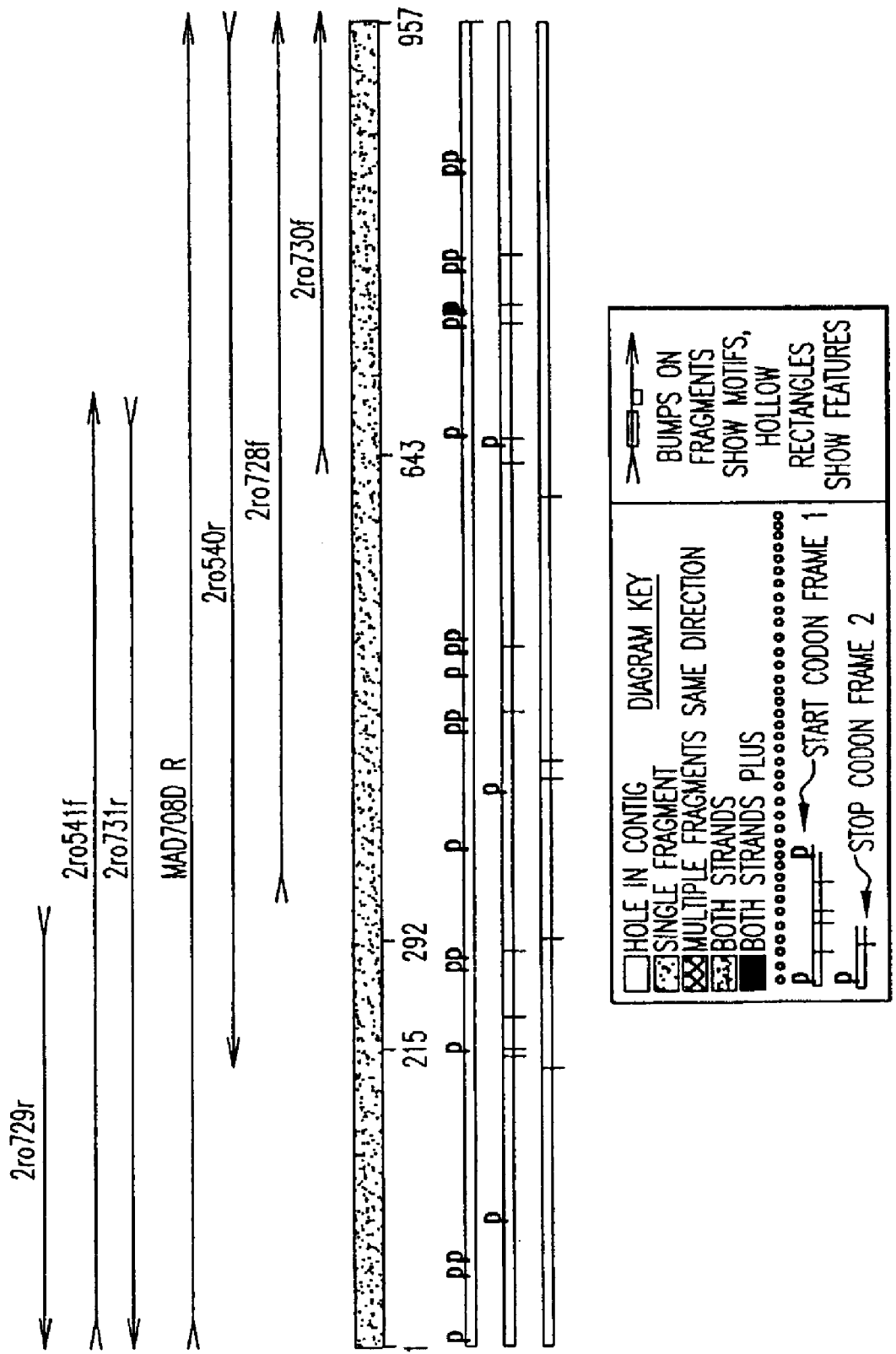
FIG. 21 represents the DNA sequencing analysis of plasmid pRPB2. The analysis reveals an open reading frame of 957 bp in length.

The DNA sequence analysis revealed that all five elongase cDNAs contained the identical nucleotide sequence with a common overlap of 301 nucleotides. Each DNA sequence contains a putative start site at the beginning of the 5' end and a stop codon with poly A tail at the end of the 3' site. To further confirm the DNA sequence, internal forward primers RO728 (5'-GAG ACT TTG AGC GGT TCG-3') (SEQ ID NO:71) and RO730 (5'-TCT CTG CTG CGT TGA ACT CG-3') (SEQ ID NO:72), along with reverse primers RO729 (5'-AAA GCT CTT GAC CTC GAA C-3') (SEQ ID NO:73) and RO731 (5'-AAC TTG ATG AAC GAC ACG TG-3') (SEQ ID NO:74) were designed within the cDNA, and used for sequencing of pRPB2, since this candidate possessed the highest elongase activity. The entire nucleotide sequence was analyzed by the Sequencher program (FIG. 21), and the longest open reading frame deduced from the entire cDNA sequence in pRPB2 appeared to be 957 bp in length (FIG. 22). The deduced open reading frame was then translated into the corresponding amino acid sequence, and the predicted sequence is shown in FIG. 23. The elongase encoded by the cDNA (pRPB2) identified from *M. alpina* appears to be a 318 amino acid long protein which is nearly identical in size with translated MAELO. This new elongase cDNA was designated as "GLELO" and its encoded protein has been named "GLA elongase".

Plasmid DNA pRPB2 was deposited with the American Type Culture Collection, 10801 University Boulevard, Manassas, Va. 20110-2209 on Jul. 22, 1999 under the terms of the Budapest Treaty. It was accorded ATCC Deposit #PTA-402.

EXAMPLE XI

Biochemical Characterization of GLA Elongase (GLELO)

A. Confirmation of GLA Elongase Activity

To further confirm the activity of the GLA elongase encoded by the pRPB2 recombinant plasmid, elongase activity screening was repeated on the yeast clone SC334 containing pRPB2 plasmid. This experiment was also conducted to assure consistent lipid extraction and to detect the activity of GLA elongase by averaging four independent experiments. The *S. cerevisiae* 334 glycerol stock containing pRPB2 was plated onto minimal media agar plates lacking uracil. Individual colonies were randomly picked and grown in minimal medium lacking uracil, as described in Example VIII. The four independent cultures were combined, and a 5 ml aliquot was used as an inoculum for four separate 50 ml cultures. The cultures were then grown in the presence of GLA and were subjected to fatty acid analysis along with a negative control of *S. cerevisiae* 334 containing pYES2, as described in Example VIII. The average elongase activity from four independent cultures of 334 (pRPB2) with 25 µM GLA is shown in FIG. 24. The GLA elongase activity of each of the four independent samples of 334 (pRPB2) appeared to be consistent with an average conversion of 62% GLA to DGLA.

B. Determination of GLELO Substrate Specificity for GLA Elongase

To analyze the substrate specificity of the GLA elongase, the culture of 334 (pRPB2) was tested with different fatty acid substrates besides GLA (e.g., SA(18:0), OA(18:1), LA(18:2n-6), AA(20:4n-6), ADA(22:4n-6), ALA(18:3n-3), STA(18:4n-3), and EPA(20:5n-3)). Under identical assay conditions, the only other substrate utilized by the elongase enzyme was STA, a fatty acid from the n-3 pathway. GLA elongase was able to convert 73% of STA to 20:4n-3 (FIG. 25). From these experiments, it can be concluded that the GLA elongase has substrate specificity for both GLA and STA, indicating that it possesses elongase activity along both the n-6 and n-3 pathways.

C. Co-expression of Fungal CLELO and Δ5-Desaturase Gene in Yeast

Once DGLA (20:3n-6) is produced by the GLA elongase, the Δ5-desaturase can convert it to AA (20:4n-6) in a desired co-expression system. This scheme, as depicted in FIG. 1, can be tested by co-transforming *S. cerevisiae* 334 with plasmids pRPB2 and pRPE31 (the recombinant plasmid pYX242 containing a Δ5-desaturase cDNA (FIG. 18) cloned at the EcoRI site. The co-transformed yeast cultures were supplemented with 25 µM GLA and analyzed for AA synthesis. If both elongase and Δ5-desaturase enzymes are expressed, the GLA substrate will be converted to DGLA, which will then be converted to AA. The results in FIG. 26A indicate that the sequential action of GLA elongase and Δ5-desaturase on GLA substrate resulted in an average conversion of 27% GLA to AA. Therefore, the GLA elongase has the ability to work with other enzymes in the n-6 PUFA synthetic pathway to produce desirable fatty acids.

To determine whether the above conversion is also true in n-3 pathways, the similar co-expression experiments were carried out in the presence of 25 µM STA. Again, if both enzymes are expressed, the STA substrate will be converted to 20:4n-3 which will then be converted to EPA (20:5n-3) by the Δ5-desaturase. FIG. 26B shows the results in which the production of EPA (approx. 40%) is observed. Once again, the GLA elongase demonstrates its ability to work with Δ5-desaturase in the n-3 pathway to produce desirable fatty acids.

EXAMPLE XII

Sequence Comparison Between GLELO and Other Fungal Elongases

The sequence analysis package of GCG (see Example I) was used to compare the GLELO sequence with known protein sequences. The nucleotide sequence of GLELO open reading frame was first translated into amino acid sequence that was used as a query sequence to search Swissprot database (see Example I) using the FastA algorithm (see Example I). Based on amino acid sequence similarity, the best matches were found with *S. cerevisiae* YJT6 (an EST with unknown annotation) with 33.9% identity in 189 amino acid overlap, *S. cerevisiae* ELO2 (GNS1) with 25.8% identity in 295 amino acid overlap, and *S. cerevisiae* ELO3 (SUR4) with 25.2% identity in 313 amino acid overlap. The FastA alignment of GLELO with MAELO showed 30.9% identity in 275 amino acids (FIG. 27). GCG Pileup program creates a multiple sequence alignment from a group of related sequences using progressive, pairwise alignments (see Example I), and was used with the elongases described above. The Pileup results indicate that there are many conserved regions among the elongases including a putative histidine box, which is underlined (Knutzon et. al., *J. Biol. Chem.* 273: 29360–29366, 1998) (FIG. 28). Thus, although GLELO has similarity with MAELO, the difference in their encoded elongases may presumably be due to their substrate preference. GLA elongase can convert a higher percentage of GLA to DGLA than *M. alpina* elongase. In addition, MAELO expression in *S. cerevisiae* showed elongation of saturated and monounsaturated fatty acids in addition to GLA elongation to DGLA (see Example III).

EXAMPLE XIII

Identification of *M. alpina* MAELO Homologues in Mammals The MAELO translated sequence was used to search the Unified Human Transcript Database of Abbott Laboratories, 100 Abbott Park Rd., Abbott Park, Ill. 60064. This database was searched using Basic Local Alignment Search Tool (BLAST) (Altschul et al., *Nuc. Acids Res.* 25:3389–3402 (1997)) which "is a set of similarity search programs designed to explore all of the available sequence databases regardless of whether the query is a protein or DNA." Specifically, the tblastn algorithm was used (i.e., a protein query search to a nucleotide database translated in six reading frames). The contig (CC) sequences in the Unified Human Transcript Database are consensus sequences representing groups of expressed sequence tags (EST) cDNAs derived from the public domain and from the Incyte LIFESEQ™ database of ESTs (Incyte Pharmaceuticals, Inc., 3174 Porter Drive, Palo Alto, Calif. 94304) that are clustered together on the basis of defined sequence homology, and assembled on the basis of sequence overlap. Two sequences from this database, CC067284R1 and CC1484548T1 had 28% identity in 242 amino acid overlap and 28.6% identity in 266 amino acid overlap, respectively, with the translated MAELO sequence. The two derived and edited sequences were designated as hs1 and hs2, respectively, and copied into the sequence analysis software package of GCG (see Example I). The translated MAELO sequence was aligned with translated HS1 (28.5% identity in 242 amino acids) and HS2 (28.2% identity in 266 amino acids) cDNA sequences using the FastA algorithm, as shown in FIGS. 29 and 30, respectively. HS1 cDNA nucleotide sequence also had 86.9% identity in 844 bp with the I05465 nucleotide sequence (see Example V). The translated HS2 cDNA sequence had 100% identity with the amino acid sequence from GenBank with accession number W74824 (see published PCT application WO9839448).

The National Center for Biotechnology Information (NCBI at http://www.ncbi.nlm.nih.gov/) was used to conduct database searches using tblastn with the 28 amino acid sequence (DTIFIILRKQKLTFLHWYHHITVLLYSW)(SEQ ID NO:81) translated from AC004050 (a human sequence identified in a TFastA search, see Example V). This amino acid sequence contains a histidine box (underlined), which has a noted motif of desaturases (Knutzon et al., supra), and both PUFA elongases, MAELO and GLELO (see FIG. 28). A translated mouse sequence shown previously in Example V (GenBank Accession #U97107) and a translated *C. elegans* sequence (GenBank Accession #U41011) had the highest matches with this 28 amino acid query. The NCBI mouse EST database was searched again with tblastn, using translated U41011 as a query. An additional mouse sequence was identified (GenBank Accession #AF014033.1), annotated as "putative involvement in fatty acid elongation." Three longer sequences (GenBank Accession #'s AA591034, AA189549, and AA839346) were identified through a tblastn search of the mouse EST database with translated AF014033.1 and combined into one sequence designated as mm2. The FastA alignment (see Example I) of translated mm2 and MAELO is shown in FIG. 31. Another related, but not identical mouse sequence (GenBank Accession #AI225632), was also identified in a tblastn search of the mouse EST database with AF014033.1. The FastA alignment with translated AI225632 to MAELO is shown in FIG. 32. The percent identity for both translated MM2 and AI 225632 with translated MAELO is 30.4% in 191 and 115 amino acid overlap, respectively. The level of amino acid identity with translated MAELO with these two translated mouse sequences identifies them as putative homologues of PUFA elongases.

EXAMPLE XIV

Identification of *M. alpina* GLELO Homologues in Mammals

The TFastA algorithm, which compares a protein sequence to the database DNA sequence translated in each of the six reading frames, was used with translated GLELO as the query. The GenEMBL database from GCG was used to identify other potential elongase sequences based on their amino acid similarity to translated GLELO. Three human sequences were found to have matches with the GLELO amino acid sequence. These sequences have GenBank accession numbers 1) AI815960, 2) AL034374, and 3) AC004050. AI815960, a *Homo sapien* EST sequence, has 40.3% identity in 144 amino acid overlap with translated GLELO (see FIG. 33). A translated region of the human genomic sequence AL034374, derived from chromosome VI has 46.7% identity in a 60 amino acid overlap with translated GLELO. This homologous region in AL034374 appeared to be a part of the HS1 amino acid sequence which was shown to have homology with translated MAELO (see Example XIII). Therefore, HS1 sequence has similarity with both MAELO (see FIG. 29) as well as GLELO (see FIG. 34). A translated region of a human genomic sequence AC004050 from chromosome IV has 34.8% identity in 89 amino acid overlap with translated GLELO (see FIG. 35). The amino acid identities between GLELO and these human sequences indicate that the proteins derviced from these human sequences could have related function, such as PUFA elongase activity.

To identify a mouse cDNA similar to GLELO, TFastA searches were performed with the GenEMBL database using translated GLELO as a query. From the TFastA searches, the three mouse sequences with the highest matches to translated GLELO were identified: (GenBank accession numbers 1) AF104033, 2) AI595258, and 3) U97107). AF104033 is annotated as "MUEL protein having putative fatty acid elongase with homology to yeast ELO3 (SUR4)" and is a part of the sequence of MM2. The MM2 sequence was initially derived from AF104033 mouse sequence, but the entire MM2 sequence was finally obtained through further mouse EST database searches and also shown to have homology with translated MAELO (see Example XIII and FIG. 31). When this MM2 amino acid sequence was aligned with translated GLELO sequence using FastA, a 34.6% identity in 211 amino acid overlap was found (see FIG. 36) indicating that MM2 also has homology with GLELO. AI595258 is a mouse cDNA clone having 5' similarity with yeast ELO3 elongase and is part of mouse EST cDNA AI225632. The AI225632 mouse sequence, which is a longer sequence than AI595258, was shown to have similarity with translated MAELO (see FIG. 32). The AI225632 was also aligned with the translated GLELO, and the FastA alignment is shown in FIG. 37. A 35.3% identity in 199 amino acid overlap has been found. The third sequence, U97107, a mouse sequence, was annotated as "similar to yeast ELO3 (SUR4) gene." The FastA alignment of translated GLELO with U97107 is shown in FIG. 38 where a 23.7% identity in 279 amino acid overlap was found. Previously, a region of U97107 was also found to have a high degree of homology with MAELO based on a FastA alignment (see Example V and FIG. 16).

The above searches clearly indicate that the same human and mouse sequences were obtained by using either MAELO or GLELO as a query.

EXAMPLE XV

Identification of *M. alpina* GLELO and MAELO Homologues in Other PUFA Producing Organisms A) *Caenorhabditis elegans:*

A putative amino acid sequence deduced from a chromosomal sequence of *C. elegans* (GenBank Accession #U41011) was able to identify a partial sequence contained in the mouse MM2 putative PUFA elongase which has amino acid similarity with both GLA elongase (GLELO) and *M. alpina* elongase (MAELO). It was therefore conceivable that *C. elegans* homologues of GLELO or MAELO might be present in the nematode database. The putative amino acid sequences derived from GLELO and MAELO sequences were used as queries independently to search the nematode databases. A BLAST search (see Example XIII) was performed on wormpep16 (blastp compares an amino acid query sequence against a nucleotide sequence database) and wormpep 16cDNAs (tblastn) databases which are predicted proteins and cDNAs obtained from the *C. elegans* genome sequencing project or EST's and their corresponding cDNA sequences, respectively. These sequence data were produced by the *C. elegans* Sequencing group, carried out jointly by the Sanger Centre and Genome Sequencing Center, and can be obtained from ftp://ftp.sanger.ac.uk/pub/databases/wormpep/. At least seven putative *C. elegans* translated sequences were identified by their amino acid sequence homology to the translated amino acid sequence of both GLELO and MAELO. The GenBank Accession #'s of those genomic sequences containing the deduced amino acids were identified as Z19154, U68749 (2 deduced proteins (F56H11.4 and F56H11.3 (wormpep Accession #'s)), U41011, U61954 (2 deduced proteins (F41H10.7 and F41H10.8 (wormpep Accession #'s)), and Z81058. Those underlined were identified in a previous search using translated MAELO as query (see Example V). As an example, the FastA amino acid alignments of translated U68749 (F56H11.4) with translated GLELO and MAELO are shown in FIGS. 39 and 40. Translated U68749 (F56H11.4) has 25–30% identity with both *M. alpina* elongase and GLA elongase in approximately a 200 amino acid overlap (see FIGS. 39 and 40). For all seven translated putative *C. elegans* cDNAs, the FastA alignments to translated GLELO was between 25–30% identity in a 200 amino acid overlap, while the identity was 26–34% in at least a 188 amino acid overlap for translated MAELO. The alignment similarities indicate that either translated GLELO or MAELO can be used to identify potential genes from *C. elegans* with elongase activity.

B) *Drosophila melanogaster:*

The translated deduced cDNA from the genomic sequence U41011 (*C. elegans*) had its highest match with a *Drosophila melanogaster* EST, accession number AI134173 in a blastn search (compares a nucleotide query sequence against a nucleotide database) of the "other ESTs" database through NCBI (see Example XIII) and was assembled with an overlapping DNA EST fragment, accession number A1517255. The translated DNA fragment DM1, derived from the two overlapping sequences was aligned with translated GLELO as well as MAELO (see FIGS. 41 and 42) using FastA in GCG (see Example I). The alignments showed 27.2% identity with GLA elongase in a 206 amino acid overlap and 30% identity with *M. alpina* elongase in a 237 amino acid overlap. Thus, based on amino acid similarity, the DM1 could be a potential homologue to GLELO or MAELO having PUFA elongase-like activity. Moreover, using DNA sequences of GLELO and MAELO as queries for database searches, homologues with PUFA elongase activity from *Drosophila* can be identified

EXAMPLE XVI

Cloning and Expression of a Human PUFA Elongase Homologue

Many potential PUFA elongase sequences were identified based on their amino acid similarities to translated GLELO and/or MAELO. To determine the potential elongase activities of these sequences, the cDNA encoding the full length protein is then identified, cloned, and expressed, as demonstrated in the present example.

Primers RO0719 (5'-GGT TCT CCC ATG GAA CAT TTT GAT GCA TC-3') (SEQ ID NO:75) and RO720 (5'-GGT TTC AAA GCT TTG ACT TCA ATC CTT CCG-3') (SEQ ID NO:76) were designed based on the putative HS1 sequence, and used to amplify the human liver Marathon-Ready cDNA (Clontech Laboratories, Inc., Palo Alto, Calif.). The polymerase Chain Reaction (PCR) was carried out in a 50 µl volume containing: 5 µl of human liver Marathon-Ready cDNA, 50 pmole each primer, 1 µl 10 mM PCR Nucleotide Mix (Boehringer Mannheim Corp., Indianapolis, Ind.), 5 µl 10× buffer and 1.0 U of Advantage KlenTaq Polymerase Mix (Clontech Laboratories, Inc., Palo Alto, Calif.). Thermocycler conditions in Perkin Elmer 9600 (Norwalk, Conn.) were as follows: 94° C. for 2 mins, then 30 cycles of 94° C. for 1 min., 58° C. for 2 mins, and 72° C. for 3 mins. PCR was followed by an additional extension cycle at 72° C. for 7 minutes.

The PCR amplified product was run on a gel, an amplified fragment of approximately 960 bp was gel purified, the termini of the fragment filled-in with T4 DNA polymerase (Boehringer Mannheim, Corp., Indianapolis, Ind.), and cloned into pCR-Blunt Vector (Invitrogen Corp., Carlsbad, Calif.) following manufacturer's protocol. The new plasmid was designated as pRAE-52, and the putative PUFA elongase cDNA in this clone was sequenced using ABI 373A Stretch DNA Sequencer (Perkin Elmer, Foster City, Calif.). The putative PUFA elongase cDNA sequence in plasmid pRAE-52 is shown in FIG. 43, and the translated sequence is shown in FIG. 44.

The putative PUFA elongase cDNA from plasmid pRAE-52 was then digested with NcoI/HindIII, gel purified, and ligated into pYX242 (NcoI/HindIII). The new plasmid was designated as pRAE-58-A1. (Plasmid 58-A1 was deposited with the American Type Culture Collection, 10801 University Boulevard, Manassas, Va. 20110–2209 on Aug. 20, 1999, under the terms of the Budapest Treaty and was accorded deposit number PTA 566.)

The construct pRAE-58-Al was transformed into *S. cerevisiae* 334 (Hoveland et al., supra) and screened for elongase activity. The negative control strain was *S. cerevisiae* 334 containing pYX242 vector. The cultures were grown for 24 hours at 30° C., in selective media (Ausubel et al., supra), in the presence of 25 µM of GLA or AA. In this study, DGLA or adrenic acid (ADA, 22:4n-6), respectively, was the predicted product of human elongase activity. When GLA was used as a substrate, the yeast cells containing the human elongase cDNA contained elevated levels of DGLA compared to control cells, 2.75% vs. 0.09% of total fatty acids, respectively (see FIG. 45). When AA was used as a substrate, the yeast cells containing the human elongase cDNA contained elevated levels of ADA compared to control cells, none detected vs. 1.21% of total fatty acids, respectively. Thus, the human elongase converts both 18 and 20 carbon chain long PUFAs to their respective elongated fatty acids.

The yeast cells containing the human elongase cDNA also had elevated levels of monounsaturated fatty acids including 18:1n-7, 20:1n-7, 20:1n-9, and 18:1n-5, compared to the control strain. Therefore, these results indicate that the identified human elongase is capable of utilizing PUFAs as well as monounsaturated fatty acids as substrates. Thus, this human sequence HSELO1, and its encoded protein, possess elongase activity independent of substrate specificity.

EXAMPLE XVII

Cloning and Expression of a *C. elegans* PUFA Elongase

Several putative *C. elegans* elongases were identified with amino acid homology to both translated GLELO and MAELO. As with the human cDNA sequence, cloning of a cDNA and expression in yeast was used to determine if indeed it was a PUFA elongase. Primers RO738 (5'-AAT CAG <u>GAA TTC</u> ATG GCT CAG CAT CCG CTC GTT CAA C-3') (SEQ ID NO:77) and RO739 (5'-CCG CTT <u>GTC GAC</u> TTA GTT GTT CTT CTT CTT TGG CAC-3') (SEQ ID NO:78) with restriction sites EcoRI and SalI (underlined), respectively, were based on the putative cDNA sequence contained in the genomic sequence U68749 (wormpep cDNA accession #F56H11.4.) A PCR amplification was performed in a 100 µl volume containing: 250 ng excised *C. elegans* library cDNA (OriGene Technologies Inc., Rockville, Md.), 50 pmole each primer, 10 µl 10× reaction buffer (Boehringer Mannheim Corp., Indianapolis, Ind.), 1 µl 10 mM PCR Nucleotide mix (Boehringer Mannheim Corp., Indianapolis, Ind.), and 2.5 U Taq polymerase (Boehringer Mannheim Corp., Indianapolis, Ind.). Thermocycler conditions in a Perkin Elmer 9600 (Norwalk, Conn.) were as follows: 95° C. for 5 mins, then 25 cycles of 94° C. for 30 secs, 55° C. for 2 mins, and 72° C. for 2 mins. PCR was followed by an additional cycle of 72° C. for 7 minutes.

The PCR amplified product was purified from an agarose gel, cut with EcoRI and SalI, ligated to pYX242 (Invitrogen Corp., Carlsbad, Calif.) (linearized with EcoRI and SalI) using the Rapid Ligation kit (Boehringer Mannheim Corp., Indianapolis, Ind.), according to the manufacturer's protocol and transformed into *E. coli* Top10 cells (Invitrogen Corp., Carlsbad, Calif.). The new plasmids, designated pRET-21 and pRET-22 (two individual clones from the ligation), were sequenced with the 373A Stretch DNA sequencer ABI (Perkin Elmer, Foster City, Calif.), and the cDNA sequences were identical. The 867 base cDNA nucleotide sequence of the plasmid pRET-22 containing the putative elongase is shown in FIG. 46 and the translated sequence of 288 amino acids is shown in FIG. 47. (Plasmid pRET-22 was deposited with the American Type Culture Collection, 10801 University Boulevard, Manassas, Va. 20110-2209 on Aug. 20, 1999, under the terms of the Budapest Treaty and was accorded deposit number PTA 565.)

The plasmids pRET-21 and -22 were transformed into *S. cerevisiae* 334 as previously described (see Example III) and the resulting yeast cultures (334 (pRET-21) and 334 (pRET-22)) grown in 100 ml of selective media without leucine (Ausubel et al, supra) for 48 hours at 20° C. in the presence of 50 ③M GLA and AA. The cell pellets were collected and subjected to fatty acid analysis and the results shown in FIG. 48. DGLA, the predicted product from GLA elongation, was found to be an average of 1.79% of the total lipid in the two samples, versus 0.13% for the negative control (334 containing plasmid pYX242) indicating that the enzyme encoded by both pRET-21 and pRET-22 possessed GLA elongase activity. The percent conversion of GLA to DGLA by 334 (pRET-21) and 334 (pRET-22) was 11.1% and 19.4% respectively with an average of 15.25%. Interestingly, almost no elongation of AA or any endogenous fatty acid was observed (FIG. 48). These results indicate that the elongase encoded by this newly identified *C. elegans* cDNA, CEELO1, is able to specifically elongate GLA to DGLA, suggesting that it may be a *C. elegans* homologue of GLA elongase.

EXAMPLE XVIII

Isolation of a Putative Human Elongase cDNA Based on AC004050 Sequence

To isolate the full length putative elongase cDNA based on the AC004050 sequence, primers RP735 (5'-CCT CCT GAA TTC CAA CAC TAT TCA GCT TTC-3') (SEQ ID NO:79) and RO73 (5'-TAA TAC GAC TCA CTA TAG GG-3') (SEQ ID NO:80) were used to PCR amplify the human liver Marathon-Ready cDNA (Clontech Laboratories, Inc., Palo Alto, Calif.). The PCR was carried out using the Advantage™ cDNA PCR Kit (Clontech Laboratories, Inc., Palo Alto, Calif.) with 5 µl of human liver Marathon-Ready cDNA and 50 pmole each primer following manufacturer's instructions. Thermocycler conditions in Perkin Elmer 9600 (Norwalk, Conn.) were as follows: 94° C. for 2 mins, then 30 cycles of 94° C. for 1 min., 58° C. for 2 mins., and 72° C. for 3 mins. PCR was followed by an additional extension at 72° C. for 7 mins.

The PCR amplified product was run on a gel, an amplified fragment of approximately 1 Kb was gel purified, the termini of the fragment were filled in with T4DNA polymerase (Boehringer Mannheim, Corp., Carlsbad, Calif.) following manufacturer's instructions. The new plasmid was designated as pRAE-59, and the putative PUFA elongase cDNA in this plasmid, designated as HS3, was sequenced using the ABI 373A Stretch Sequencer (Perkin Elmer, Foster City, Calif.). The putative PUFA elongase cDNA sequence HS3 is shown in FIG. 49, and the translated sequence is shown in FIG. 50.

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: lactase deficiency, lactose intolerance and galactosemia.

Features:

Soy protein isolate to avoid symptoms of cow's-milk-protein allergy or sensitivity.

Lactose-free formulation to avoid lactose-associated diarrhea.

Low osmolality (240 mOs/kg water) to reduce risk of osmotic diarrhea.

Dual carbohydrates (corn syrup and sucrose) designed to enhance carbohydrate absorption and reduce the risk of exceeding the absorptive capacity of the damaged gut.

1.8 mg of Iron (as ferrous sulfate) per 100 Calories to help prevent iron deficiency.

Recommended levels of vitamins and minerals.

Vegetable oils to provide recommended levels of essential fatty acids.

Milk white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula for Diarrhea:

Usage: As a short-term feeding for the dietary management of diarrhea in infants and toddlers.

Features:

First infant formula to contain added dietary fiber from soy fiber specifically for diarrhea management.

Clinically shown to reduce the duration of loose, watery stools during mild to severe diarrhea in infants.

Nutritionally complete to meet the nutritional needs of the infant.

Soy protein isolate with added L-methionine meets or exceeds an infant's requirement for all essential amino acids.

Lactose-free formulation to avoid lactose associated diarrhea.

Low osmolality (240 mOsm/kg water) to reduce the risk of osmotic diarrhea.

Dual carbohydrates (corn syrup and sucrose) designed to enhance carbohydrate absorption and reduce the risk of exceeding the absorptive capacity of the damaged gut.

Meets or exceeds the vitamin and mineral levels recommended by the Committee on Nutrition of the American Academy of Pediatrics and required by the Infant Formula Act.

1.8 mg of iron (as ferrous sulfate) per 100 Calories to help prevent iron deficiency.

Vegetable oils to provide recommended levels of essential fatty acids.

Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron:

Usage: As a beverage for infants, children and adults with an allergy or sensitivity to cow's-milk protein or an intolerance to sucrose. A feeding for patients with disorders for which lactose and sucrose should be avoided.

Features:

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron (as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula with Iron Ready to Feed, 20 Cal/fl oz.:

Usage: When a soy feeding is desired.

Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:

Usage: When an infant formula is needed: if the decision is made to discontinue breastfeeding before age 1 year, if a supplement to breastfeeding is needed or as a routine feeding if breastfeeding is not adopted.

Features:

Protein-of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® NeoCare Premature Infant Formula with Iron:

Usage: For premature infants' special nutritional needs after hospital discharge. Similac NeoCare is a nutritionally complete formula developed to provide premature infants with extra calories, protein, vitamins and minerals needed to promote catch-up growth and support development.

Features:

Reduces the need for caloric and vitamin supplementation. More calories (22 Cal/fl oz) than standard term formulas (20 Cal/fl oz).

Highly absorbed fat blend, with medium-chain triglycerides (MCT oil) to help meet the special digestive needs of premature infants.

Higher levels of protein, vitamins and minerals per 100 calories to extend the nutritional support initiated in-hospital.

More calcium and phosphorus for improved bone mineralization.

Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready to Use, 24 Cal/fl oz.:

Usage: Designed to be mixed with human milk or to be fed alternatively with human milk to low-birth-weight infants.

Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carhitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. ENSURE®

Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.

Patient Conditions:

For patients on modified diets

For elderly patients at nutrition risk

For patients with involuntary weight loss

For patients recovering from illness or surgery

For patients who need a low-residue diet

Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS:

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:

For patients who need extra calories, protein, vitamins and minerals.

Especially useful for people who do not take in enough calories and nutrients.

For people who have the ability to chew and swallow

Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

Partially hydrogenated cottonseed and soybean oil 76%

| Partially hydrogenated cottonseed and soybean oil | 76% |
|---|---|
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| High-fructose corn syrup | 24% |
|---|---|
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN:

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:

For patients who require additional calories, protein, vitamins, and minerals, such as patients recovering from general surgery or hip fractures, patients at risk for pressure ulcers, and patients on low-cholesterol diets Features:

Low in saturated fat

Contains 6 g of total fat and <5 mg of cholesterol per serving

Rich, creamy taste

Excellent source of protein, calcium, and other essential vitamins and minerals

For low-cholesterol diets

Lactose-free, easily digested

Ingredients:

Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:

The protein source is a blend of two high-biologic-value proteins: casein and soy.

| Sodium and calcium caseinates | 85% |
|---|---|
| Soy protein isolate | 15% |

Fat:

The fat source is a blend of three oils: high-oleic safflower, canola, and soy.

| High-oleic safflower oil | 40% |
|---|---|
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate:

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in-pecan, cherry, strawberry, lemon, and orange, help to prevent flavor fatigue and aid in patient compliance.

Vanilla and other nonchocolate flavors:

| Sucrose | 60% |
|---|---|
| Maltodextrin | 40% |

Chocolate:

| Sucrose | 70% |
|---|---|
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:

For normal-weight or overweight patients who need extra nutrition in a supplement that contains 50% less fat and 20% fewer calories than ENSURE.

For healthy adults who don't eat right and need extra nutrition.

Features:

Low in fat and saturated fat

Contains 3 g of total fat per serving and <5 mg cholesterol

Rich, creamy taste

Excellent source of calcium and other essential vitamins and minerals

For low-cholesterol diets

Lactose-free, easily digested

Ingredients:

French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride-Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:

The protein source is calcium caseinate.

| | |
|---|---|
| Calcium caseinate | 100% |

Fat:

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Sucrose | 51% |
| Maltodextrin | 49% |

Chocolate:

| | |
|---|---|
| Sucrose | 47.0% |
| Corn Syrup | 26.5% |
| Maltodextrin | 26.5% |

Vitamins and Minerals:

An 8-fl-oz serving of ENSURE LIGHT provides at least 25% of the RDIs for 24 key vitamins and minerals.

Caffeine:

Chocolate flavor contains 2.1 mg caffeine/8 fl oz.

E. ENSURE PLUS®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:

For patients who require extra calories and nutrients, but a normal concentration of protein, in a limited volume For patients who need to gain or maintain healthy weight Features:

Rich, creamy taste

Good source of essential vitamins and minerals

Ingredients:

Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein:

The protein source is a blend of two high-biologic-value proteins: casein and soy.

| | |
|---|---|
| Sodium and calcium caseinates | 84% |
| Soy protein isolate | 16% |

Fat:

The fat source is corn oil.

| | |
|---|---|
| Corn oil | 100% |

Carbohydrate:

ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, Strawberry, Butter Pecan, and Coffee Flavors:

| | |
|---|---|
| Corn Syrup | 39% |
| Maltodextrin | 38% |
| Sucrose | 23% |

Chocolate and Eggnog Flavors:

| | |
|---|---|
| Corn Syrup | 36% |
| Maltodextrin | 34% |
| Sucrose | 30% |

Vitamins and Minerals:
An 8-fl-oz serving of ENSURE PLUS provides at least 15% of the RDIs for 25 key Vitamins and minerals.
Caffeine:
Chocolate flavor contains 3.1 mg Caffeine/8 fl oz. Coffee flavor contains a trace amount of caffeine.
F. ENSURE PLUS® HN
Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.
Patient Conditions:
  For patients with increased calorie and protein needs, such as following surgery or injury.
  For patients with limited volume tolerance and early satiety.
Features:
  For supplemental or total nutrition
  For oral or tube feeding
  1.5 CaVmL,
  High nitrogen
  Calorically dense
Ingredients:
  Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.
G. ENSURE® POWDER:
Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.
Patient Conditions:
  For patients on modified diets
  For elderly patients at nutrition risk
  For patients recovering from illness/surgery
  For patients who need a low-residue diet
Features:
  Convenient, easy to mix
  Low in saturated fat
  Contains 9 g of total fat and <5 mg of cholesterol per serving
  High in vitamins and minerals
  For low-cholesterol diets
  Lactose-free, easily digested
Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.
Protein:
The protein source is a blend of two high-biologic-value proteins: casein and soy.

| | |
|---|---|
| Sodium and calcium caseinates | 84% |
| Soy protein isolate | 16% |

Fat:
The fat source is corn oil.

| | |
|---|---|
| Corn oil | 100% |

Carbohydrate:
ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

| | |
|---|---|
| Corn Syrup | 35% |
| Maltodextrin | 35% |
| Sucrose | 30% |

H. ENSURE® PUDDING
Usage: ENSURE PUDDING is a nutrient dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.
Patient Conditions:
  For patients on consistency-modified diets (e.g., soft, pureed, or full liquid)
  For patients with swallowing impairments
Features:
  Rich and creamy, good taste
  Good source of essential vitamins and minerals
  Convenient-needs no refrigeration
  Gluten-free
  Nutrient Profile per 5 oz: Calories 250, Protein 10.9%, Total Fat 34.9%, Carbohydrate 54.2%
Ingredients:
  Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.

Protein:

The protein source is nonfat milk.

| Nonfat milk | 100% |
|---|---|

Fat:

The fat source is hydrogenated soybean oil.

| Hydrogenated soybean oil | 100% |
|---|---|

Carbohydrate:

ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and Other Nonchocolate Flavors:

| Sucrose | 56% |
|---|---|
| Lactose | 27% |
| Modified food starch | 17% |

Chocolate:

| Sucrose | 58% |
|---|---|
| Lactose | 26% |
| Modified food starch | 16% |

I. ENSURE® WITH FIBER:

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:

For patients who can benefit from increased dietary fiber and nutrients

Features:

New advanced formula-low in saturated fat, higher in vitamins and minerals

Contains 6 g of total fat and <5 mg of cholesterol per serving

Rich, creamy taste

Good source of fiber

Excellent source of essential vitamins and minerals

For low-cholesterol diets

Lactose- and gluten-free

Ingredients:

Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein:

The protein source is a blend of two high-biologic-value proteins-casein and soy.

| Sodium and calcium caseinates | 80% |
|---|---|
| Soy protein isolate | 20% |

Fat:

The fat source is a blend of three oils: high-oleic safflower, canola, and corn.

| High-oleic safflower oil | 40% |
|---|---|
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of $\leq$30% of total calories from fat, <10% of the calories from saturated fatty acids, and $\leq$10% of total calories from polyunsaturated fatty acids.

Carbohydrate:

ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and Other Nonchocolate Flavors:

| Maltodextrin | 66% |
|---|---|
| Sucrose | 25% |
| Oat Fiber | 7% |
| Soy Fiber | 2% |

Chocolate:

| Maltodextrin | 55% |
|---|---|
| Sucrose | 36% |
| Oat Fiber | 7% |
| Soy Fiber | 2% |

Fiber:

The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs.

The distribution of Calories in Oxepa is shown in Table IV.

TABLE IV

Caloric Distribution of Oxepa

|  | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table V.

Oxepa provides a balanced amount of polyunsaturated, monounsaturated, and saturated fatty acids, as shown in Table VI.

Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE V

Typical Fatty Acid Profile

|  | % Total Fatty Acids | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapentaenoic | 0.55 | 0.12 | 0.49 |

TABLE V-continued

Typical Fatty Acid Profile

|  | % Total Fatty Acids | g/8 fl oz* | 9/L* |
|---|---|---|---|
| Docosahexaenoic | 2.27 | 0.48 | 2.02 |
| Others | 7.55 | 1.52 | 6.72 |

Fatty acids equal approximately 95% of total fat.

TABLE VI

Fat Profile of Oxepa.

| % of total calories from fat | 55.2 |
|---|---|
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/ 8 fl oz |
|  | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

*Oxepa is gluten-free.

Default Settings for the Analysis Programs
GCG Programs

FastA Search

Default parameters:
range of interest    Begin = 1         END = last protein or nucleic acid
search set                             all of SwissProt (protein) or GenEMBL (nucleic acid)
word size =          (2) for protein = (6) for nucleic acid
Expected scores     lists scores until E( ) value reaches 2.0

TFastA search

Default parameters:
range of interest    Begin = 1         END = last nucleic acid
search set                             all of GenEMBL
word size                              wordsize = (2)
Expected scores     lists scores until E() value reaches 2.0

Pileup

Default parameters:
gap creation penalty      gap weight = 5
gap extension penalty     gap length weight = 12
plot figure               one page plot density = 2.7

Sequencher Program

Default parameters:
Automatic Assembly    Dirty data algorithm = slower contig assembly but more rigorous comparisons between the sequences
                      minimum match = 85%
                      minimum overlap = 20

BLAST 2 (blastp, tblastn)

Default parameters:    V = 50    Lambda = .329    W = 3
                       B = 50    K = 0.140        X = 22
                       E = 10    H = 0.427 blast n
Default parameters:    V = 100   Lambda = 1.37    W = 11
                       B = 250   K = 0.171        X1 = 22
                       E = 10    H = 1.31         X2 = 25

BLAST 2 Command Line Arguments

-v Hits                number of best scores to show
-b Alignments          number of best alignments to show
-e Expectation value (E)    [Real] default = 10.0
-m Alignment view options:  0 = pairwise,
                            1 = master-slave showing identities,
                            2 = master-slave, no identities,
                            3 = flat master-slave, show identities,
                            4 = flat master-slave, no identities,
                            5 = master-slave, no identities and blunt ends,
                            6 = flat master-slave, no identities and blunt ends [Integer]
                            default = 0
-F Filter query seq.   (DUST with blastn, SEG with others)
[T/F]
                       default = T
-G Cost to open a gap   (zero invokes default behavior) [Integer]
                       default = 0
-E Cost to extend a gap   (zero invokes default behavior) [Integer]
                       default = 0
-X X dropoff value for gapped alignment (in bits) (zero invokes default behavior) [Integer]
                       default = 0
-I Show GI's in deflines    [T/F]
                       default = F
-q Penalty for a nucleotide mismatch    (blastn only) [Integer]
                       default = −3
-r Reward for a nucleotide match    (blastn only) [Integer]
                       default = 1
-f Threshold for extending hits    default if zero [Integer]
                       default = 0
-g Perfom gapped alignment (not available with tblastx) [T/F]
                       default = T
-q Query Genetic code to use    [Integer] use
                       default = 1
-D DB Genetic code    (for tblast[nx] only) [Integer]
                       default = 1
-J Believe the query defline    [T/F]
                       default = F
-M Matrix                       [String]
                       default = BLOSUM62
-W Word size            default if zero [Integer]
                       default = 0
-z Effective length of the database (use zero for the real size) [Integer]
                       default = 0
-a Number of processors to use    [Integer]
                       default = site configurable (SeqServer.conf)

Allowed and default values for gap open/gap extension cost (-G/-E) parameters:

BLOSUM62

| | | | | | | | | | | | |
|---|---|---|---|---|---|---|---|---|---|---|---|
| -G | 9 | 8 | 7 | 12 | 11 | 10 | | | | | |
| -E | 2 | 2 | 2 | 1  | 1  | 1  | | | | | |

BLOSUM50

| | | | | | | | | | | | |
|---|---|---|---|---|---|---|---|---|---|---|---|
| -G | 12 | 11 | 10 | 9 | 15 | 14 | 13 | 12 | 18 | 17 | 16 | 15 |
| -E | 3  | 3  | 3  | 3 | 2  | 2  | 2  | 2  | 1  | 1  | 1  | 1  |

PAM250

| | | | | | | | | | | | |
|---|---|---|---|---|---|---|---|---|---|---|---|
| -G | 13 | 12 | 11 | 10 | 15 | 14 | 13 | 12 | 19 | 18 | 17 | 16 |
| -E | 3  | 3  | 3  | 3  | 2  | 2  | 2  | 2  | 1  | 1  | 1  | 1  |

BLOSUM90

| | | | | | | | |
|---|---|---|---|---|---|---|---|
| -G | 8 | 7 | 6 | 11 | 10 | 9 |
| -E | 2 | 2 | 2 | 1  | 1  | 1 |

PAM30

| | | | | | | | | |
|---|---|---|---|---|---|---|---|---|
| -G | 5 | 4 | 3 | 7 | 6 | 5 | 10 | 9 | 8 |
| -E | 3 | 3 | 3 | 2 | 2 | 2 | 1  | 1 | 1 |

PAM70

| | | | | | | | | |
|---|---|---|---|---|---|---|---|---|
| -G | 6 | 5 | 4 | 8 | 7 | 6 | 11 | 10 | 9 |
| -E | 3 | 3 | 3 | 2 | 2 | 2 | 1  | 1  | 1 |

SEQUENCE LISTING

<160> NUMBER OF SEQ ID NOS: 81

<210> SEQ ID NO 1
<211> LENGTH: 954
<212> TYPE: DNA
<213> ORGANISM: Mortierella alpina

<400> SEQUENCE: 1

| | | | | | |
|---|---|---|---|---|---|
| atggccgccg | caatcttgga | caaggtcaac | ttcggcattg | atcagccctt | cggaatcaag | 60 |
| ctcgacacct | actttgctca | ggcctatgaa | ctcgtcaccg | aaagtccat | cgactccttc | 120 |
| gtcttccagg | agggcgtcac | gcctctctcg | acccagagag | aggtcgccat | gtggactatc | 180 |
| acttacttcg | tcgtcatctt | tggtggtcgc | cagatcatga | gagccagga | cgccttcaag | 240 |
| ctcaagcccc | tcttcatcct | ccacaacttc | ctcctgacga | tcgcgtccgg | atcgctgttg | 300 |
| ctcctgttca | tcgagaacct | ggtccccatc | ctcgccagaa | acggactttt | ctacgccatc | 360 |
| tgcgacgacg | gtgcctggac | ccagcgcctc | gagctcctct | actacctcaa | ctacctggtc | 420 |
| aagtactggg | agttggccga | caccgtcttt | ttggtcctca | agaagaagcc | tcttgagttc | 480 |
| ctgcactact | ccaccactc | gatgaccatg | gttctctgct | ttgtccagct | tggaggatac | 540 |
| acttcagtgt | cctgggtccc | tattaccctc | aacttgactg | tccacgtctt | catgtactac | 600 |
| tactacatgc | gctccgctgc | cggtgttcgc | atctggtgga | agcagtactt | gaccactctc | 660 |
| cagatcgtcc | agttcgttct | tgacctcgga | ttcatctact | tctgcgccta | cacctacttc | 720 |
| gccttcacct | acttcccctg | gctcccaaac | gtcggcaagt | gcgccggtac | cgagggtgct | 780 |
| gctctctttg | gctgcggact | cctctccagc | tatctcttgc | tctttatcaa | cttctaccgc | 840 |
| attacctaca | atgccaaggc | caaggcagcc | aaggagcgtg | gaagcaactt | taccccaag | 900 |
| actgtcaagt | ccggcggatc | gcccaagaag | ccctccaaga | gcaagcacat | ctaa | 954 |

<210> SEQ ID NO 2
<211> LENGTH: 957
<212> TYPE: DNA
<213> ORGANISM: Mortierella alpina

<400> SEQUENCE: 2

| | | | | | |
|---|---|---|---|---|---|
| atggagtcga | ttgcgccatt | cctcccatca | aagatgccgc | aagatctgtt | tatggacctt | 60 |
| gccaccgcta | tcggtgtccg | ggccgcgccc | tatgtcgatc | ctctcgaggc | cgcgctggtg | 120 |
| gcccaggccg | agaagtacat | ccccacgatt | gtccatcaca | cgcgtgggtt | cctggtcgcg | 180 |
| gtggagtcgc | cttttggcccg | tgagctgccg | ttgatgaacc | cgttccacgt | gctgttgatc | 240 |
| gtgctcgctt | atttggtcac | ggtctttgtg | ggcatgcaga | tcatgaagaa | ctttgagcgg | 300 |
| ttcgaggtca | agacgttttc | gctcctgcac | aacttttgtc | tggtctcgat | cagcgcctac | 360 |
| atgtgcggtg | ggatcctgta | cgaggcttat | caggccaact | atggactgtt | tgagaacgct | 420 |
| gctgatcata | ccttcaaggg | tcttcctatg | gccaagatga | tctggctctt | ctacttctcc | 480 |
| aagatcatgg | agtttgtcga | caccatgatc | atggtcctca | agaagaacaa | ccgccagatc | 540 |
| tccttcttgc | acgtttacca | ccacagctcc | atcttcacca | tctggtggtt | ggtcacctt | 600 |
| gttgcaccca | acggtgaagc | ctacttctct | gctgcgttga | actcgttcat | ccatgtgatc | 660 |
| atgtacggct | actacttctt | gtcggccttg | ggcttcaagc | aggtgtcgtt | catcaagttc | 720 |
| tacatcacgc | gctcgcagat | gacacagttc | tgcatgatgt | cggtccagtc | ttcctgggac | 780 |
| atgtacgcca | tgaaggtcct | tggccgcccc | ggatacccct | tcttcatcac | ggctctgctt | 840 |

```
tggttctaca tgtggaccat gctcggtctc ttctacaact tttacagaaa gaacgccaag      900
ttggccaagc aggccaaggc cgacgctgcc aaggagaagg caaggaagtt gcagtaa        957

<210> SEQ ID NO 3
<211> LENGTH: 914
<212> TYPE: DNA
<213> ORGANISM: Homo sapiens

<400> SEQUENCE: 3
atggaacatt tgatgcatc acttagtacc tatttcaagg cattgctagg ccctcgagat       60
actagagtaa aaggatggtt tcttctggac aattatatac ccacatttat ctgctctgtc     120
atatatttac taattgtatg ctgggaccaa aatacatga ggaataaaca gccattctct      180
tgccggggga ttttagtggt gtataacctt ggactcacac tgctgtctct gtatatgttc    240
tgtgagttag taacaggagt atgggaaggc aaatacaact tcttctgtca gggcacacgc    300
accgcaggag aatcagatat gaagattatc cgtgtcctct ggtggtacta cttctccaaa    360
ctcatagaat ttatggacac tttcttcttc atcctgcgca agaacaacca ccagatcacg    420
gtcctgcacg tctaccacca tgcctcgatg ctgaacatct ggtggtttgt gatgaactgg    480
gtcccctgcg ccactctta ttttggtgcc acacttaata gcttcatcca cgtcctcatg    540
tactcttact atggtttgtc gtcagtccct tccatgcgtc catacctctg gtggaagaag    600
tacatcactc aggggcagct gcttcagttt gtgctgacaa tcatccagac cagctgcggg    660
gtcatctggc cgtgcacatt ccctcttggt tggttgtatt ccagattgg atacattatt    720 tccctgattg ctctcttcac aaacttctac attcagacct acaacaagaa aggggcctcc    780
cgaaggaaag accacctgaa ggaccaccag aatgggtccg tggctgctgt gaatggacac    840
accaacagct tttcacccct ggaaaacaat gtgaagccaa ggaagctgcg gaaggattga    900
agtcaaagaa ttga                                                       914

<210> SEQ ID NO 4
<211> LENGTH: 867
<212> TYPE: DNA
<213> ORGANISM: Caenorhabditis elegans

<400> SEQUENCE: 4
atggctcagc atccgctcgt tcaacggctt ctcgatgtca aattcgacac gaaacgattt      60
gtggctattg ctactcatgg gccaaagaat ttccctgacg cagaaggtcg caagttcttt    120
gctgatcact tgatgttac tattcaggct tcaatcctgt acatggtcgt tgtgttcgga    180
acaaaatggt tcatgcgtaa tcgtcaacca ttccaattga ctattccact caacatctgg    240
aatttcatcc tcgccgcatt tccatcgca ggagctgtca aaatgacccc agagttcttt    300
ggaaccattg ccaacaaagg aattgtcgca tcctactgca agtgtttga tttcacgaaa    360 ggagagaatg gatactgggt gtggctcttc atggcttcca aacttttcga acttgttgac    420
accatcttct tggttctccg taaacgtcca ctcatgttcc ttcactggta tcaccatatt    480
ctcaccatga tctacgcctg gtactctcat ccattgaccc caggattcaa cagatacgga    540
atttatctta actttgtcgt ccacgccttc atgtactctt actacttcct tcgctcgatg    600
aagattcgcg tgccaggatt catcgcccaa gctatcacat ctcttcaaat cgttcaattc    660
atcatctctt gcgccgttct tgctcatctt ggttatctca tgcacttcac caatgccaac    720
tgtgatttcg agccatcagt attcaagctc gcagttttca tggacacaac atacttggct    780
```

```
cttttcgtca acttcttcct ccaatcatat gttctccgcg gaggaaaaga caagtacaag    840
gcagtgccaa agaagaagaa caactaa                                        867
```

<210> SEQ ID NO 5
<211> LENGTH: 83
<212> TYPE: PRT
<213> ORGANISM: Simmondsia chinensis

<400> SEQUENCE: 5

```
Ala Thr Leu Pro Asn Phe Lys Ser Ser Ile Asn Leu His His Val Lys
 1               5                  10                  15

Leu Gly Tyr His Tyr Leu Ile Ser Asn Ala Leu Phe Leu Val Phe Ile
            20                  25                  30

Pro Leu Leu Gly Leu Ala Ser Ala His Leu Ser Ser Phe Ser Ala His
        35                  40                  45

Asp Leu Ser Leu Leu Phe Asp Leu Leu Arg Arg Asn Leu Leu Pro Val
    50                  55                  60

Val Val Cys Ser Phe Leu Phe Val Leu Leu Ala Thr Leu His Phe Leu
65                  70                  75                  80

Thr Arg Pro
```

<210> SEQ ID NO 6
<211> LENGTH: 80
<212> TYPE: PRT
<213> ORGANISM: Saccharomyces cerevisiae

<400> SEQUENCE: 6

```
Ser Thr Leu Pro Pro Val Leu Tyr Ala Ile Thr Ala Tyr Tyr Val Ile
 1               5                  10                  15

Ile Phe Gly Gly Arg Phe Leu Leu Ser Lys Ser Lys Pro Phe Lys Leu
            20                  25                  30

Asn Gly Leu Phe Gln Leu His Asn Leu Val Leu Thr Ser Leu Ser Leu
        35                  40                  45

Thr Leu Leu Leu Leu Met Val Glu Gln Leu Val Pro Ile Ile Val Gln
    50                  55                  60

His Gly Leu Tyr Phe Ala Ile Cys Asn Ile Gly Ala Trp Thr Gln Pro
65                  70                  75                  80
```

<210> SEQ ID NO 7
<211> LENGTH: 240
<212> TYPE: DNA
<213> ORGANISM: Saccharomyces cerevisiae

<400> SEQUENCE: 7

```
tccaccctcc ccccgtcct ctacgccatc accgcctact acgtcatcat cttcggtggt    60
cgcttcctcc tctccaagtc caagcccttc aagctcaacg gtctcttcca gctccacaac   120
ctcgtcctca cctccctctc cctcaccctc tcctcctca tggtcgagca gctcgtcccc   180
atcatcgtcc agcacggtct ctacttcgcc atctgcaaca tcggtgcctg gacccagccc   240
```

<210> SEQ ID NO 8
<211> LENGTH: 33
<212> TYPE: DNA
<213> ORGANISM: Mortierella alpina

<400> SEQUENCE: 8

```
gaattcaggc atggccgccg caatcttgga caa                                 33
```

<210> SEQ ID NO 9
<211> LENGTH: 49
<212> TYPE: DNA
<213> ORGANISM: Mortierella alpina

<400> SEQUENCE: 9
gaattcaggc atctcatgga tccgccatgg ccgccgcaat cttggacaa    49

<210> SEQ ID NO 10
<211> LENGTH: 317
<212> TYPE: PRT
<213> ORGANISM: Mortierella alpina

<400> SEQUENCE: 10

```
Met Ala Ala Ala Ile Leu Asp Lys Val Asn Phe Gly Ile Asp Gln Pro
 1               5                  10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
 50                  55                  60

Val Ile Phe Gly Gly Arg Gln Ile Met Lys Ser Gln Asp Ala Phe Lys
 65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Leu Tyr Tyr Leu Asn Tyr Leu Val Lys Tyr Trp Glu
130                 135                 140

Leu Ala Asp Thr Val Phe Leu Val Leu Lys Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
    210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
        275                 280                 285

Ala Ala Lys Glu Arg Gly Ser Asn Phe Thr Pro Lys Thr Val Lys Ser
    290                 295                 300

Gly Gly Ser Pro Lys Lys Pro Ser Lys Ser Lys His Ile
305                 310                 315
```

<210> SEQ ID NO 11

<211> LENGTH: 347
<212> TYPE: PRT
<213> ORGANISM: Saccharomyces cerevisiae

<400> SEQUENCE: 11

```
Met Asn Ser Leu Val Thr Gln Tyr Ala Ala Pro Leu Phe Glu Arg Tyr
 1               5                  10                  15

Pro Gln Leu His Asp Tyr Leu Pro Thr Leu Glu Arg Pro Phe Phe Asn
            20                  25                  30

Ile Ser Leu Trp Glu His Phe Asp Asp Val Val Thr Arg Val Thr Asn
        35                  40                  45

Gly Arg Phe Val Pro Ser Glu Phe Gln Phe Ile Ala Gly Glu Leu Pro
    50                  55                  60

Leu Ser Thr Leu Pro Pro Val Leu Tyr Ala Ile Thr Ala Tyr Tyr Val
65                  70                  75                  80

Ile Ile Phe Gly Gly Arg Phe Leu Leu Ser Lys Ser Lys Pro Phe Lys
                85                  90                  95

Leu Asn Gly Leu Phe Gln Leu His Asn Leu Val Leu Thr Ser Leu Ser
            100                 105                 110

Leu Thr Leu Leu Leu Leu Met Val Glu Gln Leu Val Pro Ile Ile Val
        115                 120                 125

Gln His Gly Leu Tyr Phe Ala Ile Cys Asn Ile Gly Ala Trp Thr Gln
    130                 135                 140

Pro Leu Val Thr Leu Tyr Tyr Met Asn Tyr Ile Val Lys Phe Ile Glu
145                 150                 155                 160

Phe Ile Asp Thr Phe Phe Leu Val Leu Lys His Lys Lys Leu Thr Phe
                165                 170                 175

Leu His Thr Tyr His His Gly Ala Thr Ala Leu Leu Cys Tyr Thr Gln
            180                 185                 190

Leu Met Gly Thr Thr Ser Ile Ser Trp Val Pro Ile Ser Leu Asn Leu
        195                 200                 205

Gly Val His Val Val Met Tyr Trp Tyr Tyr Phe Leu Ala Ala Arg Gly
    210                 215                 220

Ile Arg Val Trp Trp Lys Glu Trp Val Thr Arg Phe Gln Ile Ile Gln
225                 230                 235                 240

Phe Val Leu Asp Ile Gly Phe Ile Tyr Phe Ala Val Tyr Gln Lys Ala
                245                 250                 255

Val His Leu Tyr Phe Pro Ile Leu Pro His Cys Gly Asp Cys Val Gly
            260                 265                 270

Ser Thr Thr Ala Thr Phe Ala Gly Cys Ala Ile Ile Ser Ser Tyr Leu
        275                 280                 285

Val Leu Phe Ile Ser Phe Tyr Ile Asn Val Tyr Lys Arg Lys Gly Thr
    290                 295                 300

Lys Thr Ser Arg Val Val Lys Arg Ala His Gly Gly Val Ala Ala Lys
305                 310                 315                 320

Val Asn Glu Tyr Val Asn Val Asp Leu Lys Asn Val Pro Thr Pro Ser
                325                 330                 335

Pro Ser Pro Lys Pro Gln His Arg Arg Lys Arg
            340                 345
```

<210> SEQ ID NO 12
<211> LENGTH: 345
<212> TYPE: PRT
<213> ORGANISM: Saccharomyces cerevisiae

<400> SEQUENCE: 12

```
Met Asn Thr Thr Thr Ser Thr Val Ile Ala Ala Val Ala Asp Gln Phe
  1               5                  10                  15

Gln Ser Leu Asn Ser Ser Ser Cys Phe Leu Lys Val His Val Pro
             20              25                  30

Ser Ile Glu Asn Pro Phe Gly Ile Glu Leu Trp Pro Ile Phe Ser Lys
         35                  40                  45

Val Phe Glu Tyr Phe Ser Gly Tyr Pro Ala Glu Gln Phe Glu Phe Ile
 50                      55                  60

His Asn Lys Thr Phe Leu Ala Asn Gly Tyr His Ala Val Ser Ile Ile
 65                  70                  75                  80

Ile Val Tyr Tyr Ile Ile Phe Gly Gln Ala Ile Leu Arg Ala
                 85                  90                  95

Leu Asn Ala Ser Pro Leu Lys Phe Lys Leu Leu Phe Glu Ile His Asn
             100                 105                 110

Leu Phe Leu Thr Ser Ile Ser Leu Val Leu Trp Leu Leu Met Leu Glu
         115                 120                 125

Gln Leu Val Pro Met Val Tyr His Asn Gly Leu Phe Trp Ser Ile Cys
 130                 135                 140

Ser Lys Glu Ala Phe Ala Pro Lys Leu Val Thr Leu Tyr Tyr Leu Asn
145                 150                 155                 160

Tyr Leu Thr Lys Phe Val Glu Leu Ile Asp Thr Val Phe Leu Val Leu
                 165                 170                 175

Arg Arg Lys Lys Leu Leu Phe Leu His Thr Tyr His His Gly Ala Thr
             180                 185                 190

Ala Leu Leu Cys Tyr Thr Gln Leu Ile Gly Arg Thr Ser Val Glu Trp
             195                 200                 205

Val Val Ile Leu Leu Asn Leu Gly Val His Val Ile Met Tyr Trp Tyr
 210                 215                 220

Tyr Phe Leu Ser Ser Cys Gly Ile Arg Val Trp Trp Lys Gln Trp Val
225                 230                 235                 240

Thr Arg Phe Gln Ile Ile Gln Phe Leu Ile Asp Leu Val Phe Val Tyr
                 245                 250                 255

Phe Ala Thr Tyr Thr Phe Tyr Ala His Lys Tyr Leu Asp Gly Ile Leu
                 260                 265                 270

Pro Asn Lys Gly Thr Cys Tyr Gly Thr Gln Ala Ala Ala Tyr Gly
             275                 280                 285

Tyr Leu Ile Leu Thr Ser Tyr Leu Leu Phe Ile Ser Phe Tyr Ile
 290                 295                 300

Gln Ser Tyr Lys Lys Gly Gly Lys Lys Thr Val Lys Lys Glu Ser Glu
305                 310                 315                 320

Val Ser Gly Ser Val Ala Ser Gly Ser Ser Thr Gly Val Lys Thr Ser
                 325                 330                 335

Asn Thr Lys Val Ser Ser Arg Lys Ala
                 340                 345

<210> SEQ ID NO 13
<211> LENGTH: 587
<212> TYPE: DNA
<213> ORGANISM: Mortierella alpina

<400> SEQUENCE: 13
tctcgaccca gagagaggtc gccatgtgga ctatcactta cttcgtcgtc atctttggtg    60
gtcgccagat catgaagagc caggacgcct tcaagctcaa gcccctcttc atcctccaca   120
```

-continued

```
acttcctcct gacgatcgcg tccggatcgc tgttgctcct gttcatcgag aacctggtcc    180
ccatcctcgc cagaaacgga cttttctacg ccatctgcga cgacggtgcc tggacccagc    240
gcctcgagct cctctactac ctcaactacc tggtcaagta ctgggagttg gccgacaccg    300 tcttttggt cctcaagaag aagcctcttg agttcctgca ctacttccac cactcgatga     360
ccatggttct ctgctttgtc cagcttggag gatacacttc agtgtcctgg gtccctatta    420
ccctcaactt gactgtccac gtcttcatgt actactacta catgcgctcc gctgccggtg    480
ttcgcatctg gtggaagcag tacttgacca ctctccagat cgtccagttc gttcttgacc    540
tcggattcat ctacttctgc gcctacacct acttcgcctt cacctac                  587
```

<210> SEQ ID NO 14
<211> LENGTH: 590
<212> TYPE: DNA
<213> ORGANISM: Saccharomyces cerevisiae

<400> SEQUENCE: 14

```
cattaagcac tttgcccct gtgctatacg ccatcactgc ctattacgtt attattttg     60 gtggcaggtt tttgttaagt aagtcgaaac catttaaatt aaatggcctt ttccaattgc    120
ataatttggt tttaacttca ctttcattga cgcttttatt gcttatggtt gaacaattag    180
tgccaattat tgttcagcac gggttatact tcgctatctg taatattggt gcttggactc    240
aaccgctcgt tacattatat tacatgaatt acattgtcaa gtttattgaa tttatagaca    300 ccttttctt ggtgctaaaa cataaaaaat tgacattttt gcatacttat caccatggcg     360
ctactgcctt attatgttac acccaattga tgggcaccac atctatttct tgggtcccta    420
tttcattgaa ccttggtgtt cacgtggtta tgtattggta ctatttcttg gctgccagag    480
gcatcagggt ctggtggaag gaatgggtta ccagatttca aattatccaa tttgttttgg    540
atatcggttt catatatttt gctgtctacc aaaaagcagt tcacttgtat                590
```

<210> SEQ ID NO 15
<211> LENGTH: 278
<212> TYPE: PRT
<213> ORGANISM: Caenorhabditis elegans

<400> SEQUENCE: 15

```
Arg Thr Phe Lys Met Met Asp Gln Ile Leu Gly Thr Asn Phe Thr Tyr
  1               5                  10                  15

Glu Gly Ala Lys Glu Val Ala Arg Gly Leu Glu Gly Phe Ser Ala Lys
             20                  25                  30

Leu Ala Val Gly Tyr Ile Ala Thr Ile Phe Gly Leu Lys Tyr Tyr Met
         35                  40                  45

Lys Asp Arg Lys Ala Phe Asp Leu Ser Thr Pro Leu Asn Ile Trp Asn
     50                  55                  60

Gly Ile Leu Ser Thr Phe Ser Leu Leu Gly Phe Leu Phe Thr Phe Pro
 65                  70                  75                  80

Thr Leu Leu Ser Val Ile Arg Lys Asp Gly Phe Ser His Thr Tyr Ser
                 85                  90                  95

His Val Ser Glu Leu Tyr Thr Asp Ser Thr Ser Gly Tyr Trp Ile Phe
            100                 105                 110

Leu Trp Val Ile Ser Lys Ile Pro Glu Leu Leu Asp Thr Val Phe Ile
        115                 120                 125

Val Leu Arg Lys Arg Pro Leu Ile Phe Met His Trp Tyr His His Ala
    130                 135                 140
```

```
Leu Thr Gly Tyr Tyr Ala Leu Val Cys Tyr His Glu Asp Ala Val His
145                 150                 155                 160

Met Val Trp Val Val Trp Met Asn Tyr Ile Ile His Ala Phe Met Tyr
                165                 170                 175

Gly Tyr Tyr Leu Leu Lys Ser Leu Lys Val Pro Ile Pro Pro Ser Val
            180                 185                 190

Ala Gln Ala Ile Thr Thr Ser Gln Met Val Gln Phe Ala Val Ala Ile
        195                 200                 205

Phe Ala Gln Val His Val Ser Tyr Lys His Tyr Val Glu Gly Val Glu
    210                 215                 220

Gly Leu Ala Tyr Ser Phe Arg Gly Thr Ala Ile Gly Phe Phe Met Leu
225                 230                 235                 240

Thr Thr Tyr Phe Tyr Leu Trp Ile Gln Phe Tyr Lys Glu His Tyr Leu
                245                 250                 255

Lys Asn Gly Gly Lys Lys Tyr Asn Leu Ala Lys Asp Gln Ala Lys Thr
            260                 265                 270

Gln Thr Lys Lys Ala Asn
            275

<210> SEQ ID NO 16
<211> LENGTH: 293
<212> TYPE: PRT
<213> ORGANISM: Mortierella alpina
<220> FEATURE:
<221> NAME/KEY: VARIANT
<222> LOCATION: (293)...(293)
<223> OTHER INFORMATION: Xaa = Unknown or Other at position 293

<400> SEQUENCE: 16

Ala Gln Ala Tyr Glu Leu Val Thr Gly Lys Ser Ile Asp Ser Phe Val
1               5                   10                  15

Phe Gln Glu Gly Val Thr Pro Leu Ser Thr Gln Arg Glu Val Ala Met
            20                  25                  30

Trp Thr Ile Thr Tyr Phe Val Val Phe Gly Gly Arg Gln Ile Met
            35                  40                  45

Lys Ser Gln Asp Ala Phe Lys Leu Lys Pro Leu Phe Ile Leu His Asn
50                  55                  60

Phe Leu Leu Thr Ile Ala Ser Gly Ser Leu Leu Leu Phe Ile Glu
65                  70                  75                  80

Asn Leu Val Pro Ile Leu Ala Arg Asn Gly Leu Phe Tyr Ala Ile Cys
                85                  90                  95

Asp Asp Gly Ala Trp Thr Gln Arg Leu Glu Leu Leu Tyr Tyr Leu Asn
            100                 105                 110

Tyr Leu Val Lys Tyr Trp Glu Leu Ala Asp Thr Val Phe Leu Val Leu
        115                 120                 125

Lys Lys Lys Pro Leu Glu Phe Leu His Tyr Phe His His Ser Met Thr
130                 135                 140

Met Val Leu Cys Phe Val Gln Leu Gly Gly Tyr Thr Ser Val Ser Trp
145                 150                 155                 160

Val Pro Ile Thr Leu Asn Leu Thr Val His Val Phe Met Tyr Tyr Tyr
                165                 170                 175

Tyr Met Arg Ser Ala Ala Gly Val Arg Ile Trp Trp Lys Gln Tyr Leu
            180                 185                 190

Thr Thr Leu Gln Ile Val Gln Phe Val Leu Asp Leu Gly Phe Ile Tyr
        195                 200                 205

Phe Cys Ala Tyr Thr Tyr Phe Ala Phe Thr Tyr Phe Pro Trp Ala Pro
```

-continued

```
                210                 215                 220
Asn Val Gly Lys Cys Ala Gly Thr Glu Gly Ala Ala Leu Phe Gly Cys
225                 230                 235                 240

Gly Leu Leu Ser Ser Tyr Leu Leu Phe Ile Asn Phe Tyr Arg Ile
                245                 250                 255

Thr Tyr Asn Ala Lys Ala Lys Ala Ala Lys Glu Arg Gly Ser Asn Phe
            260                 265                 270

Thr Pro Lys Thr Val Lys Ser Gly Ser Pro Lys Lys Pro Ser Lys
                275                 280                 285

Ser Lys His Ile Xaa
    290
```

<210> SEQ ID NO 17
<211> LENGTH: 238
<212> TYPE: PRT
<213> ORGANISM: Caenorhabditis elegans

<400> SEQUENCE: 17

```
Ser Leu Leu Thr Asn Gln Asp Glu Val Phe Pro His Ile Arg Ala Arg
1               5                   10                  15

Arg Phe Ile Gln Glu His Phe Gly Leu Phe Val Gln Met Ala Ile Ala
            20                  25                  30

Tyr Val Ile Leu Val Phe Ser Ile Lys Arg Phe Met Arg Asp Arg Glu
        35                  40                  45

Pro Phe Gln Leu Thr Thr Ala Leu Arg Leu Trp Asn Phe Phe Leu Ser
    50                  55                  60

Val Phe Ser Ile Tyr Gly Ser Trp Thr Met Phe Pro Phe Met Val Gln
65                  70                  75                  80

Gln Ile Arg Leu Tyr Gly Leu Tyr Gly Cys Gly Cys Glu Ala Leu Ser
                85                  90                  95

Asn Leu Pro Ser Gln Ala Glu Tyr Trp Leu Phe Leu Thr Ile Leu Ser
            100                 105                 110

Lys Ala Val Glu Phe Val Asp Thr Phe Phe Leu Val Leu Arg Lys Lys
        115                 120                 125

Pro Leu Ile Phe Leu His Trp Tyr His His Met Ala Thr Phe Val Phe
    130                 135                 140

Phe Cys Ser Asn Tyr Pro Thr Pro Ser Ser Gln Ser Arg Val Gly Val
145                 150                 155                 160

Ile Val Asn Leu Phe Val His Ala Phe Met Tyr Pro Tyr Tyr Phe Thr
                165                 170                 175

Arg Ser Met Asn Ile Lys Val Pro Ala Lys Ile Ser Met Ala Val Thr
            180                 185                 190

Val Leu Gln Leu Thr Gln Phe Met Cys Phe Ile Tyr Gly Cys Thr Leu
        195                 200                 205

Met Tyr Tyr Ser Leu Ala Thr Asn Gln Ala Arg Tyr Pro Ser Asn Thr
    210                 215                 220

Pro Ala Thr Leu Gln Cys Leu Ser Tyr Thr Leu His Leu Leu
225                 230                 235
```

<210> SEQ ID NO 18
<211> LENGTH: 289
<212> TYPE: PRT
<213> ORGANISM: Mortierella alpina
<220> FEATURE:
<221> NAME/KEY: VARIANT
<222> LOCATION: (289)...(289)
<223> OTHER INFORMATION: Xaa = Unknown or Other at position 289

<400> SEQUENCE: 18

```
Glu Leu Val Thr Gly Lys Ser Ile Asp Ser Phe Val Phe Gln Glu Gly
 1               5                  10                  15

Val Thr Pro Leu Ser Thr Gln Arg Glu Val Ala Met Trp Thr Ile Thr
            20                  25                  30

Tyr Phe Val Val Ile Phe Gly Gly Arg Gln Ile Met Lys Ser Gln Asp
        35                  40                  45

Ala Phe Lys Leu Lys Pro Leu Phe Ile Leu His Asn Phe Leu Leu Thr
    50                  55                  60

Ile Ala Ser Gly Ser Leu Leu Leu Phe Ile Glu Asn Leu Val Pro
65                  70                  75                  80

Ile Leu Ala Arg Asn Gly Leu Phe Tyr Ala Ile Cys Asp Asp Gly Ala
                85                  90                  95

Trp Thr Gln Arg Leu Glu Leu Leu Tyr Tyr Leu Asn Tyr Leu Val Lys
            100                 105                 110

Tyr Trp Glu Leu Ala Asp Thr Val Phe Leu Val Leu Lys Lys Lys Pro
        115                 120                 125

Leu Glu Phe Leu His Tyr Phe His His Ser Met Thr Met Val Leu Cys
    130                 135                 140

Phe Val Gln Leu Gly Gly Tyr Thr Ser Val Ser Trp Val Pro Ile Thr
145                 150                 155                 160

Leu Asn Leu Thr Val His Val Phe Met Tyr Tyr Tyr Met Arg Ser
                165                 170                 175

Ala Ala Gly Val Arg Ile Trp Trp Lys Gln Tyr Leu Thr Thr Leu Gln
            180                 185                 190

Ile Val Gln Phe Val Leu Asp Leu Gly Phe Ile Tyr Phe Cys Ala Tyr
        195                 200                 205

Thr Tyr Phe Ala Phe Thr Tyr Phe Pro Trp Ala Pro Asn Val Gly Lys
    210                 215                 220

Cys Ala Gly Thr Glu Gly Ala Ala Leu Phe Gly Cys Gly Leu Leu Ser
225                 230                 235                 240

Ser Tyr Leu Leu Leu Phe Ile Asn Phe Tyr Arg Ile Thr Tyr Asn Ala
                245                 250                 255

Lys Ala Lys Ala Ala Lys Glu Arg Gly Ser Asn Phe Thr Pro Lys Thr
            260                 265                 270

Val Lys Ser Gly Gly Ser Pro Lys Pro Ser Lys Ser Lys His Ile
        275                 280                 285

Xaa
```

<210> SEQ ID NO 19
<211> LENGTH: 101
<212> TYPE: PRT
<213> ORGANISM: Caenorhabditis elegans

<400> SEQUENCE: 19

```
Met Leu Tyr Ser Ile Thr Arg Arg Cys Tyr Thr Phe Phe Val Thr Ser
 1               5                  10                  15

Leu His Phe Tyr Gln Leu Tyr Val Thr Glu Cys Leu Glu Asn Val Ile
            20                  25                  30

Phe Asn Val Leu Val Asn Gly Gln Ser Ile Asn Ser Arg Trp Lys Asp
        35                  40                  45

Ala Glu Lys Thr Ile Thr Ser Phe Pro Phe His Phe Pro Gln Thr Phe
    50                  55                  60
```

```
Phe Gln Gln Pro His Ile Leu Thr Leu His Phe Leu Phe Val Phe
 65                  70                  75                  80

Val Ser Val Thr Leu Val Thr Val Phe Lys Lys Pro Lys Cys Glu Phe
                 85                  90                  95

Pro His Ser Leu Ala
            100

<210> SEQ ID NO 20
<211> LENGTH: 115
<212> TYPE: PRT
<213> ORGANISM: Mortierella alpina

<400> SEQUENCE: 20

Met Ala Ala Ala Ile Leu Asp Lys Val Asn Phe Gly Ile Asp Gln Pro
  1               5                  10                  15

Phe Gly Ile Lys Leu Asp Thr Tyr Phe Ala Gln Ala Tyr Glu Leu Val
                 20                  25                  30

Thr Gly Lys Ser Ile Asp Ser Phe Val Phe Gln Glu Gly Val Thr Pro
             35                  40                  45

Leu Ser Thr Gln Arg Glu Val Ala Met Trp Thr Ile Thr Tyr Phe Val
 50                  55                  60

Val Ile Phe Gly Gly Arg Gln Ile Met Lys Ser Gln Asp Ala Phe Lys
 65                  70                  75                  80

Leu Lys Pro Leu Phe Ile Leu His Asn Phe Leu Leu Thr Ile Ala Ser
                 85                  90                  95

Gly Ser Leu Leu Leu Leu Phe Ile Glu Asn Leu Val Pro Ile Leu Ala
            100                 105                 110

Arg Asn Gly
        115

<210> SEQ ID NO 21
<211> LENGTH: 272
<212> TYPE: PRT
<213> ORGANISM: Mus musculus
<220> FEATURE:
<221> NAME/KEY: VARIANT
<222> LOCATION: (272)...(272)
<223> OTHER INFORMATION: Xaa = Unknown or Other at position 272

<400> SEQUENCE: 21

Met Asp Thr Ser Met Asn Phe Ser Arg Gly Leu Lys Met Asp Leu Met
  1               5                  10                  15

Gln Pro Tyr Asp Phe Glu Thr Phe Gln Asp Leu Arg Pro Phe Leu Glu
                 20                  25                  30

Glu Tyr Trp Val Ser Ser Phe Leu Ile Val Val Tyr Leu Leu Leu
             35                  40                  45

Ile Val Val Gly Gln Thr Tyr Met Arg Thr Arg Lys Ser Phe Ser Leu
 50                  55                  60

Gln Arg Pro Leu Ile Leu Trp Ser Phe Phe Leu Ala Ile Phe Ser Ile
 65                  70                  75                  80

Leu Gly Thr Leu Arg Met Trp Lys Phe Met Ala Thr Val Met Phe Thr
                 85                  90                  95

Val Gly Leu Lys Gln Thr Val Cys Phe Ala Ile Tyr Thr Asp Asp Ala
            100                 105                 110

Val Val Arg Phe Trp Ser Phe Leu Phe Leu Leu Ser Lys Val Val Glu
            115                 120                 125

Leu Gly Asp Thr Ala Phe Ile Ile Leu Arg Lys Arg Pro Leu Ile Phe
130                 135                 140
```

```
Val His Trp Tyr His His Ser Thr Val Leu Leu Phe Thr Ser Phe Gly
145                 150                 155                 160

Tyr Lys Asn Lys Val Pro Ser Gly Gly Trp Phe Met Thr Met Asn Phe
                165                 170                 175

Gly Val His Ser Val Met Tyr Thr Tyr Tyr Thr Met Lys Ala Ala Lys
            180                 185                 190

Leu Lys His Pro Asn Leu Leu Pro Met Val Ile Thr Ser Leu Gln Ile
        195                 200                 205

Leu Gln Met Val Leu Gly Thr Ile Phe Gly Ile Leu Asn Tyr Ile Trp
    210                 215                 220

Arg Gln Glu Lys Gly Cys His Thr Thr Thr Glu His Phe Phe Trp Ser
225                 230                 235                 240

Phe Met Leu Tyr Gly Thr Tyr Phe Ile Leu Phe Ala His Phe Phe His
                245                 250                 255

Arg Ala Tyr Leu Arg Pro Lys Gly Lys Val Ala Ser Lys Ser Gln Xaa
                260                 265                 270

<210> SEQ ID NO 22
<211> LENGTH: 318
<212> TYPE: PRT
<213> ORGANISM: Mortierella alpina
<220> FEATURE:
<221> NAME/KEY: VARIANT
<222> LOCATION: (318)...(318)
<223> OTHER INFORMATION: Xaa = Unknown or Other at position 318

<400> SEQUENCE: 22

Met Ala Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
    50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Leu Tyr Tyr Leu Asn Tyr Leu Val Lys Tyr Trp Glu
    130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
    210                 215                 220
```

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
            245                 250                 255

Thr Glu Gly Ala Ala Leu Phe Gly Cys Gly Leu Leu Ser Ser Tyr Leu
        260                 265                 270

Leu Leu Phe Ile Asn Phe Tyr Arg Ile Thr Tyr Asn Ala Lys Ala Lys
    275                 280                 285

Ala Ala Lys Glu Arg Gly Ser Asn Phe Thr Pro Lys Thr Val Lys Ser
    290                 295                 300

Gly Gly Ser Pro Lys Lys Pro Ser Lys Ser Lys His Ile Xaa
305                 310                 315

<210> SEQ ID NO 23
<211> LENGTH: 178
<212> TYPE: PRT
<213> ORGANISM: Mortierella alpina

<400> SEQUENCE: 23

Asn Leu Val Pro Ile Leu Ala Arg Asn Gly Leu Phe Tyr Ala Ile Cys
1               5                   10                  15

Asp Asp Gly Ala Trp Thr Gln Arg Leu Glu Leu Leu Tyr Tyr Leu Asn
            20                  25                  30

Tyr Leu Val Lys Tyr Trp Glu Leu Ala Asp Thr Val Phe Leu Val Leu
        35                  40                  45

Lys Lys Lys Pro Leu Glu Phe Leu His Tyr Phe His His Ser Met Thr
    50                  55                  60

Met Val Leu Cys Phe Val Gln Leu Gly Gly Tyr Thr Ser Val Ser Trp
65                  70                  75                  80

Val Pro Ile Thr Leu Asn Leu Thr Val His Val Phe Met Tyr Tyr Tyr
                85                  90                  95

Tyr Met Arg Ser Ala Ala Gly Val Arg Ile Trp Trp Lys Gln Tyr Leu
            100                 105                 110

Thr Thr Leu Gln Ile Val Gln Phe Val Leu Asp Leu Gly Phe Ile Tyr
        115                 120                 125

Phe Cys Ala Tyr Thr Tyr Phe Ala Phe Thr Tyr Phe Pro Trp Ala Pro
    130                 135                 140

Asn Val Gly Lys Cys Ala Gly Thr Glu Gly Ala Ala Leu Phe Gly Cys
145                 150                 155                 160

Gly Leu Leu Ser Ser Tyr Leu Leu Leu Phe Ile Asn Phe Tyr Arg Ile
                165                 170                 175

Thr Tyr

<210> SEQ ID NO 24
<211> LENGTH: 147
<212> TYPE: PRT
<213> ORGANISM: Homo sapiens

<400> SEQUENCE: 24

Ser Leu Leu Val Val Lys Asp Leu Thr Tyr Leu Pro Leu Cys Leu
1               5                   10                  15

Pro Gly Asp Thr Ile Phe Ile Leu Arg Lys Gln Lys Leu Ile Phe
            20                  25                  30

Leu His Trp Tyr His His Ile Thr Val Leu Leu Tyr Ser Trp Tyr Ser
        35                  40                  45

```
Tyr Lys Asp Met Val Ala Gly Gly Trp Phe Met Thr Met Asn Tyr
 50                  55                  60

Gly Val His Ala Val Met Tyr Ser Tyr Tyr Ala Leu Arg Ala Ala Gly
 65                  70                  75                  80

Phe Arg Val Ser Arg Lys Phe Ala Met Phe Ile Thr Leu Ser Gln Ile
                 85                  90                  95

Thr Gln Met Leu Met Gly Cys Val Val Asn Tyr Leu Val Phe Cys Trp
            100                 105                 110

Met Gln His Asp Gln Cys His Ser His Phe Gln Asn Ile Phe Trp Ser
            115                 120                 125

Ser Leu Met Tyr Leu Ser Tyr Leu Val Leu Phe Cys His Phe Phe
130                 135                 140

Glu Ala Tyr
145

<210> SEQ ID NO 25
<211> LENGTH: 280
<212> TYPE: PRT
<213> ORGANISM: Mortierella alpina
<220> FEATURE:
<221> NAME/KEY: VARIANT
<222> LOCATION: (280)...(280)
<223> OTHER INFORMATION: Xaa = Unknown or Other at position 280

<400> SEQUENCE: 25

Ser Phe Val Phe Gln Glu Gly Val Thr Pro Leu Ser Thr Gln Arg Glu
 1               5                  10                  15

Val Ala Met Trp Thr Ile Thr Tyr Phe Val Val Ile Phe Gly Gly Arg
                20                  25                  30

Gln Ile Met Lys Ser Gln Asp Ala Phe Lys Leu Lys Pro Leu Phe Ile
            35                  40                  45

Leu His Asn Phe Leu Leu Thr Ile Ala Ser Gly Ser Leu Leu Leu Leu
 50                  55                  60

Phe Ile Glu Asn Leu Val Pro Ile Leu Ala Arg Asn Gly Leu Phe Tyr
 65                  70                  75                  80

Ala Ile Cys Asp Asp Gly Ala Trp Thr Gln Arg Leu Glu Leu Leu Tyr
                 85                  90                  95

Tyr Leu Asn Tyr Leu Val Lys Tyr Trp Glu Leu Ala Asp Thr Val Phe
            100                 105                 110

Leu Val Leu Lys Lys Lys Pro Leu Glu Phe Leu His Tyr Phe His His
            115                 120                 125

Ser Met Thr Met Val Leu Cys Phe Val Gln Leu Gly Gly Tyr Thr Ser
130                 135                 140

Val Ser Trp Val Pro Ile Thr Leu Asn Leu Thr Val His Val Phe Met
145                 150                 155                 160

Tyr Tyr Tyr Tyr Met Arg Ser Ala Ala Gly Val Arg Ile Trp Trp Lys
                165                 170                 175

Gln Tyr Leu Thr Thr Leu Gln Ile Val Gln Phe Val Leu Asp Leu Gly
            180                 185                 190

Phe Ile Tyr Phe Cys Ala Tyr Thr Tyr Phe Ala Phe Thr Tyr Phe Pro
            195                 200                 205

Trp Ala Pro Asn Val Gly Lys Cys Ala Gly Thr Glu Gly Ala Ala Leu
210                 215                 220

Phe Gly Cys Gly Leu Leu Ser Ser Tyr Leu Leu Phe Ile Asn Phe
225                 230                 235                 240

Tyr Arg Ile Thr Tyr Asn Ala Lys Ala Lys Ala Ala Lys Glu Arg Gly
```

```
                245                 250                 255
Ser Asn Phe Thr Pro Lys Thr Val Lys Ser Gly Gly Ser Pro Lys Lys
        260                 265                 270

Pro Ser Lys Ser Lys His Ile Xaa
        275                 280

<210> SEQ ID NO 26
<211> LENGTH: 283
<212> TYPE: PRT
<213> ORGANISM: Potential Mammalian Elongase
<220> FEATURE:
<221> NAME/KEY: VARIANT
<222> LOCATION: (282)...(282)
<223> OTHER INFORMATION: Xaa = Unknown or other at position 282

<400> SEQUENCE: 26

Pro Arg Tyr Lys Ser Gln Arg Met Val Pro Pro Gly Gln Leu His Pro
  1               5                  10                  15

Tyr Val Cys Leu Phe Cys Tyr Leu Leu Thr His Cys Met Ala Gly Thr
             20                  25                  30

Lys Ile His Glu Glu Pro Ala Ala Val Leu Leu Pro Ser Ile Leu Gln
         35                  40                  45

Leu Tyr Asn Leu Gly Leu Thr Leu Leu Ser Leu Tyr Met Phe Tyr Glu
     50                  55                  60

Leu Val Thr Gly Val Trp Glu Gly Lys Tyr Asn Phe Phe Cys Gln Gly
 65                  70                  75                  80

Thr Arg Ser Ala Gly Glu Ser Asp Met Lys Ile Ile Arg Val Leu Trp
                 85                  90                  95

Trp Tyr Tyr Phe Ser Lys Leu Ile Glu Phe Met Asp Thr Phe Phe Phe
            100                 105                 110

Ile Leu Arg Lys Asn Asn His Gln Ile Thr Val Leu His Val Tyr His
        115                 120                 125

His Ala Thr Met Leu Asn Ile Trp Trp Phe Val Met Asn Trp Val Pro
    130                 135                 140

Cys Gly His Ser Tyr Phe Gly Ala Thr Leu Asn Ser Phe Ile His Val
145                 150                 155                 160

Leu Met Tyr Ser Tyr Tyr Gly Leu Ser Ser Ile Pro Ser Met Arg Pro
                165                 170                 175

Tyr Leu Trp Trp Lys Lys Tyr Ile Thr Gln Gly Gln Leu Val Gln Phe
            180                 185                 190

Val Leu Thr Ile Ile Gln Thr Thr Cys Gly Val Phe Trp Pro Cys Ser
        195                 200                 205

Phe Pro Leu Gly Trp Leu Phe Phe Gln Ile Gly Tyr Met Ile Ser Leu
    210                 215                 220

Ile Ala Leu Phe Thr Asn Phe Tyr Ile Gln Thr Tyr Asn Lys Lys Gly
225                 230                 235                 240

Ala Ser Arg Arg Lys Glu His Leu Lys Gly His Gln Asn Gly Ser Val
                245                 250                 255

Ala Ala Val Asn Gly His Thr Asn Ser Phe Pro Ser Leu Glu Asn Ser
            260                 265                 270

Val Lys Pro Arg Lys Gln Arg Lys Asp Xaa Gln
        275                 280

<210> SEQ ID NO 27
<211> LENGTH: 446
<212> TYPE: PRT
<213> ORGANISM: Mortierella alpina
```

<400> SEQUENCE: 27

```
Met Gly Thr Asp Gln Gly Lys Thr Phe Thr Trp Glu Glu Leu Ala Ala
 1               5                  10                  15

His Asn Thr Lys Asp Asp Leu Leu Ala Ile Arg Gly Arg Val Tyr
             20                  25                  30

Asp Val Thr Lys Phe Leu Ser Arg His Pro Gly Gly Val Asp Thr Leu
             35                  40                  45

Leu Leu Gly Ala Gly Arg Asp Val Thr Pro Val Phe Glu Met Tyr His
 50                  55                  60

Ala Phe Gly Ala Ala Asp Ala Ile Met Lys Lys Tyr Tyr Val Gly Thr
 65                  70                  75                  80

Leu Val Ser Asn Glu Leu Pro Ile Phe Pro Glu Pro Thr Val Phe His
                 85                  90                  95

Lys Thr Ile Lys Thr Arg Val Glu Gly Tyr Phe Thr Asp Arg Asn Ile
                100                 105                 110

Asp Pro Lys Asn Arg Pro Glu Ile Trp Gly Arg Tyr Ala Leu Ile Phe
            115                 120                 125

Gly Ser Leu Ile Ala Ser Tyr Tyr Ala Gln Leu Phe Val Pro Phe Val
130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
                180                 185                 190

Asp Phe Phe Asn Gly Ala Ser Tyr Leu Val Trp Met Tyr Gln His Met
            195                 200                 205

Leu Gly His His Pro Tyr Thr Asn Ile Ala Gly Ala Asp Pro Asp Val
210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
275                 280                 285

Thr Val Met Phe Trp Gly Gly Lys Ala Phe Phe Val Trp Tyr Arg Leu
290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
                355                 360                 365

Asp Tyr Ala His Asp Ser His Leu Trp Thr Ser Ile Thr Gly Ser Leu
            370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
```

```
                    405                 410                 415
Val Pro Tyr Leu Val Lys Asp Thr Phe Trp Gln Ala Phe Ala Ser His
                420                 425                 430

Leu Glu His Leu Arg Val Leu Gly Leu Arg Pro Lys Glu Glu
            435                 440                 445

<210> SEQ ID NO 28
<211> LENGTH: 318
<212> TYPE: PRT
<213> ORGANISM: Mortierella alpina

<400> SEQUENCE: 28

Met Glu Ser Ile Ala Pro Phe Leu Pro Ser Lys Met Pro Gln Asp Leu
  1               5                  10                  15

Phe Met Asp Leu Ala Thr Ala Ile Gly Val Arg Ala Ala Pro Tyr Val
                 20                  25                  30

Asp Pro Leu Glu Ala Ala Leu Val Ala Gln Ala Glu Lys Tyr Ile Pro
             35                  40                  45

Thr Ile Val His His Thr Arg Gly Phe Leu Val Ala Val Glu Ser Pro
 50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 29
<211> LENGTH: 279
```

```
<212> TYPE: PRT
<213> ORGANISM: Mortierella alpina

<400> SEQUENCE: 29

Val Ala Gln Ala Glu Lys Tyr Ile Pro Thr Ile Val His His Thr Arg
 1               5                  10                  15

Gly Phe Leu Val Ala Val Glu Ser Pro Leu Ala Arg Glu Leu Pro Leu
            20                  25                  30

Met Asn Pro Phe His Val Leu Ile Val Leu Ala Tyr Leu Val Thr
        35                  40                  45

Val Phe Val Gly Met Gln Ile Met Lys Asn Phe Glu Arg Phe Glu Val
    50                  55                  60

Lys Thr Phe Ser Leu Leu His Asn Phe Cys Leu Val Ser Ile Ser Ala
65                  70                  75                  80

Tyr Met Cys Gly Gly Ile Leu Tyr Glu Ala Tyr Gln Ala Asn Tyr Gly
                85                  90                  95

Leu Phe Glu Asn Ala Ala Asp His Thr Phe Lys Gly Leu Pro Met Ala
            100                 105                 110

Lys Met Ile Trp Leu Phe Tyr Phe Ser Lys Ile Met Glu Phe Val Asp
        115                 120                 125

Thr Met Ile Met Val Leu Lys Lys Asn Asn Arg Gln Ile Ser Phe Leu
    130                 135                 140

His Val Tyr His His Ser Ser Ile Phe Thr Ile Trp Trp Leu Val Thr
145                 150                 155                 160

Phe Val Ala Pro Asn Gly Glu Ala Tyr Phe Ser Ala Ala Leu Asn Ser
                165                 170                 175

Phe Ile His Val Ile Met Tyr Gly Tyr Tyr Phe Leu Ser Ala Leu Gly
            180                 185                 190

Phe Lys Gln Val Ser Phe Ile Lys Phe Tyr Ile Thr Arg Ser Gln Met
        195                 200                 205

Thr Gln Phe Cys Met Met Ser Val Gln Ser Ser Trp Asp Met Tyr Ala
    210                 215                 220

Met Lys Val Leu Gly Arg Pro Gly Tyr Pro Phe Phe Ile Thr Ala Leu
225                 230                 235                 240

Leu Trp Phe Tyr Met Trp Thr Met Leu Gly Leu Phe Tyr Asn Phe Tyr
                245                 250                 255

Arg Lys Asn Ala Lys Leu Ala Lys Gln Ala Lys Ala Asp Ala Ala Lys
            260                 265                 270

Glu Lys Ala Arg Lys Leu Gln
        275

<210> SEQ ID NO 30
<211> LENGTH: 301
<212> TYPE: PRT
<213> ORGANISM: Mortierella alpina
<220> FEATURE:
<221> NAME/KEY: VARIANT
<222> LOCATION: (301)...(301)
<223> OTHER INFORMATION: Xaa = Unknown or Other at position 301

<400> SEQUENCE: 30

Gly Ile Lys Leu Asp Thr Tyr Phe Ala Gln Ala Tyr Glu Leu Val Thr
 1               5                  10                  15

Gly Lys Ser Ile Asp Ser Phe Val Phe Gln Glu Gly Val Thr Pro Leu
            20                  25                  30

Ser Thr Gln Arg Glu Val Ala Met Trp Thr Ile Thr Tyr Phe Val Val
        35                  40                  45
```

```
Ile Phe Gly Gly Arg Gln Ile Met Lys Ser Gln Asp Ala Phe Lys Leu
         50                  55                  60

Lys Pro Leu Phe Ile Leu His Asn Phe Leu Leu Thr Ile Ala Ser Gly
 65                  70                  75                  80

Ser Leu Leu Leu Phe Ile Glu Asn Leu Val Pro Ile Leu Ala Arg
                 85                  90                  95

Asn Gly Leu Phe Tyr Ala Ile Cys Asp Asp Gly Ala Trp Thr Gln Arg
                100                 105                 110

Leu Glu Leu Leu Tyr Tyr Leu Asn Tyr Leu Val Lys Tyr Trp Glu Leu
            115                 120                 125

Ala Asp Thr Val Phe Leu Val Leu Lys Lys Pro Leu Glu Phe Leu
        130                 135                 140

His Tyr Phe His His Ser Met Thr Met Val Leu Cys Phe Val Gln Leu
145                 150                 155                 160

Gly Gly Tyr Thr Ser Val Ser Trp Val Pro Ile Thr Leu Asn Leu Thr
                165                 170                 175

Val His Val Phe Met Tyr Tyr Tyr Met Arg Ser Ala Ala Gly Val
                180                 185                 190

Arg Ile Trp Trp Lys Gln Tyr Leu Thr Thr Leu Gln Ile Val Gln Phe
        195                 200                 205

Val Leu Asp Leu Gly Phe Ile Tyr Phe Cys Ala Tyr Thr Tyr Phe Ala
210                 215                 220

Phe Thr Tyr Phe Pro Trp Ala Pro Asn Val Gly Lys Cys Ala Gly Thr
225                 230                 235                 240

Glu Gly Ala Ala Leu Phe Gly Cys Gly Leu Leu Ser Ser Tyr Leu Leu
                245                 250                 255

Leu Phe Ile Asn Phe Tyr Arg Ile Thr Tyr Asn Ala Lys Ala Lys Ala
                260                 265                 270

Ala Lys Glu Arg Gly Ser Asn Phe Thr Pro Lys Thr Val Lys Ser Gly
        275                 280                 285

Gly Ser Pro Lys Lys Pro Ser Lys Ser Lys His Ile Xaa
    290                 295                 300

<210> SEQ ID NO 31
<211> LENGTH: 289
<212> TYPE: PRT
<213> ORGANISM: Mortierella alpina

<400> SEQUENCE: 31

Tyr Glu Leu Val Thr Gly Lys Ser Ile Asp Ser Phe Val Phe Gln Glu
 1               5                  10                  15

Gly Val Thr Pro Leu Ser Thr Gln Arg Glu Val Ala Met Trp Thr Ile
            20                  25                  30

Thr Tyr Phe Val Val Ile Phe Gly Gly Arg Gln Ile Met Lys Ser Gln
                35                  40                  45

Asp Ala Phe Lys Leu Lys Pro Leu Phe Ile Leu His Asn Phe Leu Leu
 50                  55                  60

Thr Ile Ala Ser Gly Ser Leu Leu Leu Phe Ile Glu Asn Leu Val
 65                  70                  75                  80

Pro Ile Leu Ala Arg Asn Gly Leu Phe Tyr Ala Ile Cys Asp Asp Gly
                 85                  90                  95

Ala Trp Thr Gln Arg Leu Glu Leu Leu Tyr Tyr Leu Asn Tyr Leu Val
            100                 105                 110

Lys Tyr Trp Glu Leu Ala Asp Thr Val Phe Leu Val Leu Lys Lys Lys
```

```
                115                 120                 125
Pro Leu Glu Phe Leu His Tyr Phe His His Ser Met Thr Met Val Leu
    130                 135                 140

Cys Phe Val Gln Leu Gly Gly Tyr Thr Ser Val Ser Trp Val Pro Ile
145                 150                 155                 160

Thr Leu Asn Leu Thr Val His Val Phe Met Tyr Tyr Tyr Met Arg
                165                 170                 175

Ser Ala Ala Gly Val Arg Ile Trp Trp Lys Gln Tyr Leu Thr Thr Leu
                180                 185                 190

Gln Ile Val Gln Phe Val Leu Asp Leu Gly Phe Ile Tyr Phe Cys Ala
                195                 200                 205

Tyr Thr Tyr Phe Ala Phe Thr Tyr Phe Pro Trp Ala Pro Asn Val Gly
    210                 215                 220

Lys Cys Ala Gly Thr Glu Gly Ala Ala Leu Phe Gly Cys Gly Leu Leu
225                 230                 235                 240

Ser Ser Tyr Leu Leu Leu Phe Ile Asn Phe Tyr Arg Ile Thr Tyr Asn
                245                 250                 255

Ala Lys Ala Lys Ala Ala Lys Glu Arg Gly Ser Asn Phe Thr Pro Lys
                260                 265                 270

Thr Val Lys Ser Gly Gly Ser Pro Lys Lys Pro Ser Lys Ser Lys His
                275                 280                 285

Ile

<210> SEQ ID NO 32
<211> LENGTH: 292
<212> TYPE: PRT
<213> ORGANISM: Homo sapiens
<220> FEATURE:
<221> NAME/KEY: VARIANT
<222> LOCATION: (292)...(292)
<223> OTHER INFORMATION: Xaa = Unknown or Other at position 292

<400> SEQUENCE: 32

Ser Thr Tyr Phe Lys Ala Leu Leu Gly Pro Arg Asp Thr Arg Val Lys
1               5                   10                  15

Gly Trp Phe Leu Leu Asp Asn Tyr Ile Pro Thr Phe Ile Cys Ser Val
                20                  25                  30

Ile Tyr Leu Leu Ile Val Trp Leu Gly Pro Lys Tyr Met Arg Asn Lys
            35                  40                  45

Gln Pro Phe Ser Cys Arg Gly Ile Leu Val Val Tyr Asn Leu Gly Leu
    50                  55                  60

Thr Leu Leu Ser Leu Tyr Met Phe Cys Glu Leu Val Thr Gly Val Trp
65                  70                  75                  80

Glu Gly Lys Tyr Asn Phe Phe Cys Gln Gly Thr Arg Thr Ala Gly Glu
                85                  90                  95

Ser Asp Met Lys Ile Ile Arg Val Leu Trp Trp Tyr Tyr Phe Ser Lys
                100                 105                 110

Leu Ile Glu Phe Met Asp Thr Phe Phe Phe Ile Leu Arg Lys Asn Asn
                115                 120                 125

His Gln Ile Thr Val Leu His Val Tyr His His Ala Ser Met Leu Asn
                130                 135                 140

Ile Trp Trp Phe Val Met Asn Trp Val Pro Cys Gly His Ser Tyr Phe
145                 150                 155                 160

Gly Ala Thr Leu Asn Ser Phe Ile His Val Leu Met Tyr Ser Tyr Tyr
                165                 170                 175
```

```
Gly Leu Ser Ser Val Pro Ser Met Arg Pro Tyr Leu Trp Trp Lys Lys
            180                 185                 190

Tyr Ile Thr Gln Gly Gln Leu Gln Phe Val Leu Thr Ile Ile Gln
        195                 200                 205

Thr Ser Cys Gly Val Ile Trp Pro Cys Thr Phe Pro Leu Gly Trp Leu
    210                 215                 220

Tyr Phe Gln Ile Gly Tyr Met Ile Ser Leu Ile Ala Leu Phe Thr Asn
225                 230                 235                 240

Phe Tyr Ile Gln Thr Tyr Asn Lys Lys Gly Ala Ser Arg Arg Lys Asp
                245                 250                 255

His Leu Lys Asp His Gln Asn Gly Ser Met Ala Ala Val Asn Gly His
            260                 265                 270

Thr Asn Ser Phe Ser Pro Leu Glu Asn Asn Val Lys Pro Arg Lys Leu
        275                 280                 285

Arg Lys Asp Xaa
    290

<210> SEQ ID NO 33
<211> LENGTH: 291
<212> TYPE: PRT
<213> ORGANISM: Mortierella alpina

<400> SEQUENCE: 33

Gln Ala Tyr Glu Leu Val Thr Gly Lys Ser Ile Asp Ser Phe Val Phe
1               5                   10                  15

Gln Glu Gly Val Thr Pro Leu Ser Thr Gln Arg Glu Val Ala Met Trp
            20                  25                  30

Thr Ile Thr Tyr Phe Val Val Ile Phe Gly Gly Arg Gln Ile Met Lys
        35                  40                  45

Ser Gln Asp Ala Phe Lys Leu Lys Pro Leu Phe Ile Leu His Asn Phe
    50                  55                  60

Leu Leu Thr Ile Ala Ser Gly Ser Leu Leu Leu Phe Ile Glu Asn
65                  70                  75                  80

Leu Val Pro Ile Leu Ala Arg Asn Gly Leu Phe Tyr Ala Ile Cys Asp
                85                  90                  95

Asp Gly Ala Trp Thr Gln Arg Leu Glu Leu Leu Tyr Tyr Leu Asn Tyr
            100                 105                 110

Leu Val Lys Tyr Trp Glu Leu Ala Asp Thr Val Phe Leu Val Leu Lys
        115                 120                 125

Lys Lys Pro Leu Glu Phe Leu His Tyr Phe His His Ser Met Thr Met
    130                 135                 140

Val Leu Cys Phe Val Gln Leu Gly Gly Tyr Thr Ser Val Ser Trp Val
145                 150                 155                 160

Pro Ile Thr Leu Asn Leu Thr Val His Val Phe Met Tyr Tyr Tyr Tyr
                165                 170                 175

Met Arg Ser Ala Ala Gly Val Arg Ile Trp Trp Lys Gln Tyr Leu Thr
            180                 185                 190

Thr Leu Gln Ile Val Gln Phe Val Leu Asp Leu Gly Phe Ile Tyr Phe
        195                 200                 205

Cys Ala Tyr Thr Tyr Phe Ala Phe Thr Tyr Pro Trp Ala Pro Asn
    210                 215                 220

Val Gly Lys Cys Ala Gly Thr Glu Gly Ala Ala Leu Phe Gly Cys Gly
225                 230                 235                 240

Leu Leu Ser Ser Tyr Leu Leu Phe Ile Asn Phe Tyr Arg Ile Thr
                245                 250                 255
```

-continued

```
Tyr Asn Ala Lys Ala Lys Ala Lys Glu Arg Gly Ser Asn Phe Thr
            260                 265                 270

Pro Lys Thr Val Lys Ser Gly Gly Ser Pro Lys Lys Pro Ser Lys Ser
            275                 280                 285

Lys His Ile
        290

<210> SEQ ID NO 34
<211> LENGTH: 276
<212> TYPE: PRT
<213> ORGANISM: Homo sapiens
<220> FEATURE:
<221> NAME/KEY: VARIANT
<222> LOCATION: (276)...(276)
<223> OTHER INFORMATION: Xaa = Unknown or Other at position 276

<400> SEQUENCE: 34

Val Asn Leu Tyr Gln Glu Val Met Lys His Ala Asp Pro Arg Ile Gln
  1               5                  10                  15

Gly Tyr Pro Leu Met Gly Ser Pro Leu Leu Met Thr Ser Ile Leu Leu
             20                  25                  30

Thr Tyr Val Tyr Phe Val Leu Ser Leu Gly Pro Arg Ile Met Ala Asn
         35                  40                  45

Arg Lys Pro Phe Gln Leu Arg Gly Phe Met Ile Val Tyr Asn Phe Ser
     50                  55                  60

Leu Val Ala Leu Ser Leu Tyr Ile Val Tyr Glu Phe Leu Met Ser Gly
 65                  70                  75                  80

Trp Leu Ser Thr Tyr Thr Trp Arg Cys Asp Pro Val Asp Tyr Ser Asn
                 85                  90                  95

Ser Pro Glu Ala Leu Arg Met Val Arg Val Ala Trp Leu Phe Leu Phe
            100                 105                 110

Ser Lys Phe Ile Glu Leu Met Asp Thr Val Ile Phe Ile Leu Arg Lys
        115                 120                 125

Lys Asp Gly Gln Val Thr Phe Leu His Val Phe His His Ser Val Leu
130                 135                 140

Pro Trp Ser Trp Trp Trp Gly Val Lys Ile Ala Pro Gly Gly Met Gly
145                 150                 155                 160

Ser Phe His Ala Met Ile Asn Ser Ser Val His Val Ile Met Tyr Leu
                165                 170                 175

Tyr Tyr Gly Leu Ser Ala Phe Gly Pro Val Ala Gln Pro Tyr Leu Trp
            180                 185                 190

Trp Lys Lys His Met Thr Ala Ile Gln Leu Ile Gln Phe Val Leu Val
        195                 200                 205

Ser Leu His Ile Ser Gln Tyr Tyr Phe Met Ser Ser Cys Asn Tyr Gln
    210                 215                 220

Tyr Pro Val Ile Ile His Leu Ile Trp Met Tyr Gly Thr Ile Phe Phe
225                 230                 235                 240

Met Leu Phe Ser Asn Phe Trp Tyr His Ser Tyr Thr Lys Gly Lys Arg
                245                 250                 255

Leu Pro Arg Ala Leu Gln Gln Asn Gly Ala Pro Gly Ile Ala Lys Val
            260                 265                 270

Lys Ala Asn Xaa
        275

<210> SEQ ID NO 35
<211> LENGTH: 219
```

```
<212> TYPE: PRT
<213> ORGANISM: Mortierella alpina

<400> SEQUENCE: 35

Leu Leu Leu Leu Phe Ile Glu Asn Leu Pro Ile Leu Ala Arg Asn
 1               5                  10                  15

Gly Leu Phe Tyr Ala Ile Cys Asp Asp Gly Ala Trp Thr Gln Arg Leu
            20                  25                  30

Glu Leu Leu Tyr Tyr Leu Asn Tyr Leu Val Lys Tyr Trp Glu Leu Ala
         35                  40                  45

Asp Thr Val Phe Leu Val Leu Lys Lys Pro Leu Glu Phe Leu His
 50                  55                  60

Tyr Phe His His Ser Met Thr Met Val Leu Cys Phe Val Gln Leu Gly
 65                  70                  75                  80

Gly Tyr Thr Ser Val Ser Trp Val Pro Ile Thr Leu Asn Leu Thr Val
                85                  90                  95

His Val Phe Met Tyr Tyr Tyr Met Arg Ser Ala Ala Gly Val Arg
               100                 105                 110

Ile Trp Trp Lys Gln Tyr Leu Thr Thr Leu Gln Ile Val Gln Phe Val
            115                 120                 125

Leu Asp Leu Gly Phe Ile Tyr Phe Cys Ala Tyr Thr Tyr Phe Ala Phe
130                 135                 140

Thr Tyr Phe Pro Trp Ala Pro Asn Val Gly Lys Cys Ala Gly Thr Glu
145                 150                 155                 160

Gly Ala Ala Leu Phe Gly Cys Gly Leu Leu Ser Ser Tyr Leu Leu Leu
                165                 170                 175

Phe Ile Asn Phe Tyr Arg Ile Thr Tyr Asn Ala Lys Ala Lys Ala Ala
                180                 185                 190

Lys Glu Arg Gly Ser Asn Phe Thr Pro Lys Thr Val Lys Ser Gly Gly
            195                 200                 205

Ser Pro Lys Lys Pro Ser Lys Ser Lys His Ile
            210                 215

<210> SEQ ID NO 36
<211> LENGTH: 204
<212> TYPE: PRT
<213> ORGANISM: Mus musculus

<400> SEQUENCE: 36

Ile Val Tyr Glu Phe Leu Met Ser Gly Trp Leu Ser Thr Tyr Thr Trp
 1               5                  10                  15

Arg Cys Asp Pro Ile Asp Phe Ser Asn Ser Pro Glu Ala Leu Arg Met
            20                  25                  30

Val Arg Val Ala Trp Leu Phe Met Leu Ser Lys Val Ile Glu Leu Met
         35                  40                  45

Asp Thr Val Ile Phe Ile Leu Arg Lys Lys Asp Gly Gln Val Thr Phe
 50                  55                  60

Leu His Val Phe His His Ser Val Leu Pro Trp Ser Trp Trp Trp Gly
 65                  70                  75                  80

Ile Lys Ile Ala Pro Gly Gly Met Gly Ser Phe His Ala Met Ile Asn
                85                  90                  95

Ser Ser Val His Val Val Met Tyr Leu Tyr Tyr Gly Leu Ser Ala Leu
               100                 105                 110

Gly Pro Val Ala Gln Pro Tyr Leu Trp Trp Lys Lys His Met Thr Ala
            115                 120                 125
```

```
Ile Gln Leu Ile Gln Phe Val Leu Val Ser Leu His Ile Ser Gln Tyr
    130                 135                 140

Tyr Phe Met Pro Ser Cys Asn Tyr Gln Tyr Pro Val Ile Ile His Leu
145                 150                 155                 160

Ile Trp Met Tyr Gly Thr Ile Phe Phe Ile Leu Phe Ser Asn Phe Trp
                165                 170                 175

Tyr His Ser Tyr Thr Lys Gly Lys Arg Leu Pro Arg Ala Val Gln Gln
            180                 185                 190

Asn Gly Ala Pro Ala Thr Thr Lys Val Lys Ala Asn
            195                 200
```

<210> SEQ ID NO 37
<211> LENGTH: 174
<212> TYPE: PRT
<213> ORGANISM: Mortierella alpina

<400> SEQUENCE: 37

```
Tyr Glu Leu Val Thr Gly Lys Ser Ile Asp Ser Phe Val Phe Gln Glu
1               5                   10                  15

Gly Val Thr Pro Leu Ser Thr Gln Arg Glu Val Ala Met Trp Thr Ile
                20                  25                  30

Thr Tyr Phe Val Val Ile Phe Gly Gly Arg Gln Ile Met Lys Ser Gln
            35                  40                  45

Asp Ala Phe Lys Leu Lys Pro Leu Phe Ile Leu His Asn Phe Leu Leu
    50                  55                  60

Thr Ile Ala Ser Gly Ser Leu Leu Leu Phe Ile Glu Asn Leu Val
65                  70                  75                  80

Pro Ile Leu Ala Arg Asn Gly Leu Phe Tyr Ala Ile Cys Asp Asp Gly
                85                  90                  95

Ala Trp Thr Gln Arg Leu Glu Leu Leu Tyr Tyr Leu Asn Tyr Leu Val
                100                 105                 110

Lys Tyr Trp Glu Leu Ala Asp Thr Val Phe Leu Val Leu Lys Lys Lys
            115                 120                 125

Pro Leu Glu Phe Leu His Tyr Phe His His Ser Met Thr Met Val Leu
    130                 135                 140

Cys Phe Val Gln Leu Gly Gly Tyr Thr Ser Val Ser Trp Val Pro Ile
145                 150                 155                 160

Thr Leu Asn Leu Thr Val His Val Phe Met Tyr Tyr Tyr Tyr
                165                 170
```

<210> SEQ ID NO 38
<211> LENGTH: 145
<212> TYPE: PRT
<213> ORGANISM: Mus muculus

<400> SEQUENCE: 38

```
Asn Ala Phe Leu Asp Asn Met Phe Gly Pro Arg Asp Ser Arg Val Arg
1               5                   10                  15

Gly Trp Phe Leu Leu Asp Ser Tyr Leu Pro Thr Phe Ile Leu Thr Ile
                20                  25                  30

Thr Tyr Leu Leu Ser Ile Trp Leu Gly Asn Lys Tyr Met Lys Asn Arg
            35                  40                  45

Pro Ala Leu Ser Leu Arg Gly Ile Leu Thr Leu Tyr Asn Leu Ala Ile
    50                  55                  60

Thr Leu Leu Ser Ala Tyr Met Leu Val Glu Leu Ile Leu Ser Ser Trp
65                  70                  75                  80
```

```
Glu Gly Gly Tyr Asn Leu Gln Cys Gln Asn Leu Asp Ser Ala Gly Glu
                85                  90                  95

Gly Asp Val Arg Val Ala Lys Val Leu Val Trp Tyr Phe Ser Lys
            100                 105                 110

Leu Val Glu Phe Leu Asp Thr Ile Phe Phe Val Leu Arg Lys Lys Ala
        115                 120                 125

Asn Gln Ile Thr Phe Leu His Val Tyr His Ala Ser Met Phe Asn
    130                 135                 140

Ile
145

<210> SEQ ID NO 39
<211> LENGTH: 238
<212> TYPE: PRT
<213> ORGANISM: Mortierella alpina

<400> SEQUENCE: 39

Leu Ile Val Leu Ala Tyr Leu Val Thr Val Phe Val Gly Met Gln Ile
1               5                   10                  15

Met Lys Asn Phe Glu Arg Phe Glu Val Lys Thr Phe Ser Leu Leu His
            20                  25                  30

Asn Phe Cys Leu Val Ser Ile Ser Ala Tyr Met Cys Gly Gly Ile Leu
        35                  40                  45

Tyr Glu Ala Tyr Gln Ala Asn Tyr Gly Leu Phe Glu Asn Ala Ala Asp
    50                  55                  60

His Thr Phe Lys Gly Leu Pro Met Ala Lys Met Ile Trp Leu Phe Tyr
65                  70                  75                  80

Phe Ser Lys Ile Met Glu Phe Val Asp Thr Met Ile Met Val Leu Lys
                85                  90                  95

Lys Asn Asn Arg Gln Ile Ser Phe Leu His Val Tyr His His Ser Ser
            100                 105                 110

Ile Phe Thr Ile Trp Trp Leu Val Thr Phe Val Ala Pro Asn Gly Glu
        115                 120                 125

Ala Tyr Phe Ser Ala Ala Leu Asn Ser Phe Ile His Val Ile Met Tyr
    130                 135                 140

Gly Tyr Tyr Phe Leu Ser Ala Leu Gly Phe Lys Gln Val Ser Phe Ile
145                 150                 155                 160

Lys Phe Tyr Ile Thr Arg Ser Gln Met Thr Gln Phe Cys Met Met Ser
                165                 170                 175

Val Gln Ser Ser Trp Asp Met Tyr Ala Met Lys Val Leu Gly Arg Pro
            180                 185                 190

Gly Tyr Pro Phe Phe Ile Thr Ala Leu Leu Trp Phe Tyr Met Trp Thr
        195                 200                 205

Met Leu Gly Leu Phe Tyr Asn Phe Tyr Arg Lys Asn Ala Lys Leu Ala
    210                 215                 220

Lys Gln Ala Lys Ala Asp Ala Ala Lys Glu Lys Ala Arg Lys
225                 230                 235

<210> SEQ ID NO 40
<211> LENGTH: 144
<212> TYPE: PRT
<213> ORGANISM: Homo sapiens

<400> SEQUENCE: 40

Leu Tyr Asn Leu Gly Ile Thr Leu Leu Ser Ala Tyr Met Leu Ala Glu
1               5                   10                  15
```

Leu Ile Leu Ser Thr Trp Glu Gly Gly Tyr Asn Leu Gln Cys Gln Asp
            20                  25                  30

Leu Thr Ser Ala Gly Glu Ala Asp Ile Arg Val Ala Lys Val Leu Trp
        35                  40                  45

Trp Tyr Tyr Phe Ser Lys Ser Val Glu Phe Leu Asp Thr Ile Phe Phe
    50                  55                  60

Val Leu Arg Lys Lys Thr Ser Gln Ile Thr Phe Leu His Val Tyr His
65                  70                  75                  80

His Ala Ser Met Phe Asn Ile Trp Trp Cys Val Leu Asn Trp Ile Pro
                85                  90                  95

Cys Gly Gln Ser Phe Phe Gly Pro Thr Leu Asn Ser Phe Ile His Ile
            100                 105                 110

Leu Met Tyr Ser Tyr Tyr Gly Leu Ser Val Phe Pro Ser Met His Lys
        115                 120                 125

Tyr Leu Trp Trp Lys Lys Tyr Leu Thr Gln Ala Gln Leu Val Gln Phe
    130                 135                 140

<210> SEQ ID NO 41
<211> LENGTH: 278
<212> TYPE: PRT
<213> ORGANISM: Mortierella alpina

<400> SEQUENCE: 41

Ala Gln Ala Glu Lys Tyr Ile Pro Thr Ile Val His His Thr Arg Gly
1               5                   10                  15

Phe Leu Val Ala Val Glu Ser Pro Leu Ala Arg Glu Leu Pro Leu Met
            20                  25                  30

Asn Pro Phe His Val Leu Leu Ile Val Leu Ala Tyr Leu Val Thr Val
        35                  40                  45

Phe Val Gly Met Gln Ile Met Lys Asn Phe Glu Arg Phe Glu Val Lys
    50                  55                  60

Thr Phe Ser Leu Leu His Asn Phe Cys Leu Val Ser Ile Ser Ala Tyr
65                  70                  75                  80

Met Cys Gly Gly Ile Leu Tyr Glu Ala Tyr Gln Ala Asn Tyr Gly Leu
                85                  90                  95

Phe Glu Asn Ala Ala Asp His Thr Phe Lys Gly Leu Pro Met Ala Lys
            100                 105                 110

Met Ile Trp Leu Phe Tyr Phe Ser Lys Ile Met Glu Phe Val Asp Thr
        115                 120                 125

Met Ile Met Val Leu Lys Lys Asn Asn Arg Gln Ile Ser Phe Leu His
    130                 135                 140

Val Tyr His His Ser Ser Ile Phe Thr Ile Trp Trp Leu Val Thr Phe
145                 150                 155                 160

Val Ala Pro Asn Gly Glu Ala Tyr Phe Ser Ala Ala Leu Asn Ser Phe
                165                 170                 175

Ile His Val Ile Met Tyr Gly Tyr Tyr Phe Leu Ser Ala Leu Gly Phe
            180                 185                 190

Lys Gln Val Ser Phe Ile Lys Phe Tyr Ile Thr Arg Ser Gln Met Thr
        195                 200                 205

Gln Phe Cys Met Met Ser Val Gln Ser Ser Trp Asp Met Tyr Ala Met
    210                 215                 220

Lys Val Leu Gly Arg Pro Gly Tyr Pro Phe Ile Thr Ala Leu Leu
225                 230                 235                 240

Trp Phe Tyr Met Trp Thr Met Leu Gly Leu Phe Tyr Asn Phe Tyr Arg
                245                 250                 255

-continued

Lys Asn Ala Lys Leu Ala Lys Gln Ala Lys Ala Asp Ala Ala Lys Glu
                260                 265                 270

Lys Ala Arg Lys Leu Gln
            275

<210> SEQ ID NO 42
<211> LENGTH: 293
<212> TYPE: PRT
<213> ORGANISM: Homo sapiens

<400> SEQUENCE: 42

Met Glu His Phe Asp Ala Ser Leu Ser Thr Tyr Phe Lys Ala Leu Leu
 1               5                  10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
    50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
    210                 215                 220

Cys Thr Phe Pro Leu Gly Trp Leu Tyr Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly
            260                 265                 270

Ser Met Ala Ala Val Asn Gly His Thr Asn Ser Phe Ser Pro Leu Glu
        275                 280                 285

Asn Asn Val Lys Pro
    290

<210> SEQ ID NO 43
<211> LENGTH: 182
<212> TYPE: PRT
<213> ORGANISM: Mortierella alpina

<400> SEQUENCE: 43

-continued

```
Phe Glu Asn Ala Ala Asp His Thr Phe Lys Gly Leu Pro Met Ala Lys
  1               5                  10                 15

Met Ile Trp Leu Phe Tyr Phe Ser Lys Ile Met Glu Phe Val Asp Thr
             20                  25                  30

Met Ile Met Val Leu Lys Lys Asn Asn Arg Gln Ile Ser Phe Leu His
         35                  40                  45

Val Tyr His His Ser Ser Ile Phe Thr Ile Trp Trp Leu Val Thr Phe
     50                  55                  60

Val Ala Pro Asn Gly Glu Ala Tyr Phe Ser Ala Ala Leu Asn Ser Phe
 65                  70                  75                  80

Ile His Val Ile Met Tyr Gly Tyr Tyr Phe Leu Ser Ala Leu Gly Phe
                 85                  90                  95

Lys Gln Val Ser Phe Ile Lys Phe Tyr Ile Thr Arg Ser Gln Met Thr
                100                 105                 110

Gln Phe Cys Met Met Ser Val Gln Ser Ser Trp Asp Met Tyr Ala Met
            115                 120                 125

Lys Val Leu Gly Arg Pro Gly Tyr Pro Phe Phe Ile Thr Ala Leu Leu
130                 135                 140

Trp Phe Tyr Met Trp Thr Met Leu Gly Leu Phe Tyr Asn Phe Tyr Arg
145                 150                 155                 160

Lys Asn Ala Lys Leu Ala Lys Gln Ala Lys Ala Asp Ala Ala Lys Glu
                165                 170                 175

Lys Ala Arg Lys Leu Gln
                180
```

<210> SEQ ID NO 44
<211> LENGTH: 141
<212> TYPE: PRT
<213> ORGANISM: Homo sapiens
<220> FEATURE:
<221> NAME/KEY: VARIANT
<222> LOCATION: (141)...(141)
<223> OTHER INFORMATION: Xaa = Unknown or Other at position 141

<400> SEQUENCE: 44

```
Asp Thr Ile Phe Ile Ile Leu Arg Lys Gln Lys Leu Ile Phe Leu His
  1               5                  10                 15

Trp Tyr His His Ile Thr Val Leu Leu Tyr Ser Trp Tyr Ser Tyr Lys
             20                  25                  30

Asp Met Val Ala Gly Gly Trp Phe Met Thr Met Asn Tyr Gly Val
         35                  40                  45

His Ala Val Met Tyr Ser Tyr Tyr Ala Leu Arg Ala Ala Gly Phe Arg
     50                  55                  60

Val Ser Arg Lys Phe Ala Met Phe Ile Thr Leu Ser Gln Ile Thr Gln
 65                  70                  75                  80

Met Leu Met Gly Cys Val Val Asn Tyr Leu Val Phe Cys Trp Met Gln
                 85                  90                  95

His Asp Gln Cys His Ser His Phe Gln Asn Ile Phe Trp Ser Ser Leu
                100                 105                 110

Met Tyr Leu Ser Tyr Leu Val Leu Phe Cys His Phe Phe Glu Ala
            115                 120                 125

Tyr Ile Gly Lys Met Arg Lys Thr Thr Lys Ala Glu Xaa
130                 135                 140
```

<210> SEQ ID NO 45
<211> LENGTH: 241

```
<212> TYPE: PRT
<213> ORGANISM: Mortierella alpina

<400> SEQUENCE: 45

Leu Leu Ile Val Leu Ala Tyr Leu Val Thr Val Phe Val Gly Met Gln
1               5                   10                  15

Ile Met Lys Asn Phe Glu Arg Phe Glu Val Lys Thr Phe Ser Leu Leu
            20                  25                  30

His Asn Phe Cys Leu Val Ser Ile Ser Ala Tyr Met Cys Gly Gly Ile
        35                  40                  45

Leu Tyr Glu Ala Tyr Gln Ala Asn Tyr Gly Leu Phe Glu Asn Ala Ala
    50                  55                  60

Asp His Thr Phe Lys Gly Leu Pro Met Ala Lys Met Ile Trp Leu Phe
65                  70                  75                  80

Tyr Phe Ser Lys Ile Met Glu Phe Val Asp Thr Met Ile Met Val Leu
                85                  90                  95

Lys Lys Asn Asn Arg Gln Ile Ser Phe Leu His Val Tyr His His Ser
            100                 105                 110

Ser Ile Phe Thr Ile Trp Trp Leu Val Thr Phe Val Ala Pro Asn Gly
        115                 120                 125

Glu Ala Tyr Phe Ser Ala Ala Leu Asn Ser Phe Ile His Val Ile Met
    130                 135                 140

Tyr Gly Tyr Tyr Phe Leu Ser Ala Leu Gly Phe Lys Gln Val Ser Phe
145                 150                 155                 160

Ile Lys Phe Tyr Ile Thr Arg Ser Gln Met Thr Gln Phe Cys Met Met
                165                 170                 175

Ser Val Gln Ser Ser Trp Asp Met Tyr Ala Met Lys Val Leu Gly Arg
            180                 185                 190

Pro Gly Tyr Pro Phe Phe Ile Thr Ala Leu Leu Trp Phe Tyr Met Trp
        195                 200                 205

Thr Met Leu Gly Leu Phe Tyr Asn Phe Tyr Arg Lys Asn Ala Lys Leu
    210                 215                 220

Ala Lys Gln Ala Lys Ala Asp Ala Ala Lys Glu Lys Ala Arg Lys Leu
225                 230                 235                 240

Gln

<210> SEQ ID NO 46
<211> LENGTH: 217
<212> TYPE: PRT
<213> ORGANISM: Mus muculus

<400> SEQUENCE: 46

Ile Val Tyr Asn Phe Ser Leu Val Ile Leu Ser Leu Tyr Ile Val Tyr
1               5                   10                  15

Glu Phe Leu Met Ser Gly Trp Leu Ser Thr Tyr Thr Trp Arg Cys Asp
            20                  25                  30

Pro Ile Asp Phe Ser Asn Ser Pro Glu Ala Leu Arg Met Val Arg Val
        35                  40                  45

Ala Trp Leu Phe Met Leu Ser Lys Val Ile Glu Leu Met Asp Thr Val
    50                  55                  60

Ile Phe Ile Leu Arg Lys Lys Asp Gly Gln Val Thr Phe Leu His Val
65                  70                  75                  80

Phe His His Ser Val Leu Pro Trp Ser Trp Trp Gly Ile Lys Ile
                85                  90                  95

Ala Pro Gly Gly Met Gly Ser Phe His Ala Met Ile Asn Ser Ser Val
```

```
                    100                 105                 110
His Val Val Met Tyr Leu Tyr Gly Leu Ser Ala Leu Gly Pro Val
            115                 120                 125

Ala Gln Pro Tyr Leu Trp Trp Lys Lys His Met Thr Ala Ile Gln Leu
    130                 135                 140

Ile Gln Phe Val Leu Val Ser Leu His Ile Ser Gln Tyr Tyr Phe Met
145                 150                 155                 160

Pro Ser Cys Asn Tyr Gln Tyr Pro Val Ile Ile His Leu Ile Trp Met
                165                 170                 175

Tyr Gly Thr Ile Phe Phe Ile Leu Phe Ser Asn Phe Trp Tyr His Ser
            180                 185                 190

Tyr Thr Lys Gly Lys Arg Leu Pro Arg Ala Val Gln Gln Asn Gly Ala
        195                 200                 205

Pro Ala Thr Thr Lys Val Lys Ala Asn
    210                 215

<210> SEQ ID NO 47
<211> LENGTH: 178
<212> TYPE: PRT
<213> ORGANISM: Mortierella alpina

<400> SEQUENCE: 47

Pro Thr Ile Val His His Thr Arg Gly Phe Leu Val Ala Val Glu Ser
1               5                   10                  15

Pro Leu Ala Arg Glu Leu Pro Leu Met Asn Pro Phe His Val Leu Leu
            20                  25                  30

Ile Val Leu Ala Tyr Leu Val Thr Val Phe Val Gly Met Gln Ile Met
        35                  40                  45

Lys Asn Phe Glu Arg Phe Glu Val Lys Thr Phe Ser Leu Leu His Asn
    50                  55                  60

Phe Cys Leu Val Ser Ile Ser Ala Tyr Met Cys Gly Gly Ile Leu Tyr
65                  70                  75                  80

Glu Ala Tyr Gln Ala Asn Tyr Gly Leu Phe Glu Asn Ala Ala Asp His
                85                  90                  95

Thr Phe Lys Gly Leu Pro Met Ala Lys Met Ile Trp Leu Phe Tyr Phe
            100                 105                 110

Ser Lys Ile Met Glu Phe Val Asp Thr Met Ile Met Val Leu Lys Lys
        115                 120                 125

Asn Asn Arg Gln Ile Ser Phe Leu His Val Tyr His His Ser Ser Ile
    130                 135                 140

Phe Thr Ile Trp Trp Leu Val Thr Phe Val Ala Pro Asn Gly Glu Ala
145                 150                 155                 160

Tyr Phe Ser Ala Ala Leu Asn Ser Phe Ile His Val Ile Met Tyr Gly
                165                 170                 175

Tyr Tyr

<210> SEQ ID NO 48
<211> LENGTH: 148
<212> TYPE: PRT
<213> ORGANISM: Mus muculus

<400> SEQUENCE: 48

Asn Glu Val Asn Ala Phe Leu Asp Asn Met Phe Gly Pro Arg Asp Ser
1               5                   10                  15

Arg Val Arg Gly Trp Phe Leu Leu Asp Ser Tyr Leu Pro Thr Phe Ile
            20                  25                  30
```

```
Leu Thr Ile Thr Tyr Leu Leu Ser Ile Trp Leu Gly Asn Lys Tyr Met
            35                  40                  45

Lys Asn Arg Pro Ala Leu Ser Leu Arg Gly Ile Leu Thr Leu Tyr Asn
 50                  55                  60

Leu Ala Ile Thr Leu Leu Ser Ala Tyr Met Leu Val Glu Leu Ile Leu
 65                  70                  75                  80

Ser Ser Trp Glu Gly Gly Tyr Asn Leu Gln Cys Gln Asn Leu Asp Ser
                 85                  90                  95

Ala Gly Glu Gly Asp Val Arg Val Ala Lys Val Leu Val Trp Tyr Tyr
                100                 105                 110

Phe Ser Lys Leu Val Glu Phe Leu Asp Thr Ile Phe Phe Val Leu Arg
            115                 120                 125

Lys Lys Ala Asn Gln Ile Thr Phe Leu His Val Tyr His His Ala Ser
130                 135                 140

Met Phe Asn Ile
145

<210> SEQ ID NO 49
<211> LENGTH: 302
<212> TYPE: PRT
<213> ORGANISM: Mortierella alpina

<400> SEQUENCE: 49

Phe Met Asp Leu Ala Thr Ala Ile Gly Val Arg Ala Ala Pro Tyr Val
  1               5                  10                  15

Asp Pro Leu Glu Ala Ala Leu Val Ala Gln Ala Glu Lys Tyr Ile Pro
                 20                  25                  30

Thr Ile Val His His Thr Arg Gly Phe Leu Val Ala Val Glu Ser Pro
            35                  40                  45

Leu Ala Arg Glu Leu Pro Leu Met Asn Pro Phe His Val Leu Leu Ile
 50                  55                  60

Val Leu Ala Tyr Leu Val Thr Val Phe Val Gly Met Gln Ile Met Lys
 65                  70                  75                  80

Asn Phe Glu Arg Phe Glu Val Lys Thr Phe Ser Leu Leu His Asn Phe
                 85                  90                  95

Cys Leu Val Ser Ile Ser Ala Tyr Met Cys Gly Gly Ile Leu Tyr Glu
                100                 105                 110

Ala Tyr Gln Ala Asn Tyr Gly Leu Phe Glu Asn Ala Ala Asp His Thr
            115                 120                 125

Phe Lys Gly Leu Pro Met Ala Lys Met Ile Trp Leu Phe Tyr Phe Ser
130                 135                 140

Lys Ile Met Glu Phe Val Asp Thr Met Ile Met Val Leu Lys Lys Asn
145                 150                 155                 160

Asn Arg Gln Ile Ser Phe Leu His Val Tyr His His Ser Ser Ile Phe
                165                 170                 175

Thr Ile Trp Trp Leu Val Thr Phe Val Ala Pro Asn Gly Glu Ala Tyr
            180                 185                 190

Phe Ser Ala Ala Leu Asn Ser Phe Ile His Val Ile Met Tyr Gly Tyr
            195                 200                 205

Tyr Phe Leu Ser Ala Leu Gly Phe Lys Gln Val Ser Phe Ile Lys Phe
210                 215                 220

Tyr Ile Thr Arg Ser Gln Met Thr Gln Phe Cys Met Met Ser Val Gln
225                 230                 235                 240

Ser Ser Trp Asp Met Tyr Ala Met Lys Val Leu Gly Arg Pro Gly Tyr
```

```
                        245                 250                 255
Pro Phe Phe Ile Thr Ala Leu Leu Trp Phe Tyr Met Trp Thr Met Leu
                260                 265                 270

Gly Leu Phe Tyr Asn Phe Tyr Arg Lys Asn Ala Lys Leu Ala Lys Gln
                275                 280                 285

Ala Lys Ala Asp Ala Ala Lys Glu Lys Ala Arg Lys Leu Gln
        290                 295                 300

<210> SEQ ID NO 50
<211> LENGTH: 271
<212> TYPE: PRT
<213> ORGANISM: Mus muculus

<400> SEQUENCE: 50

Met Asp Thr Ser Met Asn Phe Ser Arg Gly Leu Lys Met Asp Leu Met
  1               5                  10                  15

Gln Pro Tyr Asp Phe Glu Thr Phe Gln Asp Leu Arg Pro Phe Leu Glu
                 20                  25                  30

Glu Tyr Trp Val Ser Ser Phe Leu Ile Val Val Tyr Leu Leu Leu
             35                  40                  45

Ile Val Val Gly Gln Thr Tyr Met Arg Thr Arg Lys Ser Phe Ser Leu
 50                  55                  60

Gln Arg Pro Leu Ile Leu Trp Ser Phe Leu Ala Ile Phe Ser Ile
 65                  70                  75                  80

Leu Gly Thr Leu Arg Met Trp Lys Phe Met Ala Thr Val Met Phe Thr
                 85                  90                  95

Val Gly Leu Lys Gln Thr Val Cys Phe Ala Ile Tyr Thr Asp Asp Ala
                100                 105                 110

Val Val Arg Phe Trp Ser Phe Leu Phe Leu Leu Ser Lys Val Val Glu
            115                 120                 125

Leu Gly Asp Thr Ala Phe Ile Ile Leu Arg Lys Arg Pro Leu Ile Phe
130                 135                 140

Val His Trp Tyr His His Ser Thr Val Leu Leu Phe Thr Ser Phe Gly
145                 150                 155                 160

Tyr Lys Asn Lys Val Pro Ser Gly Gly Trp Phe Met Thr Met Asn Phe
                165                 170                 175

Gly Val His Ser Val Met Tyr Thr Tyr Tyr Thr Met Lys Ala Ala Lys
            180                 185                 190

Leu Lys His Pro Asn Leu Leu Pro Met Val Ile Thr Ser Leu Gln Ile
        195                 200                 205

Leu Gln Met Val Leu Gly Thr Ile Phe Gly Ile Leu Asn Tyr Ile Trp
    210                 215                 220

Arg Gln Glu Lys Gly Cys His Thr Thr Thr Glu His Phe Phe Trp Ser
225                 230                 235                 240

Phe Met Leu Tyr Gly Thr Tyr Phe Ile Leu Phe Ala His Phe His
                245                 250                 255

Arg Ala Tyr Leu Arg Pro Lys Gly Lys Val Ala Ser Lys Ser Gln
            260                 265                 270

<210> SEQ ID NO 51
<211> LENGTH: 265
<212> TYPE: PRT
<213> ORGANISM: Mortierella alpina

<400> SEQUENCE: 51

Thr Arg Gly Phe Leu Val Ala Val Glu Ser Pro Leu Ala Arg Glu Leu
```

```
                1               5                    10                   15
Pro Leu Met Asn Pro Phe His Val Leu Ile Val Leu Ala Tyr Leu
                       20                   25                   30
Val Thr Val Phe Val Gly Met Gln Ile Met Lys Asn Phe Glu Arg Phe
            35                   40                   45
Glu Val Lys Thr Phe Ser Leu Leu His Asn Phe Cys Leu Val Ser Ile
        50                   55                   60
Ser Ala Tyr Met Cys Gly Gly Ile Leu Tyr Glu Ala Tyr Gln Ala Asn
65                   70                   75                   80
Tyr Gly Leu Phe Glu Asn Ala Ala Asp His Thr Phe Lys Gly Leu Pro
                85                   90                   95
Met Ala Lys Met Ile Trp Leu Phe Tyr Phe Ser Lys Ile Met Glu Phe
            100                  105                  110
Val Asp Thr Met Ile Met Val Leu Lys Lys Asn Asn Arg Gln Ile Ser
        115                  120                  125
Phe Leu His Val Tyr His His Ser Ser Ile Phe Thr Ile Trp Trp Leu
    130                  135                  140
Val Thr Phe Val Ala Pro Asn Gly Glu Ala Tyr Phe Ser Ala Ala Leu
145                  150                  155                  160
Asn Ser Phe Ile His Val Ile Met Tyr Gly Tyr Tyr Phe Leu Ser Ala
                165                  170                  175
Leu Gly Phe Lys Gln Val Ser Phe Ile Lys Phe Tyr Ile Thr Arg Ser
            180                  185                  190
Gln Met Thr Gln Phe Cys Met Met Ser Val Gln Ser Ser Trp Asp Met
        195                  200                  205
Tyr Ala Met Lys Val Leu Gly Arg Pro Gly Tyr Pro Phe Phe Ile Thr
    210                  215                  220
Ala Leu Leu Trp Phe Tyr Met Trp Thr Met Leu Gly Leu Phe Tyr Asn
225                  230                  235                  240
Phe Tyr Arg Lys Asn Ala Lys Leu Ala Lys Gln Ala Lys Ala Asp Ala
                245                  250                  255
Ala Lys Glu Lys Ala Arg Lys Leu Gln
            260                  265

<210> SEQ ID NO 52
<211> LENGTH: 265
<212> TYPE: PRT
<213> ORGANISM: Caenorhabditis elegans

<400> SEQUENCE: 52

Ala Thr His Gly Pro Lys Asn Phe Pro Asp Ala Glu Gly Arg Lys Phe
1               5                    10                   15
Phe Ala Asp His Phe Asp Val Thr Ile Gln Ala Ser Ile Leu Tyr Met
                    20                   25                   30
Val Val Val Phe Gly Thr Lys Trp Phe Met Arg Asn Arg Gln Pro Phe
                35                   40                   45
Gln Leu Thr Ile Pro Leu Asn Ile Trp Asn Phe Ile Leu Ala Ala Phe
        50                   55                   60
Ser Ile Ala Gly Ala Val Lys Met Thr Pro Glu Phe Phe Gly Thr Ile
65                   70                   75                   80
Ala Asn Lys Gly Ile Val Ala Ser Tyr Cys Lys Val Phe Asp Phe Thr
                85                   90                   95
Lys Gly Glu Asn Gly Tyr Trp Val Trp Leu Phe Met Ala Ser Lys Leu
            100                  105                  110
```

```
Phe Glu Leu Val Asp Thr Ile Phe Leu Val Arg Lys Arg Pro Leu
            115                 120                 125

Met Phe Leu His Trp Tyr His His Ile Leu Thr Met Ile Tyr Ala Trp
    130                 135                 140

Tyr Ser His Pro Leu Thr Pro Gly Phe Asn Arg Tyr Gly Ile Tyr Leu
145                 150                 155                 160

Asn Phe Val Val His Ala Phe Met Tyr Ser Tyr Tyr Phe Leu Arg Ser
                165                 170                 175

Met Lys Ile Arg Val Pro Gly Phe Ile Ala Gln Ala Ile Thr Ser Leu
            180                 185                 190

Gln Ile Val Gln Phe Ile Ile Ser Cys Ala Val Leu Ala His Leu Gly
        195                 200                 205

Tyr Leu Met His Phe Thr Asn Ala Asn Cys Asp Phe Glu Pro Ser Val
    210                 215                 220

Phe Lys Leu Ala Val Phe Met Asp Thr Thr Tyr Leu Ala Leu Phe Val
225                 230                 235                 240

Asn Phe Phe Leu Gln Ser Tyr Val Leu Arg Gly Gly Lys Asp Lys Tyr
                245                 250                 255

Lys Ala Val Pro Lys Lys Asn Asn
            260             265

<210> SEQ ID NO 53
<211> LENGTH: 317
<212> TYPE: PRT
<213> ORGANISM: Mortierella alpina

<400> SEQUENCE: 53

Met Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
            20                  25                  30

Thr Gly Lys Ser Ile Asp Ser Phe Val Phe Gln Glu Gly Val Thr Pro
        35                  40                  45

Leu Ser Thr Gln Arg Glu Val Ala Met Trp Thr Ile Thr Tyr Phe Val
50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Leu Tyr Tyr Leu Asn Tyr Leu Val Lys Tyr Trp Glu
    130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
    210                 215                 220
```

-continued

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
            245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
            275                 280                 285

Ala Ala Lys Glu Arg Gly Ser Asn Phe Thr Pro Lys Thr Val Lys Ser
290                 295                 300

Gly Gly Ser Pro Lys Lys Pro Ser Lys Ser Lys His Ile
305                 310                 315

<210> SEQ ID NO 54
<211> LENGTH: 288
<212> TYPE: PRT
<213> ORGANISM: Caenorhabditis elegans

<400> SEQUENCE: 54

Met Ala Gln His Pro Leu Val Gln Arg Leu Leu Asp Val Lys Phe Asp
1               5                   10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn

```
                      275                 280                 285

<210> SEQ ID NO 55
<211> LENGTH: 282
<212> TYPE: PRT
<213> ORGANISM: Mortierella alpina

<400> SEQUENCE: 55
```

Ala Ala Leu Val Ala Gln Ala Glu Lys Tyr Ile Pro Thr Ile Val His
 1               5                  10                  15

His Thr Arg Gly Phe Leu Val Ala Val Glu Ser Pro Leu Ala Arg Glu
             20                  25                  30

Leu Pro Leu Met Asn Pro Phe His Val Leu Leu Ile Val Leu Ala Tyr
         35                  40                  45

Leu Val Thr Val Phe Val Gly Met Gln Ile Met Lys Asn Phe Glu Arg
     50                  55                  60

Phe Glu Val Lys Thr Phe Ser Leu Leu His Asn Phe Cys Leu Val Ser
65                  70                  75                  80

Ile Ser Ala Tyr Met Cys Gly Gly Ile Leu Tyr Glu Ala Tyr Gln Ala
                 85                  90                  95

Asn Tyr Gly Leu Phe Glu Asn Ala Ala Asp His Thr Phe Lys Gly Leu
            100                 105                 110

Pro Met Ala Lys Met Ile Trp Leu Phe Tyr Phe Ser Lys Ile Met Glu
        115                 120                 125

Phe Val Asp Thr Met Ile Met Val Leu Lys Lys Asn Asn Arg Gln Ile
130                 135                 140

Ser Phe Leu His Val Tyr His His Ser Ser Ile Phe Thr Ile Trp Trp
145                 150                 155                 160

Leu Val Thr Phe Val Ala Pro Asn Gly Glu Ala Tyr Phe Ser Ala Ala
                165                 170                 175

Leu Asn Ser Phe Ile His Val Ile Met Tyr Gly Tyr Tyr Phe Leu Ser
            180                 185                 190

Ala Leu Gly Phe Lys Gln Val Ser Phe Ile Lys Phe Tyr Ile Thr Arg
        195                 200                 205

Ser Gln Met Thr Gln Phe Cys Met Met Ser Val Gln Ser Ser Trp Asp
210                 215                 220

Met Tyr Ala Met Lys Val Leu Gly Arg Pro Gly Tyr Pro Phe Phe Ile
225                 230                 235                 240

Thr Ala Leu Leu Trp Phe Tyr Met Trp Thr Met Leu Gly Leu Phe Tyr
                245                 250                 255

Asn Phe Tyr Arg Lys Asn Ala Lys Leu Ala Lys Gln Ala Lys Ala Asp
            260                 265                 270

Ala Ala Lys Glu Lys Ala Arg Lys Leu Gln
        275                 280

```
<210> SEQ ID NO 56
<211> LENGTH: 278
<212> TYPE: PRT
<213> ORGANISM: Drosophila melanogaster
<220> FEATURE:
<221> NAME/KEY: VARIANT
<222> LOCATION: (235)...(235)
<223> OTHER INFORMATION: Xaa = Unknown or Other at position 235

<400> SEQUENCE: 56
```

Pro Thr Lys Met Ile Asn Met Asp Ile Ser Val Thr Pro Asn Tyr Ser
 1               5                  10                  15

```
Tyr Ile Phe Asp Phe Glu Asn Asp Phe Ile His Gln Arg Thr Arg Lys
            20                  25                  30

Trp Met Leu Glu Asn Trp Thr Trp Val Phe Tyr Tyr Cys Gly Ile Tyr
        35                  40                  45

Met Leu Val Ile Phe Gly Gly Gln His Phe Met Gln Asn Arg Pro Arg
    50                  55                  60

Phe Gln Leu Arg Gly Pro Leu Ile Ile Trp Asn Thr Leu Leu Ala Met
65                  70                  75                  80

Phe Ser Ile Met Gly Ala Ala Arg Thr Ala Pro Glu Leu Ile His Val
                85                  90                  95

Leu Arg His Tyr Gly Leu Phe His Ser Val Cys Val Pro Ser Tyr Ile
            100                 105                 110

Glu Gln Asp Arg Val Cys Gly Phe Trp Thr Trp Leu Phe Val Leu Ser
            115                 120                 125

Lys Leu Pro Glu Leu Gly Asp Thr Ile Phe Ile Val Leu Arg Lys Gln
    130                 135                 140

Pro Leu Ile Phe Leu His Trp Tyr His His Ile Thr Val Leu Ile Tyr
145                 150                 155                 160

Ser Trp Phe Ser Tyr Thr Glu Tyr Thr Ser Ser Ala Arg Trp Phe Ile
            165                 170                 175

Val Met Asn Tyr Cys Val His Ser Val Met Tyr Ser Tyr Tyr Ala Leu
            180                 185                 190

Lys Ala Ala Arg Phe Asn Pro Pro Arg Phe Ile Ser Met Ile Ile Thr
            195                 200                 205

Ser Leu Gln Leu Ala Gln Met Ile Ile Gly Cys Ala Ile Asn Val Trp
    210                 215                 220

Ala Asn Gly Phe Leu Lys Thr His Gly Thr Xaa Ser Cys His Ile Ser
225                 230                 235                 240

Gln Arg Asn Ile Asn Leu Ser Ile Ala Met Tyr Ser Ser Tyr Phe Val
            245                 250                 255

Leu Phe Ala Arg Phe Phe Tyr Lys Ala Tyr Leu Ala Pro Gly Gly His
            260                 265                 270

Lys Ser Arg Arg Met Ala
            275

<210> SEQ ID NO 57
<211> LENGTH: 286
<212> TYPE: PRT
<213> ORGANISM: Mortierella alpina

<400> SEQUENCE: 57

Val Thr Gly Lys Ser Ile Asp Ser Phe Val Phe Gln Glu Gly Val Thr
1               5                   10                  15

Pro Leu Ser Thr Gln Arg Glu Val Ala Met Trp Thr Ile Thr Tyr Phe
            20                  25                  30

Val Val Ile Phe Gly Gly Arg Gln Ile Met Lys Ser Gln Asp Ala Phe
            35                  40                  45

Lys Leu Lys Pro Leu Phe Ile Leu His Asn Phe Leu Thr Ile Ala
    50                  55                  60

Ser Gly Ser Leu Leu Leu Phe Ile Glu Asn Leu Val Pro Ile Leu
65                  70                  75                  80

Ala Arg Asn Gly Leu Phe Tyr Ala Ile Cys Asp Asp Gly Ala Trp Thr
                85                  90                  95

Gln Arg Leu Glu Leu Leu Tyr Tyr Leu Asn Tyr Leu Val Lys Tyr Trp
            100                 105                 110
```

```
Glu Leu Ala Asp Thr Val Phe Leu Val Leu Lys Lys Lys Pro Leu Glu
        115                 120                 125
Phe Leu His Tyr Phe His His Ser Met Thr Met Val Leu Cys Phe Val
    130                 135                 140
Gln Leu Gly Gly Tyr Thr Ser Val Ser Trp Val Pro Ile Thr Leu Asn
145                 150                 155                 160
Leu Thr Val His Val Phe Met Tyr Tyr Tyr Met Arg Ser Ala Ala
                165                 170                 175
Gly Val Arg Ile Trp Trp Lys Gln Tyr Leu Thr Thr Leu Gln Ile Val
            180                 185                 190
Gln Phe Val Leu Asp Leu Gly Phe Ile Tyr Phe Cys Ala Tyr Thr Tyr
        195                 200                 205
Phe Ala Phe Thr Tyr Phe Pro Trp Ala Pro Asn Val Gly Lys Cys Ala
    210                 215                 220
Gly Thr Glu Gly Ala Ala Leu Phe Gly Cys Gly Leu Leu Ser Ser Tyr
225                 230                 235                 240
Leu Leu Leu Phe Ile Asn Phe Tyr Arg Ile Thr Tyr Asn Ala Lys Ala
                245                 250                 255
Lys Ala Ala Lys Glu Arg Gly Ser Asn Phe Thr Pro Lys Thr Val Lys
            260                 265                 270
Ser Gly Gly Ser Pro Lys Lys Pro Ser Lys Ser Lys His Ile
        275                 280                 285

<210> SEQ ID NO 58
<211> LENGTH: 261
<212> TYPE: PRT
<213> ORGANISM: Drosophila melanogaster
<220> FEATURE:
<221> NAME/KEY: VARIANT
<222> LOCATION: (218)...(218)
<223> OTHER INFORMATION: Xaa = Unknown or Other at position 218

<400> SEQUENCE: 58

Ile Phe Asp Phe Glu Asn Asp Phe Ile His Gln Arg Thr Arg Lys Trp
1               5                   10                  15
Met Leu Glu Asn Trp Thr Trp Val Phe Tyr Tyr Cys Gly Ile Tyr Met
            20                  25                  30
Leu Val Ile Phe Gly Gly Gln His Phe Met Gln Asn Arg Pro Arg Phe
        35                  40                  45
Gln Leu Arg Gly Pro Leu Ile Ile Trp Asn Thr Leu Leu Ala Met Phe
    50                  55                  60
Ser Ile Met Gly Ala Ala Arg Thr Ala Pro Glu Leu Ile His Val Leu
65                  70                  75                  80
Arg His Tyr Gly Leu Phe His Ser Val Cys Val Pro Ser Tyr Ile Glu
                85                  90                  95
Gln Asp Arg Val Cys Gly Phe Thr Trp Leu Phe Val Leu Ser Lys
            100                 105                 110
Leu Pro Glu Leu Gly Asp Thr Ile Phe Ile Val Leu Arg Lys Gln Pro
        115                 120                 125
Leu Ile Phe Leu His Trp Tyr His His Ile Thr Val Leu Ile Tyr Ser
    130                 135                 140
Trp Phe Ser Tyr Thr Glu Tyr Thr Ser Ser Ala Arg Trp Phe Ile Val
145                 150                 155                 160
Met Asn Tyr Cys Val His Ser Val Met Tyr Ser Tyr Tyr Ala Leu Lys
                165                 170                 175
```

```
Ala Ala Arg Phe Asn Pro Pro Arg Phe Ile Ser Met Ile Ile Thr Ser
            180                 185                 190

Leu Gln Leu Ala Gln Met Ile Ile Gly Cys Ala Ile Asn Val Trp Ala
        195                 200                 205

Asn Gly Phe Leu Lys Thr His Gly Thr Xaa Ser Cys His Ile Ser Gln
        210                 215                 220

Arg Asn Ile Asn Leu Ser Ile Ala Met Tyr Ser Ser Tyr Phe Val Leu
225                 230                 235                 240

Phe Ala Arg Phe Phe Tyr Lys Ala Tyr Leu Ala Pro Gly Gly His Lys
                245                 250                 255

Ser Arg Arg Met Ala
            260

<210> SEQ ID NO 59
<211> LENGTH: 299
<212> TYPE: PRT
<213> ORGANISM: Homo sapiens

<400> SEQUENCE: 59

Met Glu His Phe Asp Ala Ser Leu Ser Thr Tyr Phe Lys Ala Leu Leu
 1               5                  10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
    50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
    210                 215                 220

Cys Thr Phe Pro Leu Gly Trp Leu Tyr Phe Gln Ile Gly Tyr Ile Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly
            260                 265                 270

Ser Val Ala Ala Val Asn Gly His Thr Asn Ser Phe Ser Pro Leu Glu
        275                 280                 285
```

```
Asn Asn Val Lys Pro Arg Lys Leu Arg Lys Asp
    290                 295
```

<210> SEQ ID NO 60
<211> LENGTH: 288
<212> TYPE: PRT
<213> ORGANISM: Caenorhabditis elegans

<400> SEQUENCE: 60

```
Met Ala Gln His Pro Leu Val Gln Arg Leu Leu Asp Val Lys Phe Asp
  1               5                  10                  15

Thr Lys Arg Phe Val Ala Ile Ala Thr His Gly Pro Lys Asn Phe Pro
             20                  25                  30

Asp Ala Glu Gly Arg Lys Phe Phe Ala Asp His Phe Asp Val Thr Ile
         35                  40                  45

Gln Ala Ser Ile Leu Tyr Met Val Val Phe Gly Thr Lys Trp Phe
     50                  55                  60

Met Arg Asn Arg Gln Pro Phe Gln Leu Thr Ile Pro Leu Asn Ile Trp
 65                  70                  75                  80

Asn Phe Ile Leu Ala Ala Phe Ser Ile Ala Gly Ala Val Lys Met Thr
                 85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn
        275                 280                 285
```

<210> SEQ ID NO 61
<211> LENGTH: 798
<212> TYPE: DNA
<213> ORGANISM: Homo sapiens

<400> SEQUENCE: 61

```
atgaacatgt cagtgttgac tttacaagaa tatgaattcg aaaagcagtt caacgagaat      60
gaagccatcc aatggatgca ggaaaactgg aagaaatctt tcctgttttc tgctctgtat     120
gctgccttta tattcggtgg tcggcaccta atgaataaac gagcaaagtt tgaactgagg     180
```

-continued

```
aagccattag tgctctggtc tctgacccct gcagtcttca gtatattcgg tgctcttcga      240
actggtgctt atatggtgta cattttgatg accaaaggcc tgaagcagtc agtttgtgac      300
cagggttttt acaatggacc tgtcagcaaa ttctgggctt atgcatttgt gctaagcaaa      360
gcacccgaac taggagatac aatattcatt attctgagga agcagaagct gatcttcctg      420
cactggtatc accacatcac tgtgctcctg tactcttggt actcctacaa agacatggtt      480
gccgggggag gttggttcat gactatgaac tatggcgtgc acgccgtgat gtactcttac      540
tatgccttgc gggcggcagg tttccgagtc tcccggaagt ttgccatgtt catcaccttg      600
tcccagatca ctcagatgct gatgggctgt gtggttaact acctggtctt ctgctggatg      660
cagcatgacc agtgtcactc tcactttcag aacatcttct ggtcctcact catgtacctc      720
agctaccttg tgctcttctg ccatttcttc tttgaggcct acatcggcaa aatgaggaaa      780
acaacgaaag ctgaatag                                                    798
```

<210> SEQ ID NO 62
<211> LENGTH: 265
<212> TYPE: PRT
<213> ORGANISM: Homo sapiens

<400> SEQUENCE: 62

```
Met Asn Met Ser Val Leu Thr Leu Gln Glu Tyr Glu Phe Glu Lys Gln
  1               5                  10                  15

Phe Asn Glu Asn Glu Ala Ile Gln Trp Met Gln Glu Asn Trp Lys Lys
                 20                  25                  30

Ser Phe Leu Phe Ser Ala Leu Tyr Ala Ala Phe Ile Phe Gly Gly Arg
             35                  40                  45

His Leu Met Asn Lys Arg Ala Lys Phe Glu Leu Arg Lys Pro Leu Val
         50                  55                  60

Leu Trp Ser Leu Thr Leu Ala Val Phe Ser Ile Phe Gly Ala Leu Arg
 65                  70                  75                  80

Thr Gly Ala Tyr Met Val Tyr Ile Leu Met Thr Lys Gly Leu Lys Gln
                 85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Val Asn Tyr Leu Val Phe Cys Trp Met Gln His Asp Gln
    210                 215                 220

Cys His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
                245                 250                 255
```

```
Lys Met Arg Lys Thr Thr Lys Ala Glu
        260                 265
```

<210> SEQ ID NO 63
<211> LENGTH: 33
<212> TYPE: DNA
<213> ORGANISM: Artificial Sequence
<220> FEATURE:
<223> OTHER INFORMATION: Internal Primer RO339

<400> SEQUENCE: 63
ttggagagga ggaagcgacc accgaagatg atg　　　　　　　　　　　　　33

<210> SEQ ID NO 64
<211> LENGTH: 31
<212> TYPE: DNA
<213> ORGANISM: Artificial Sequence
<220> FEATURE:
<223> OTHER INFORMATION: Forward Primer RO317

<400> SEQUENCE: 64
cacacaggaa acagctatga ccatgattac g　　　　　　　　　　　　　　31

<210> SEQ ID NO 65
<211> LENGTH: 35
<212> TYPE: DNA
<213> ORGANISM: Artificial Sequence
<220> FEATURE:
<223> OTHER INFORMATION: Primer RO350

<400> SEQUENCE: 65
catctcatgg atccgccatg gccgccgcaa tcttg　　　　　　　　　　　　35

<210> SEQ ID NO 66
<211> LENGTH: 18
<212> TYPE: DNA
<213> ORGANISM: Artificial Sequence
<220> FEATURE:
<223> OTHER INFORMATION: Reverse Primer RO352

<400> SEQUENCE: 66
acgcgtacgt aaagcttg　　　　　　　　　　　　　　　　　　　　　18

<210> SEQ ID NO 67
<211> LENGTH: 37
<212> TYPE: DNA
<213> ORGANISM: Artificial Sequence
<220> FEATURE:
<223> OTHER INFORMATION: Primer RO514

<400> SEQUENCE: 67
ggctatggat ccatgaattc actcgttact caatatg　　　　　　　　　　　37

<210> SEQ ID NO 68
<211> LENGTH: 35
<212> TYPE: DNA
<213> ORGANISM: Artificial Sequence
<220> FEATURE:
<223> OTHER INFORMATION: Primer RO515

<400> SEQUENCE: 68
cctgccaagc ttttacctttt tcttctgtg ttgag　　　　　　　　　　　　35

<210> SEQ ID NO 69
<211> LENGTH: 21
<212> TYPE: DNA

```
<213> ORGANISM: Artificial Sequence
<220> FEATURE:
<223> OTHER INFORMATION: Forward Primer RO541

<400> SEQUENCE: 69
gactactagc agctgtaata c                                              21

<210> SEQ ID NO 70
<211> LENGTH: 21
<212> TYPE: DNA
<213> ORGANISM: Artificial Sequence
<220> FEATURE:
<223> OTHER INFORMATION: Reverse Primer RO540

<400> SEQUENCE: 70
gtgaatgtaa gcgtgacata a                                              21

<210> SEQ ID NO 71
<211> LENGTH: 18
<212> TYPE: DNA
<213> ORGANISM: Artificial Sequence
<220> FEATURE:
<223> OTHER INFORMATION: Internal Forward Primer RO728

<400> SEQUENCE: 71
gagactttga gcggttcg                                                  18

<210> SEQ ID NO 72
<211> LENGTH: 20
<212> TYPE: DNA
<213> ORGANISM: Artificial Sequence
<220> FEATURE:
<223> OTHER INFORMATION: Internal Forward Primer RO730

<400> SEQUENCE: 72
tctctgctgc gttgaactcg                                                20

<210> SEQ ID NO 73
<211> LENGTH: 19
<212> TYPE: DNA
<213> ORGANISM: Artificial Sequence
<220> FEATURE:
<223> OTHER INFORMATION: Reverse Primer RO729

<400> SEQUENCE: 73
aaagctcttg acctcgaac                                                 19

<210> SEQ ID NO 74
<211> LENGTH: 20
<212> TYPE: DNA
<213> ORGANISM: Artificial Sequence
<220> FEATURE:
<223> OTHER INFORMATION: Reverse Primer RO731

<400> SEQUENCE: 74
aacttgatga acgacacgtg                                                20

<210> SEQ ID NO 75
<211> LENGTH: 29
<212> TYPE: DNA
<213> ORGANISM: Artificial Sequence
<220> FEATURE:
<223> OTHER INFORMATION: Primer RO719

<400> SEQUENCE: 75
ggttctccca tggaacattt tgatgcatc                                      29
```

-continued

<210> SEQ ID NO 76
<211> LENGTH: 30
<212> TYPE: DNA
<213> ORGANISM: Artificial Sequence
<220> FEATURE:
<223> OTHER INFORMATION: Primer RO720

<400> SEQUENCE: 76
ggtttcaaag ctttgacttc aatccttccg                                    30

<210> SEQ ID NO 77
<211> LENGTH: 37
<212> TYPE: DNA
<213> ORGANISM: Artificial Sequence
<220> FEATURE:
<223> OTHER INFORMATION: Primer RO738

<400> SEQUENCE: 77
aatcaggaat tcatggctca gcatccgctc gttcaac                            37

<210> SEQ ID NO 78
<211> LENGTH: 36
<212> TYPE: DNA
<213> ORGANISM: Artificial Sequence
<220> FEATURE:
<223> OTHER INFORMATION: Primer RO739

<400> SEQUENCE: 78
ccgcttgtcg acttagttgt tcttcttctt tggcac                             36

<210> SEQ ID NO 79
<211> LENGTH: 30
<212> TYPE: DNA
<213> ORGANISM: Artificial Sequence
<220> FEATURE:
<223> OTHER INFORMATION: Primer RP735

<400> SEQUENCE: 79
cctcctgaat tccaacacta ttcagctttc                                    30

<210> SEQ ID NO 80
<211> LENGTH: 20
<212> TYPE: DNA
<213> ORGANISM: Artificial Sequence
<220> FEATURE:
<223> OTHER INFORMATION: Primer RO73

<400> SEQUENCE: 80
taatacgact cactataggg                                               20

<210> SEQ ID NO 81
<211> LENGTH: 28
<212> TYPE: PRT
<213> ORGANISM: Homo sapiens

<400> SEQUENCE: 81

Asp Thr Ile Phe Ile Ile Leu Arg Lys Gln Lys Leu Ile Phe Leu His
 1               5                  10                  15

Trp Tyr His His Ile Thr Val Leu Leu Tyr Ser Trp
            20                  25

What is claimed is:

1. An isolated nucleic acid molecule having a nucleotide sequence with at least 95% homology to SEQ ID NO: 2, or the complement thereof, wherein the nucleic acid sequence encodes a functionally active elongase that utilizes a polyunsaturated fatty acid as a substrate.

2. The isolated nucleic acid molecule of claim 1 wherein said sequence is represented by SEQ ID NO:2.

3. A method of producing an elongase enzyme comprising the steps of:
   a) isolating the nucleotide sequence represented by SEQ ID NO:2;
   b) constructing a vector comprising: i) said isolated nucleotide sequence operably linked to ii) a promoter; and
   c) introducing said vector into a host cell under time and conditions sufficient for expression of said elongase enzyme.

4. The method of claim 3 wherein said host cell is selected from the group consisting of a eukaryotic cell and a prokaryotic cell.

5. The method of claim 4 wherein said prokaryotic cell is selected from the group consisting of *E. coli*, cyanobacteria, and *B. subtilis*.

6. The method of claim 4 wherein said eukaryotic cell is selected from the group consisting of a mammalian cell, an insect cell, a plant cell and a fungal cell.

7. The method of claim 6 wherein said fungal cell is selected from the group consisting of *Saccharomyces* spp., *Candida* spp., *Lipomyces starkey*, *Yarrowia* spp., *Kluyveromyces* spp., *Hansenula* spp., *Aspergillus* spp., *Penicillium* spp., *Neurospora* spp., *Trichoderma* spp. and *Pichia* spp.

8. The method of claim 7 wherein said fungal cell is a yeast cell selected from the group consisting of *Saccharomyces* spp., *Candida* spp., *Hansenula* spp. and *Pichia* spp.

9. The method of claim 8 wherein said yeast cell is *Saccharomyces cerevisiae*.

10. A vector comprising: a) a nucleotide sequence as represented by SEQ ID NO:2 operably linked to b) a promoter.

11. A host cell comprising said vector of claim 10.

12. The host cell of claim 11, wherein said host cell is selected from the group consisting of a eukaryotic cell and a prokaryotic cell.

13. The host cell of claim 12 wherein said prokaryotic cell is selected from the group consisting of *E. coli*, Cyanobacteria, and *B. subtilis*.

14. The host cell of claim 12 wherein said eukaryotic cell is selected from the group consisting of a mammalian cell, an insect cell, a plant cell and a fungal cell.

15. The host cell of claim 14 wherein said fungal cell is selected from the group consisting of *Saccharomyces* spp., *Candida* spp., *Lipomyces starkey*, *Yarrowia* spp., *Kluyveromyces* spp., *Hansenula* spp., *Aspergillus* spp., *Penicillium* spp., *Neurospora* spp., *Trichoderma* spp. and *Pichia* spp.

16. The host cell of claim 15 wherein said fungal cell is a yeast cell selected from the group consisting of *Saccharomyces* spp., *Candida* spp., *Hansenula* spp. and *Pichia* spp.

17. The host cell of claim 16 wherein said host cell is *Saccharomyces cerevisiae*.

18. A plant cell, plant or plant tissue comprising said vector of claim 10, wherein expression of said nucleotide sequence of said vector results in production of a polyunsaturated fatty acid by said plant cell, plant or plant tissue.

19. The plant cell, plant or plant tissue of claim 18 wherein said polyunsaturated fatty acid is selected from the group consisting of DGLA, 20:4n-3, and ADA.

* * * * *